United States Patent
Meng et al.

(10) Patent No.: US 11,685,951 B2
(45) Date of Patent: Jun. 27, 2023

(54) BIOMARKERS FOR INTRACRANIAL ANEURYSM

(71) Applicant: The Research Foundation for The State University of New York, Buffalo, NY (US)

(72) Inventors: Hui Meng, East Amherst, NY (US); Vincent Tutino, Buffalo, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 437 days.

(21) Appl. No.: 16/631,570

(22) PCT Filed: Jul. 18, 2018

(86) PCT No.: PCT/US2018/042718
§ 371 (c)(1),
(2) Date: Jan. 16, 2020

(87) PCT Pub. No.: WO2019/018545
PCT Pub. Date: Jan. 24, 2019

(65) Prior Publication Data
US 2020/0199676 A1    Jun. 25, 2020

Related U.S. Application Data

(60) Provisional application No. 62/534,072, filed on Jul. 18, 2017.

(51) Int. Cl.
*C12Q 1/6883*    (2018.01)

(52) U.S. Cl.
CPC ..... *C12Q 1/6883* (2013.01); *C12Q 2600/158* (2013.01)

(58) Field of Classification Search
CPC .................. C12Q 1/6883; G01N 2570/00
See application file for complete search history.

(56) References Cited

U.S. PATENT DOCUMENTS

| | | |
|---|---|---|
| 2002/0015957 A1 | 2/2002 | Hageman et al. |
| 2003/0119064 A1 | 6/2003 | Valkirs et al. |
| 2003/0199000 A1 | 10/2003 | Valkirs et al. |
| 2004/0121343 A1 | 6/2004 | Buechler et al. |
| 2004/0203083 A1 | 10/2004 | Buechler et al. |
| 2004/0209307 A1 | 10/2004 | Valkirs et al. |
| 2004/0219509 A1 | 11/2004 | Valkirs et al. |
| 2004/0253637 A1 | 12/2004 | Buechler et al. |
| 2005/0019865 A1 | 1/2005 | Kihm et al. |
| 2005/0130230 A1 | 6/2005 | Davalos et al. |
| 2005/0255484 A1 | 11/2005 | Valkirs et al. |
| 2005/0260697 A1 | 11/2005 | Wang et al. |
| 2006/0105419 A1 | 5/2006 | Blankenberg et al. |
| 2006/0257896 A1 | 11/2006 | Pollock et al. |
| 2007/0218498 A1 | 9/2007 | Buechler |
| 2008/0008696 A1 | 1/2008 | Hochstrasser et al. |
| 2009/0202991 A1 | 8/2009 | Pollock et al. |
| 2011/0143375 A1 | 6/2011 | Wang et al. |
| 2011/0294690 A1 | 12/2011 | Montaner Vilallonga |
| 2012/0015904 A1 | 1/2012 | Sharp et al. |
| 2012/0040846 A1 | 2/2012 | Kassis |
| 2012/0053073 A1 | 3/2012 | Kassis |
| 2012/0065087 A1 | 3/2012 | Sharp et al. |
| 2012/0238835 A1 | 9/2012 | Hyde et al. |
| 2012/0316076 A1 | 12/2012 | Sharp et al. |
| 2013/0189243 A1 | 7/2013 | Barr et al. |
| 2014/0148350 A1 | 5/2014 | Spetzler et al. |
| 2014/0179805 A1 | 6/2014 | Stylli |
| 2014/0187519 A1 | 7/2014 | Cooke et al. |
| 2015/0018234 A1 | 1/2015 | Sharp et al. |
| 2015/0152474 A1 | 6/2015 | Pawlowski et al. |
| 2016/0187349 A1 | 6/2016 | Kellum et al. |
| 2017/0356903 A1 | 12/2017 | Domenyuk et al. |

FOREIGN PATENT DOCUMENTS

| | | |
|---|---|---|
| WO | 2003/016910 A1 | 2/2003 |
| WO | 2004/059293 A2 | 7/2004 |
| WO | 2013/061342 A1 | 5/2013 |
| WO | 2015/095359 A1 | 6/2015 |
| WO | 2016/044021 A1 | 3/2016 |
| WO | 2017/089474 A1 | 6/2017 |
| WO | 2017/161357 A1 | 9/2017 |

OTHER PUBLICATIONS

Chan et al. G&P magazine. 2006. 6(3): 20-26. (Year: 2006).*
Chen et al. Molecular & Cellular Proteomics. 2002. 1:304-313. (Year: 2002).*
Greenbaum et al. Genome Biology. 2003. 4:117. (Year: 2003).*
Kendrick. "A gene's mRNA level does not usually predict its protein level". Kendrick Labs, Inc. Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*
Saito-Hisaminato et al. DNA Research. 2002. 9:35-45. (Year: 2002).*
Allantaz et al. PLoS ONE. 2012. 7(1):e29979. (Year: 2012).*
Kumar et al. Nature Communications. 2015. 6:Article No. 7971. (Year: 2015).*
Kleinloog et al. Stroke. 2016. 47(5):1286-1293 and Supplementary Materials. (Year: 2016).*
Yu et al. Neurosci Bull. 2014. 30(1):99-106. (Year: 2014).*
Bey et al. AJR. 2011. 196:32-44. (Year: 2011).*
Xu, Z. et al., Meta-Analysis of Microarray-Based Expression Profiles to Identify Differentially Expressed Genes in Intracranial Aneurysms, World Neurosurgery, Oct. 27, 2016, vol. 97, pp. 661-668.

(Continued)

*Primary Examiner* — Joseph G. Dauner
(74) *Attorney, Agent, or Firm* — Hodgson Russ LLP

(57) ABSTRACT

Provided are methods for determining a presence of an intracranial aneurysm in a subject suspected of having an intracranial aneurysm or at risk for developing an intracranial aneurysm, or a subject in need of aneurysm monitoring. The method involves analyzing a biological sample from the subject for expression of a combination of biomarkers that provide a signature of an aneurism.

4 Claims, 12 Drawing Sheets
Specification includes a Sequence Listing.

(56) References Cited

OTHER PUBLICATIONS

Zheng, X. et al., Identification of crucial genes in intracranial aneurysm based on weighted gene coexpression network analysis, Cancer Gene Therapy, Feb. 27, 2015, vol. 22, No. 5, pp. 238-245.
Roder, C. et al., Meta-Analysis of Microarray Gene Expression Studies on Intracranial Aneurysms, Neuroscience, Oct. 18, 2011, vol. 201, pp. 105-113.
Sabatino, G. et al., Transcriptional Profile Characterization for the Identification of Peripheral Blood Biomarkers in Patients with Cerebral Aneurysms, Journal of Biological Regulators & Homeostatic Agents, Jun. 30, 2013, vol. 27, No. 3, pp. 729-738.
Weinsheimer et al., Integration of expression profiles and genetic mapping data to identify candidate genes in intracranial aneurysm, Physiological Genomics, Sep. 18, 2007, vol. 32, No. 1, pp. 45-57.
Nikkola et al., Remote Ischemic Conditioning Alters Methylation and Expression of Cell Cycle Genes in Aneurysmal Subarachnoid Hemorrhage, Stroke, Aug. 6, 2015, vol. 46, No. 9, pp. 2445-2451.
Itutino et al., Circulating neutrophil transcriptome may reveal intracranial aneurysm signature, PLoS ONE, Jan. 17, 2018, vol. 13, No. 1, e0191407, pp. 1-22.
Dykstra-Aiello et al., Human Whole Blood Leukocytic RNA Expression After Stroke Differs by Etiology and Sex, University of California, Davis Doctoral Dissertation, 2017, 24 pages.

\* cited by examiner

BIOMARKERS FOR INTRACRANIAL ANEURYSM

CROSS REFERENCE TO RELATED APPLICATION

This application claims priority to U.S. provisional application no. 62/534,072, filed Jul. 18, 2017, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Jan. 16, 2020, is named Meng_Sequence_Listing.txt, and is 99,464 bytes in size.

FIELD

The present disclosure relates generally to biomarkers for intracranial aneurysm. The present disclosure is also related to the determination of aneurysm size and location by medical imaging following the assessment of aneurysm presence. The disclosure also relates to determining that the individual is at risk of intracranial aneurysm rupture, and/or for subarachnoid hemorrhage (SAH).

BACKGROUND

Intracranial aneurysms (IAs) are potentially deadly lesions in the cerebrovasculature that, if ruptured, cause devastating subarachnoid hemorrhages. Of the roughly 30,000 people in the United States per year who experience aneurysmal subarachnoid hemorrhage, approximately half die within one month, while half of the survivors live with permanent disability. It is estimated that 5% of Americans harbor unruptured IAs, but the exact prevalence is unknown. Since the majority of unruptured aneurysms are completely asymptomatic, most remain dormant and undetected. Aside from incidental discoveries on medical imaging performed for other purposes, IAs are often only discovered after rupture.

Clearly, early detection of IAs before they rupture is critical, as it would allow for vigilant monitoring by medical imaging and preventive treatment. Despite surgical risks, recent studies have demonstrated that treatment of unruptured IAs is able to drastically reduce the rate of rupture. For 50-year-old males, the probability of rupture during the patient's remaining lifetime is 22.8%, but is reduced to 1.6% after surgical clipping or 3.4% after endovascular coiling. Furthermore, preventative treatment of IAs has been found to be cost-effective, increasing the net quality-adjusted life-year. Screening tools that can identify patients with unruptured IAs would thus represent a major advance for patient care, as the detection and subsequent management of IAs could drastically reduce their catastrophic consequences and associated healthcare costs.

Unfortunately, screening for individuals with unruptured IAs is problematic. Stratifying risk for IA in the general population by environmental and genetic risk factors (e.g. age, female sex, and hypertension) does not reliably identify patients with unruptured aneurysm. These risk factors are often shared with other cardiovascular diseases and do not independently correlate with the presence of IA.

Unruptured IAs have been incidentally detected by magnetic resonance imaging (MRI), computed tomography angiography (CTA) or digital subtraction angiography (DSA), mostly performed for other reasons. Yet, as stated by the American Stroke Association, these imaging procedures are not suitable for IA screening, because the potential risks associated with them (e.g. some modalities are invasive and can cause complications) are not yet justified, especially considering their high cost. Even in high aneurysm risk populations (e.g. with family history of IA), it is debated whether patients should be screened by imaging, as its cost-effectiveness has not been clearly demonstrated. This raises a critical need for an alternative strategy for aneurysm detection that is minimally-invasive, affordable, and reliable. The present disclosure is pertinent to this need.

SUMMARY

The present disclosure provides methods for analysis of aneurisms, and in particular, IAs. In embodiments, the disclosure provides for determining the expression of any combination of biomarkers described herein. In embodiment, the disclosure provides a method for determining a presence (or absence) of an IA in a subject by analyzing a biological sample from the subject for expression of a combination of biomarkers that are described in Example 1, Table 2, and/or Example 2, Table 3, of this disclosure. In embodiments, the disclosure provides for determining the presence of an IA in an individual by determining a difference in expression of a combination of biomarkers described herein, relative to a control. In embodiments, determining that biomarkers as described herein are the same as a normal control indicates the individual does not have an IA. In embodiments, the disclosure provides for determining the presence of an IA by determining that expression of at least one of the following biomarkers is increased relative to a control: PVRL2, CYP1B1, CD177, PDE9A, ARMC12, OLAH, TGS1, CD163, LOC100506229, OCLN, SEMA6B, ADTRP, VWA8, MTRNR2L1, HOXB2, EPCAM, and IL18R1, and/or by determining that expression of at least one of the following biomarkers is decreased relative to a control: IGSF23, PTGES, G0S2, FCRL5, C1orf226, UTS2, HBG2, CYP26B1, and C1QL1.

In embodiments, the disclosure comprises determining that expression of at least one of the following biomarkers is increased relative to the control: PVRL2, PDE9A, TGS1, LOC100506229, OCLN, SEMA6B, MTRNR2L1, HOXB2, EPCAM, or IL18R1; and/or that expression of at least one of the following biomarkers is decreased relative to the control: IGSF23, PTGES, UTS2, HBG2, CYP26B1, or C1QL1.

In embodiments, expression of at least one of C21orf15, CYP1B1, FLT3, XKR3, SLC12A7, PAM, GPC4, FBN1, IL-8, GBP5, ETV7, MFSD9, SERPING1, TCL1A and CARD17 is analyzed.

In embodiments, the disclosure provides for determining increased expression of C21orf15, CYP1B1, FLT3, XKR3, SLC12A7, and PAM, relative to a control, and/or determining decreased expression of GPC4, FBN1, and IL-8 relative to the control, to indicate the presence of an IA.

In embodiments, the disclosure comprises determining increased expression C21orf15, CYP1B1, FLT3, XKR3, SLC12A7, PAM, and TCL1A relative to the control, and/or determining decreased expression of GPC4, FBN1, IL-8, GBP5, ETV7, MFSD9, SERPING1 and CARD17 relative to the control, to determine the presence of the IA.

In embodiments, the disclosure comprises determining the presence of the IA in the individual based on expression of the biomarkers, and performing a medical procedure on the individual. In certain approaches, the medical procedure comprises imaging the aneurysm. In certain approaches, the imaging comprises determining the size and location of the intracranial aneurysm. In embodiments, the medical procedure comprises determining that the intracranial aneurysm is a fusiform intracranial aneurysm, and optionally includes treating the fusiform intracranial aneurysm with a flow diverter. In embodiments, the medical procedure comprises determining that the intracranial aneurysm is a saccular intracranial aneurysm, and optionally includes treating the saccular intracranial aneurysm by endovascular coiling or surgical clipping.

In embodiments, the disclosure comprises repeating a method described herein to monitor the subject with respect to the size and/or location and/or a response to treatment of the intracranial aneurism.

In certain approaches, the disclosure comprises determining the presence of the IA in the individual, and further determining that the individual is at risk of having the IA rupture, and/or for subarachnoid hemorrhage (SAH).

DETAILED DESCRIPTION

Figure 1:
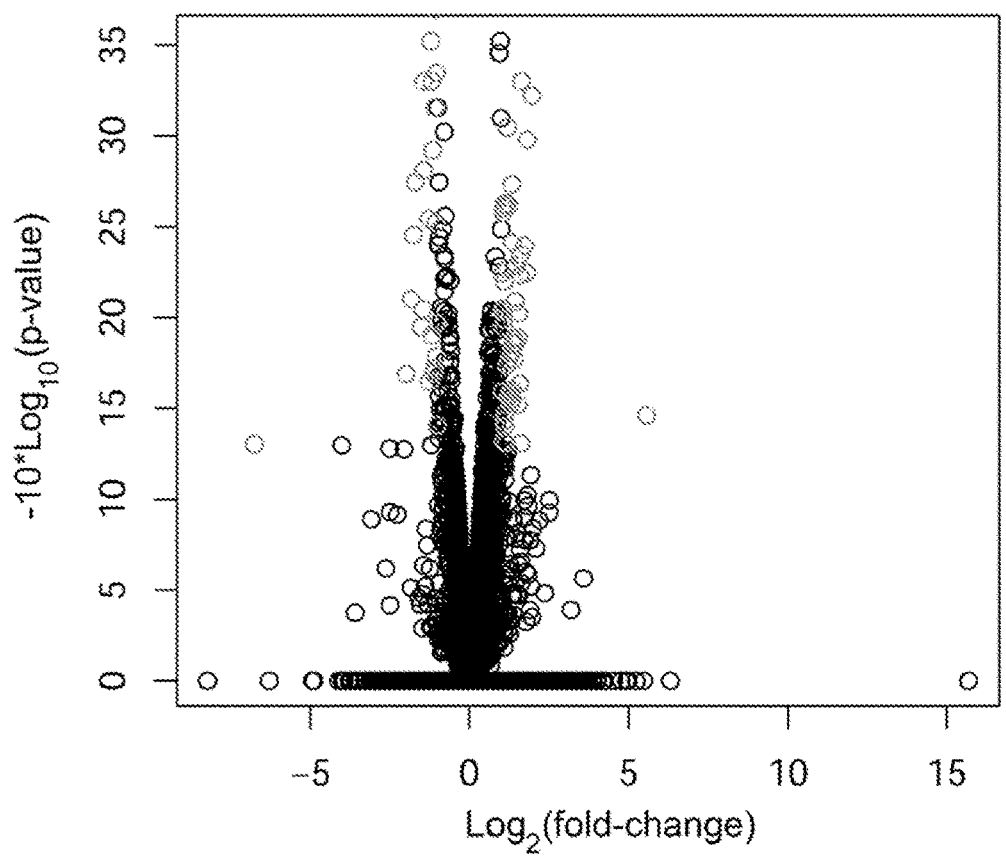
FIG. 1. Expression differences between patients with IAs and controls, and an IA-associated expression signature. The volcano plot demonstrates differential RNA expression between the two groups. Grey circles indicate an IA-associated signature of significantly differentially expressed transcripts ($p<0.05$) with an absolute fold-change$\geq 2$.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure provides methods for the diagnosis and/or prediction and/or intervention and/or treatment of aneurysms. In embodiments the disclosure relates to intracranial aneurysms. The present disclosure also provides methods for the determination of aneurysm size and location by medical imaging following determination of aneurysm presence. The present disclosure also provides methods for determining the risk of subarachnoid hemorrhage (SAH) and biomarkers useful for predicting such risk, since the intracranial aneurysms are responsible for as much as 90% of all non-traumatic SAH.

The present disclosure provides a method for determining the presence or absence of an intracranial aneurysm in a subject suspected of having an intracranial aneurysm, or at risk for developing an intracranial aneurysm, which method comprises analyzing a biological sample from the subject for differential expression of a biomarker as described herein. A subject suspected of having an intracranial aneurysm or at risk for an intracranial aneurysm is a subject who may be experiencing a headache (such as a pain above and behind an eye), a dilated pupil, a significant vision change, double vision, a drooping eyelid, numbness on a side, weakness on a side, paralysis on a side, difficulty with memory or speech, a seizure. In an embodiment, the side is a facial side. Additionally, a subject suspected of having an intracranial aneurysm or at risk for an intracranial aneurysm may have no symptoms at all. A subject may be at risk for an intracranial aneurysm due any of the following: old age, female gender, smoking, family history of aneurysm, hypertension, hyperlipidemia, and/or heart disease. In this application, the term, biomarker, is used to mean RNA or protein translated from said RNA. The RNA that is determined is typically coding RNA, such as a section of mRNA that codes for a protein described herein, or it may be non-coding RNA. As will be recognized by those skilled in the art, the presence, absence, and/or amount of RNA can be determined from, for example, DNA amplified from the RNA template, as well as by other methods that are described herein.

In developing the present disclosure we asked if circulating neutrophils carry transcriptional signatures of unruptured IA. Our rationale was twofold. Firstly, aneurysmal lesions are known to be associated with persistent vascular wall inflammation, and are in direct contact with circulating immune cells, including neutrophils, the most abundant white blood cell. Secondly, neutrophils, while generally considered non-specific in their function, have been shown to alter their transcriptomes in diseases characterized by inflammation—even short exposure to specific physiologic contexts can subtly alter their transcriptional programs. Indeed, RNA expression differences in circulating neutrophils have been demonstrated in idiopathic arthritis, sepsis, lung cancer, and the response to xenografts. Analysis of whole blood transcriptomes has also demonstrated that expression differences correlate with localized vascular diseases, including atherosclerosis, thoracic aortic aneurysm, coronary artery disease, and arteriovenous malformations.

Circulating neutrophils, being in continuous interaction with the aneurysm tissue, could also carry a signature of IA in their transcriptomes. Therefore, in at least the first Example of this disclosure, we asked if patients with IA present with different neutrophil RNA expression profiles compared to subjects without aneurysms. To this end, we matched two cohorts of patients with and without IAs by demographics and comorbidities, and performed next-generation RNA sequencing and an array of bioinformatics analyses to identify and characterize IA-associated expression differences in circulating neutrophils. Furthermore, to determine if biomarker differences revealed by RNA sequencing could be detected using inexpensive methods in a broader population, we performed a corroboration using RT-qPCR in a new, unmatched cohort of patients.

In embodiments, the disclosure provides a signature of biomarkers. "Signature" as used herein means a combination of informative biomarkers, but is not meant to exclude other biomarkers from combinations of markers that can be used in methods of this disclosure. For instance, an 82 biomarker signature is described in Example 1 below (see, Example 1, Table 2), but the signature can comprise alternative and/or additional biomarkers, 16 of which are described in Example 2. In particular, Example 2 expands on Example 1 to provide a combination of 26 biomarkers, which includes a set of 10 markers from the 82 biomarkers that are provided in Example 1, Table 2. The biomarkers described in Example 2 were selected for classification model training, and also constitute a biomarker signature as described herein.

Example 1, Table 2 includes Entrez Gene ID numbers for each of the 82 genes from which the RNA is transcribed, and GenBank Accession numbers for each transcript. Example 2, Table 3 provides 26 biomarkers, 10 of which overlap with the biomarkers described in Example 1, and includes GenBank Accession numbers for each transcript. The additional 16 biomarkers are in bold font in Example 2, Table 3. "Transcript" as used herein includes a cDNA sequence of an mRNA.

The sequences of each RNA (or a corresponding cDNA) can be determined by those skilled in the art using the Gene ID numbers and accession numbers provided herein. All sequences for all GenBank accession numbers described herein are incorporated herein by reference as they exist in the GenBank database as of the priority date of this application or patent. The disclosure includes all of the polynucleotide and amino acid sequences in these database entries, the mRNA equivalent of any cDNA entry, the cDNA equivalent of any RNA entry, and includes all isoforms and splice variants, if any, of such sequences.

It will be recognized form this disclosure post hoc power estimation and independent corroboration of expression differences indicates that the biomarker signatures described herein are consistently present in patients with IA. Thus, without intending to be bound by any particular theory, it is believed that this is the first description of biomarker signatures for unruptured IA, and in particular for biomarkers that are differentially expressed in in circulating neutrophils.

The disclosure includes determining the presence, absence, expression level and/or amount of at least one of the biomarkers described herein. Accordingly the disclosure includes analyzing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98 of the presently described biomarkers.

In certain embodiments, the invention comprises a method of determining the presence, absence, expression level and/or amount of at least one biomarker selected from the group consisting of C21orf15, CYP1B1, FLT3, XKR3, SLC12A7, PAM, GPC4, FBN1, IL-8, GBP5, ETV7, MFSD9, SERPING1, TCL1A and CARD17. In certain embodiments, the presence, absence, expression level and/or amount of 2, 3, 4, 5, 6, 7, 8, 9, 10, 11, 12, 13, 14 or 15 of these biomarkers are analyzed. In certain embodiments disclosure comprises a method of determining the presence, absence, expression level and/or amount of at least one biomarker selected from the group consisting of IL8, GBP5, ETV7, MFSD9, SERPING1, TCL1A, CARD17, PAM, XKR3, CYP1B1 and FBN1. IL8, GBP5, ETV7, MFSD9, SERPING1, TCL1A, CARD17, PAM, XKR3, CYP1B1 are the top 10 transcripts from a nearest shrunken centroids analysis as described in Example 1. FBN1, XKR3, ETV7, and MFSD9 can be used in a regression model to predict probability of aneurysm presence also as described in Example 1.

As described in Example 2, in embodiments, the invention comprises a method of determining the presence, absence, expression level and/or amount of at least one biomarker selected from the group consisting of PVRL2, CYP1B1, CD177, PDE9A, ARMC12, OLAH, TGS1, CD163, LOC100506229, OCLN, SEMA6B, ADTRP, VWA8, MTRNR2L10, HOXB2, EPCAM, IL18R1, IGSF23, PTGES, G0S2, FCRL5, C1orf226, UTS2, HBG2, CYP26B1, C1QL1, and combinations thereof. In certain embodiments, the invention includes determining the presence, absence, expression level and/or amount of at least one biomarker that includes at least one of PVRL2, PDE9A, TGS1, LOC100506229, OCLN, SEMA6B, MTRNR2L10, HOXB2, EPCAM, IL18R1, IGSF23, PTGES, UTS2, HBG2, CYP26B1, and C1QL1.

In embodiments, the disclosure comprises determining all or any combination of the following markers are upregulated, relative to a control: PVRL2 (NM_002856.2); CYP1B1 (NM_000104.3); CD177 (NM_020406.3); PDE9A (NM_002606.2); ARMC12 (NM_145028.4); OLAH (NM_018324.2); TGS1 (NM_024831.7); CD163 (NM_004244.5); LOC100506229 (NR_039975.1); OCLN (NM_002538.3); SEMA6B (NM_032108.3); ADTRP (NM_001143948.1); VWA8 (NM_015058.1); MTRNR2L1 (NM_001190708.1); HOXB2 (NM_002145.3); EPCAM (NM_002354.2); and IL18R1 (NM_003855.3). In an embodiment, the disclosure comprises determining that any one or any combination of the following markers are downregulated, relative to a control: IGSF23, (NM_001205280.1); PTGES, (NM_004878.4); G0S2, (NM_015714.3); FCRL5, (NM_031281.2); C1orf226, (NM_001135240.1); UTS2, (NM_021995.2); HBG2, (NM_000184.2); CYP26B1, (NM_019885.3); and C1QL1, (NM_006688.4). In embodiments, the disclosure comprises determining that all of the markers in this paragraph are upregulated and downregulated, respectively, relative to a control.

The invention is generally suitable for use with any biological sample obtained from an individual. The biological sample can be tested directly, or it can be subjected to a processing step to isolate, amplify or purify components of the sample before testing. In certain embodiments the biological sample comprises a liquid biological sample, such as whole blood. If desired the whole blood can be processed prior to testing, such as by separating certain blood components and/or cell types for testing. In certain embodiments, the sample comprises immune cells, such as neutrophils. In certain approaches the neutrophils can be separated from other blood components, such as peripheral blood mononuclear cells and plasma. In embodiments the sample can comprise neutrophils and erythrocytes. In embodiments, the sample comprises neutrophils with eosinophils, basophils, and mast cells, or any combination thereof. In embodiments, the erythrocytes can be lysed before testing the neutrophils. Neutrophils can be isolated from the biological sample by, for example, centrifugation. Neutrophils can be identified if desired by determining the CD66b+ biomarker, such as by flow cytometry. In some embodiments the biological sample tested does not comprise CD14+ cells as determined by flow cytometry.

Determining the presence, absence, expression levels and/or amount of the biomarkers described herein can be performed using any suitable approaches. In one approach wherein the biomarker is a protein, protein is determined, such as by using immunological-based approaches, such as any form of ELISA assays. In embodiments, RNA is detected and/or quantitated using any suitable approach including RNA sequencing. In certain implementations PCR amplifications are used, and can include separating RNA, such as total RNA or mRNA from a sample, and making and measuring cDNA from the RNA, and/or by using quantitative PCR approaches, including real-time PCR, such as quantitative reverse transcription PCR (RT-qPCR). In embodiments, determining biomarkers comprises RNA sequencing, SAGE (serial analysis of gene expression), hybridization-based techniques including but not limited to those performed using RNA microarrays, DNA microarrays, or tiling arrays, and in situ hybridizations, northern blotting, and capillary electrophoresis.

"Upregulated" and its various forms used herein means that expression of a particular mRNA is increased relative to a control. "Downregulated" and its various forms as used herein means expression of a particular mRNA is decreased relative to a control. Non-limiting examples of degrees of upregulation and downregulation are provided in the tables, figures, and examples of this disclosure.

Quantitative or qualitative determinations of the amount of each biomarker in a sample according to the present disclosure, including but not limited to whether expression of any particular biomarker is upregulated or downregulated, can be measured using any suitable technique and compared to any suitable reference, including but not necessarily limited to an established normal range, a standardized curve, positive, negative, or matched controls, etc. In embodiments, the amount of biomarker is compared to a suitable control value, such as a value obtained from determining the amount of the same biomarker in a reference, wherein the reference comprises one or more individuals who have been determined to be normal and as such have no detectable intracranial aneurysm, or one or more individuals who each have an un-ruptured intracranial aneurysm, or from one or more individuals who each have a ruptured intracranial aneurysm. In embodiments, determining that one or more biomarkers as described herein is the same or similar to a control, such as a normal control, can indicate the individual does not have an aneurysm. In embodiments, determining a difference relative to a control comprises determining a statistically significant difference. In embodiments, a p value is determined. In embodiments, determining a $p<0.05$ is a statistically significant difference. In embodiments, differences between biomarkers that qualify as distinguishing criteria are those differences that are statistically significant.

In certain embodiments, a control comprises biomarkers from an individual or individuals who have been determined to have an intracranial aneurism, which may be an aneurism of a certain size, or of a certain size range. With respect to size, it is the most widely used metric for assessing intracranial aneurysm (IA) rupture risk. This metric is typically measured as the length of the largest dimension of the aneurysm on medical imaging and has been adopted from longitudinal prospective studies that found that larger aneurysms are more likely to rupture. Specifically, the 2012 Unruptured Cerebral Aneurysm Study (UCAS) that included 5720 patients who had cerebral aneurysms found that the risk of rupture increased with increasing size of the aneurysm (UCAS Japan Investigators et al. NEJM 2012). The risk of rupture for aneurysms that were smaller than 5 mm was less than those that were 5 mm or larger. This analysis indicates that unruptured aneurysms larger than 5 mm should have a higher priority to be considered for treatment. A recent systematic review of the current literature by Malhotra et al. also support these findings (Malhotra et al. Ann Intern Med 2017). In 25 out of 26 studies in the literature, the annualized rupture rate for aneurysms 3 to 5 mm was 0.5%, but was 1% or greater for aneurysms 5 mm and above. In embodiments, the present disclosure thus relates to predicting the size of an aneurysm based on a determination of biomarkers described herein. In embodiments, a determination that an aneurism is at risk of rupture based on a prediction or estimation of its size is followed by a medical intervention, as described herein. In embodiments, a determination of a risk of IA rupture is based on predicting or estimating a size of an aneurysm as greater than 5 mm, by determining a combination of biomarkers as described herein.

Differential RNA and protein translated from mRNA, expression profiles can be developed and used in embodiments of the disclosure. In certain aspects the disclosure comprises determining increased expression and decreased expression of biomarkers relative to one or more suitable controls.

In certain embodiments, the disclosure comprises determining increased expression of at least one of C21orf15, CYP1B1, FLT3, XKR3, SLC12A7, and PAM, relative to a control. In certain embodiments the disclosure comprises determining decreased expression of at least one of GPC4, FBN1, and IL-8 relative to a control. In certain embodiments, the disclosure comprises determining increased expression of at least one of C21orf15, CYP1B1, FLT3, XKR3, SLC12A7 and PAM and determining decreased expression of at least one of GPC4, FBN1, and IL-8 relative to a control. In certain embodiments the disclosure comprises determining increased expression of 2, 3, 4, 5 or 6 of C21orf15, CYP1B1, FLT3, XKR3, SLC12A7 and PAM relative to a control. In certain embodiments the disclosure comprises determining decreased expression of 2 or all three of GPC4, FBN1, and IL-8 relative to a control. In certain embodiments the disclosure comprises determining increased expression of all of C21orf15, CYP1B1, FLT3, XKR3, SLC12A7 and PAM and determining decreased expression of all GPC4, FBN1, and IL-8 relative to suitable controls. In certain embodiments, the analyzing comprises determining increased expression of at least one of C21orf15, CYP1B1, FLT3, XKR3, SLC12A7, PAM, and TCL1A relative to a control, and/or determining decreased expression of at least one of GPC4, FBN1, IL-8, GBP5, ETV7, MFSD9, SERPING1, CARD17 relative to a control.

In certain embodiments, the disclosure comprises determining increased expression of at least one of PVRL2, CYP1B1, CD177, PDE9A, ARMC12, OLAH, TGS1, CD163, LOC100506229, OCLN, SEMA6B, ADTRP, VWA8, MTRNR2L10, HOXB2, EPCAM, IL18R1, relative to a control. In certain embodiments, the disclosure comprises determining increased expression of at least one of PVRL2, PDE9A, TGS1, LOC100506229, OCLN, SEMA6B, MTRNR2L10, HOXB2, EPCAM, and IL18R1, relative to a control.

In certain embodiments the disclosure comprises determining decreased expression of at least one of IGSF23, PTGES, G0S2, FCRL5, C1orf226, UTS2, HBG2, CYP26B1, and C1QL1, relative to a control. In certain embodiments the disclosure comprises determining decreased expression of at least one of IGSF23, PTGES, UTS2, HBG2, CYP26B1, and C1QL1, relative to a control.

In embodiments, the disclosure includes a computer-implemented process to determine or otherwise analyze biomarker expression, and/or compare biomarker expression to a control, and includes use of any software program described herein. In embodiments, the disclosure comprises fixing the determination of the biomarkers as disclosed herein in a tangible medium of expression, such as a compact disk, a DVD, or any other form of electronic file. Thus, tangible forms of media comprising a biomarker determination as set forth herein are included in the present disclosure. In embodiments, the invention includes communicating or otherwise transferring the tangible medium comprising the diagnostic determination to a health care provider, such as by electronically transmitting a file containing the determination to the health care provider.

In certain embodiments, the sample is obtained from an individual who is at risk for developing an aneurysm.

In certain aspects, determining differences in expression in one or any combination of the biomarkers relative to a control comprises a diagnosis of the presence or, and/or the likely presence of an aneurysm. In embodiments, determining differences in expression in one or any combination of the biomarkers relative to a control aids in a physician's diagnosis of an aneurysm. In certain implementations, determining differences in expression in one or any combination of the biomarkers relative to a control can be followed by a medical intervention, including but not necessarily limited to an angiogram, computed tomography angiography (CTA), digital subtraction angiography (DSA) or Magnetic Resonance Angiography (MRA), and surgical interventions, such as introducing a stent, endovascular clipping, coiling, stenting, Onyx treatment, carotid artery ligation, other occlusive surgeries, bypass or any combination of the forgoing, or any other medical device to inhibit rupture of the aneurysm. Imaging techniques such as computed tomography angiography (CTA), digital subtraction angiography (DSA) or Magnetic Resonance Angiography (MRA) can be used for confirmation of the presence or absence of an aneurysm. Thus, the invention may comprise a method for identifying a subject in need of confirmation of the presence of intracranial aneurysm(s), its location and geometry by imaging. The invention may further include an assessment of the risk of aneurysm rupture and, optionally, treatment plans.

In one embodiment, the differential analysis of the biomarker(s) is followed by determining the size, phenotype and location of the intracranial aneurysm by imaging. Determining aneurysm phenotype (or pathological sub-type) is important for clinical decision making because it can indicate which ones are dangerous (going to rupture) and need treatment or which ones are not dangerous and can be periodically monitored. Aneurysm size is one clinical parameter used to judge the rupture risk of an aneurysm: the UCAS study (UCAS Japan Investigators et al. NEJM 2012) demonstrated that aneurysms >5 mm had a greater probability of rupturing. Our data shows the differential RNA expression segregates patients by aneurysm size. (FIGS. 2B and C).

The invention also provides a method for determining the risk of subarachnoid hemorrhage (SAH) comprising analyzing a biological a sample for a differential expression of a biomarker as described herein. Subarachnoid hemorrhage (SAH) typically occurs due to bleeding of a ruptured intracranial aneurysm in the subarachnoid space surrounding the Circle of Willis at the base of the brain. The AANS reports that as much as 90 percent of SAHs can be attributed to the rupture of an IA. Hence, the presence of IA is likely the most correlative risk factor for non-traumatic SAH. The only know way to prevent SAH is to identify potential cerebral vascular complications before they occur. Detection of an unruptured IA before it ruptures is the only way to identify SAH early. Once detected, IAs can be treated, which has been demonstrated in the current literature to decrease the risk of future SAH. D'Souza J Neurosurg Anesthesiol 2015: The incidence of SAH in the United States is approximately 30,000 per year. (Brisman et al. NJM 2006). Ruptured IAs account for anywhere from 75% to 85% of non-traumatic SAH. (van Gijn and Rinkel Brain 2001).

In certain approaches the disclosure can be used to assess risk of aneurysm rupture or the risk of SAH. Current medical research uses size to delineate aneurysms at risk of rupture. FIGS. 2B and C and other data presented herein show that expression of neutrophils can separate aneurysm patients by the size of their aneurysm. The analysis in the figures was performed using whole Transcriptome data. Transcriptome data separated aneurysm samples by aneurysm size in the principal component space, forming groups of large IAs and small IAs.

These biomarkers may also increase or decrease as the aneurysm increases in size. Likewise, some of the biomarkers may increase or decrease dramatically if the aneurysm ruptures. Thus, they could be used to monitor aneurysm size or risk of progression to rupture.

Biomarker expression differences may also distinguish fusiform aneurysms from berry aneurysms, thin-walled IAs from thick-walled IAs, rupture-prone aneurysms from stable aneurysms etc. Fusiform aneurysms are aneurysms where the entire vessel is dilated. In saccular or berry aneurysms, the aneurysm forms a "berry" in part of the vessel. Fusiform aneurysms have fewer options to treat than saccular ones: they are generally not suitable for surgical clipping and for endovascular coiling. A suitable way to treat fusiform lesions is the recently emerged flow diverter treatment—deploying a densely woven stent mesh along the path of the parent vessel as a new conduit to divert the flow away, relying on the thrombosis (clotting) of the aneurysm and the reconstruction of the parent vessel to happen. Bypass is another treatment option. Irregularly shaped aneurysms are considered more likely to rupture than regularly shaped ones.

In embodiments the disclosure is used to monitor an individual, and thus multiple analyses of the presence, absence, expression level and/or amount of the biomarker can be obtained prior to, during, and/or subsequent to a medical intervention for confirming the presence of an aneurysm or a medical intervention for treating an aneurysm and/or reducing the risk of aneurysm rupture. This assessment may be periodically performed to monitor the subject. Accordingly, in certain aspects the disclosure comprises analysis of the biomarkers as described herein in a subject in need of aneurysm monitoring. The subject can be in need of monitoring for an aneurysm that was initially detected using any approach of this disclosure, or was detected using any other approach.

In embodiments, the disclosure comprises performing one or a combination of medical procedures described herein on an individual from whom a sample as described herein indicates the presence of an aneurysm. In embodiments, the sample indicates the presence of an IA that is at risk of rupture, and/or exceeds a size value, such as a threshold size value, as described herein. In embodiments, the disclosure thus comprises performing a medical procedure on an individual based at least in part on a result obtained by performing a method described herein. The disclosure accordingly includes selecting an individual to receive the medical procedure based at least in part on a result that includes a value for a combination of biomarkers, as described herein. In embodiments, the medical procedure comprises imaging of an area of the brain of the individual to confirm the presence, absence, location, size, ruptured or un-ruptured status, etc., of one or more IAs. In embodiments the medical imaging procedure comprises any of X-Ray, magnetic resonance imaging (MM), magnetic resonance angiography (MRA), computed tomography (CT), or digital subtraction angiography (DSA). In embodiments, the medical procedure comprises a surgical procedure. In embodiments, the surgical procedure comprises clipping, which is well known in the art as a surgical procedure for treating aneurisms, and involves introducing a clip at the base of the aneurysm to inhibit blood flow into the location of the aneurysm. In another embodiment, the surgical procedure comprises endovascular coiling, which is also a well know procedure for treating aneurisms, and involves inserting a coil into the aneurism to inhibit blood from entering it. In embodiments, the medical procedure comprises administering one or more pharmaceutical agents to the individual. In embodiments, the pharmaceutical agent comprises an agent that promotes blood clotting, such as an antifibrinolytic agent, such as aminocaproic acid or tranexamic acid.

In embodiments, the disclosure further comprises recommending a treatment protocol to an individual based at least in part on a diagnosis made by determining one or more biomarkers as described herein. The medical intervention or recommended treatment protocol may optionally comprise supplemental treatments, such as high blood pressure control and/or lifestyle modifications such as smoking cessation and/or weight loss.

The following Examples are meant to illustrate but not limit the invention.

Example 1

In this Example, transcriptome profiling identified 258 differentially expressed transcripts in patients with and without IAs. Expression differences were consistent with peripheral neutrophil activation. An IA-associated RNA expression signature was identified in 82 transcripts (p<0.05, fold-change ≥2). This signature was able to separate patients with and without IAs on hierarchical clustering. Furthermore, in an independent, unpaired, replication cohort of patients with IAs (n=5) and controls (n=5), the 82 transcripts separated 9 of 10 patients into their respective groups.

In more detail, in this Example, we investigated whether neutrophils have different RNA expression profiles in patients with IAs compared to patients without IAs. We recruited patients with and without aneurysms (confirmed on angiography) and paired them based on demographics and comorbidities. Next-generation RNA sequencing of circulating neutrophils was performed to identify an IA-associated expression signature in their transcriptomes. We further assessed if the IA-associated expression signature could distinguish patients with and without IA in a heterogeneous independent cohort of patients. Gene ontology analysis and physiological pathway modeling were used to determine the biological function of differentially expressed transcripts in IA.

The following materials and methods were used to obtain the results described in this Example.

Clinical Study

The study described in this Example was approved by an institutional review board. Methods were carried out in accordance with the approved protocol. Written informed consent was obtained from all subjects. Peripheral blood samples were collected from patients undergoing cerebral digital subtraction angiography (DSA): 35 patients had a positive IA diagnosis and 42 had a negative IA diagnosis (controls). Positive or negative IA diagnosis was confirmed by imaging, and patient medical records were collected for pairing patients with IAs to controls. Additionally, each patient's complete blood count, which was taken within 3 months of blood collection, was recorded.

Patients undergoing cerebral digital subtraction angiography (DSA) with positive and negative intracranial aneurysm (IA) diagnoses were enrolled in this study. Reasons for the patients to receive DSA included confirmation of findings from noninvasive imaging of the presence of IAs, vascular malformations, or carotid stenosis or follow-up noninvasive imaging of previously detected IAs. All consenting patients were older than 18 years, were English speaking, and had not received previous treatment for IA. To ensure that differences in the circulating neutrophils were not influenced by inherent inflammatory conditions, we excluded patients who potentially had altered leukocyte transcriptomes; this included patients who were pregnant, had recently undergone invasive surgery, were undergoing chemotherapy, had a body temperature above 37.78° C. (100° F.), had received solid organ transplants, had autoimmune diseases, and those who were taking prednisone or any other immunomodulating drugs. Furthermore, the included patients did not have any other known cerebrovascular malformations or extracranial aneurysms, including abdominal aortic aneurysms.

Sample Preparation

Sixteen mL of blood was drawn from the access catheter in the femoral artery and transferred into two 8 mL, citrated, cell preparation tubes (BD, Franklin Lakes, N.J.). Neutrophils were isolated within 1 hour of peripheral blood collection, according to known techniques. Cell preparation tubes were centrifuged at 1,700×g for 25 minutes to separate erythrocytes and neutrophils from mononuclear cells and plasma in the peripheral blood samples. Erythrocytes and neutrophils were collected into a 3 mL syringe and placed into an erythrocyte lysis buffer that was made in-house. After all erythrocytes were lysed, the neutrophils were isolated by centrifugation at 400×g for 10 min and disrupted and stored in TRIzol reagent (Life Technologies, Carlsbad, Calif.) at −80° C. until further processing. Neutrophils isolated in this fashion are more than 98% CD66b+ by flow cytometry and contain no contaminating CD14+ monocytes Total neutrophil RNA was extracted using TRIzol, according to the manufacturer's instructions. Trace DNA was removed by DNase I (Life Technologies, Carlsbad, Calif.) treatment. The RNA was purified using the RNeasy MinElute Cleanup Kit (Qiagen, Venlo, Limburg, Netherlands) and suspended in RNase-free water. After RNA isolation, the purity and concentration of RNA in each sample was measured by absorbance at 260 nm on a NanoDrop 2000 (Thermo Scientific, Waltham, Mass.), and 200-400 ng of RNA was sent to our university's Next-Generation Sequencing and Expression Analysis Core facility for further quality control. Precise RNA concentration was measured at the core facility via the Quant-iT RiboGreen Assay (Invitrogen, Carlsbad, Calif.) with a TBS-380 Fluorometer (Promega, Madison, Wis.), whereas the quality of the RNA samples was measured with an Agilent 2100 BioAnalyzer RNA 6000 Pico Chip (Agilent, Las Vegas, Nev.). RNA samples with 260/280≥1.9 and an RNA integrity number (RIN)≥6.0 were considered for RNA sequencing.

Cohort Creation

Before sequencing, samples from IA patients and control subjects were paired by demographics and comorbidities to control for confounding variables. First, samples that did not have acceptable RNA quality for sequencing were excluded. Next, each patient in the IA group was paired with a control subject by factors that have been reported in the literature to correlate with IA. These included (in order of decreasing importance) age, sex, smoking status (yes or no), presence of hypertension, presence of hyperlipidemia, and presence of heart disease. Matching criteria also included stroke history, presence of diabetes mellitus, and presence of osteoarthritis, when possible. With the exception of age, the factors used for matching were quantified as binary data points. The clinical factors were retrieved from the patients' medical records via a Patient Medical History form administered prior to imaging. Since this medical record contained self-reported information, the presence of each comorbidity was corroborated with each patients' reported list of medications (e.g. hypertension with lisinopril, hyperlipidemia with simvastatin, heart disease with metoprolol, stroke history with clopidogrel, diabetes mellitus with metformin, and osteoarthritis with NSAIDs/tramadol). We were able corroborate 84% of the clinical data points for patients' comorbidities through their medication history.

After performing the original experiments to identify an IA-associated neutrophil expression signature, we used the same clinical protocol to recruit an additional 5 patients with IAs and 5 IA-free controls into a small replication cohort (n=10) to test whether the IA-associated signature could separate IA patients from controls in the second cohort. Blood samples and RNA were handled in the same manner as those in the original cohort, and the same RNA sequencing and data analysis protocols were followed. However, prior to sequencing, we did not control for demographics and comorbidities to obtain a more heterogeneous cohort.

RNA Sequencing

RNA libraries for these samples were constructed at our university's Next-Generation Sequencing and Expression Analysis Core facility using the TruSeq RNA Library Preparation Kit (Illumina, San Diego, Calif.). All samples were subjected to 50-cycle, single-read sequencing in the HiSeq2500 (Illumina) and were demultiplexed using Bcl2Fastq v2.17.1.14 (Illumina). Gene expression analysis was completed using the Tuxedo Suite. Short RNA fragment data were compiled in FASTQ format and aligned to the human reference genome (human genome 19 [hg19]) using TopHat v2.1.13. Gene expression levels were calculated using fragments per kilobase of transcript per million mapped reads (FPKM) normalization in CuffLinks v2.2.1 RNA sequencing data files and processed transcript expression have been made available at NCBI's GEO (accession no. GSE106520). To evaluate the quality of RNA sequencing, we performed quality control analysis using both FASTQC before alignment and MultiQC after alignment.

Differential Expression Analysis

Differential gene expression analysis was performed in CuffDiff v2.2.1 and visualized in the CummeRbund v2.7.1 package in R. We used CuffDiff v2.2.1 (Trapnell Laboratory), which compared the log ratio of FPKM values in the IA and control groups against the log ratio of FPKM values of the IA group, and computed a test statistic. The test statistic was calculated using the negative binomial distribution to model the variance of each sample and the square root of the Jensen-Shannon divergence to assess differences in relative abundance. The change in Jensen-Shannon divergence was then assigned a p-value, according to a known approach.

Transcripts were considered significantly differentially expressed at $p<0.05$. We defined an IA-associated expression signature as those significant transcripts that also had an absolute fold-change $\geq 2$. Post hoc power estimation was performed following Hart et al. (Hart S N, Therneau T M, Zhang Y, Poland G A, Kocher J P (2013) Calculating sample size estimates for RNA sequencing data. J Comput Biol 20: 970-978) with $\alpha=0.05$, an average coefficient of variation of 0.404 (calculated from FPKMs), and counts per million mapped reads of 38. Multiple testing correction was performed by using the Benjamini-Hochberg method (Benjamini Y, Hochberg Y (1995) Controlling the False Discovery Rate: A Pratical and Powerful Approach to Multiple Testing. Journal of the Royal Statistical Society Series B (Methodological) 57: 289-300), and q-values were reported for each transcript.

Verification by RT-qPCR

To verify expression differences measured by RNA sequencing, quantitative reverse transcription polymerase chain reaction (RT-qPCR) was performed. We verified expression difference of 5 differentially expressed transcripts (CD177, SERPING1, GBP5, IL8, NAAA) in order to conserve RNA material. These 5 transcripts were chosen because they were among the most prominently differentially expressed transcripts, i.e., they were highly abundant (FPKM>10) and significantly differentially expressed ($p<0.05$) with an absolute fold-change >1.5. For each transcript, oligonucleotide primers were designed with a ~60° C. melting temperature and a length of 15-25 nucleotides to produce PCR products with lengths of 50-200 base pairs using Primer3 software and Primer BLAST (NCBI, Bethesda, Md.). The replication efficiency of each primer set was tested by performing qPCR on serial dilutions of cDNA samples (primer sequences, annealing temperatures, efficiencies, and product lengths are shown in Example 1, S1 Table).

For reverse transcription, first-strand cDNA was generated from total RNA using OmniScript Reverse Transcriptase kit (Qiagen, Venlo, Limburg, Netherlands) according to the manufacturer's instructions. Quantitative PCR was run with 10 ng of cDNA in 25μ reactions in triplicate in the Bio-Rad CFX Connect system (Bio-Rad, Hercules, Calif.) using ABI SYBR Green Master Mix (Applied Biosystems, Foster City, Calif.) and gene-specific primers at a concentration of 0.02 μM each. The temperature profile consisted of an initial step of 95° C. for 10 minutes, followed by 40 cycles of 95° C. for 15 seconds and 60° C. for 1 minute, and then a final melting curve analysis from 60° C. to 95° C. for 20 minutes. Gene-specific amplification was demonstrated by a single peak using the Bio-Rad dissociation melt curve. As previously described (Jiang K, Sun X, Chen Y, Shen Y, Jarvis J N (2015) RNA sequencing from human neutrophils reveals distinct transcriptional differences associated with chronic inflammatory states. BMC Med Genomics 8: 55), GAPDH expression was used for normalization, and fold-changes between groups were calculated using the $2^{-\Delta\Delta C_t}$ method.

Dimensionality Reduction

We performed dimensionality reduction by unsupervised principal component analysis (PCA) and multidimensional scaling (MDS) using the transcriptomes of each sample in the CummeRbund and prcomp packages in R Bioconductor under the default settings. For hierarchical clustering, we used the hclust package in R. Dendrograms were created using Ward linkage from z-score normalized transcript levels.

Bioinformatics

We performed gene set enrichment analysis using the open-source software GO::TermFinder (Stanford University School of Medicine, Stanford, Calif.). This tool determined whether any gene ontology terms annotated two lists of genes (i.e., genes with higher expression in samples from patients with IAs than those without IA and genes with lower expression in samples from patients with IAs than those without IA) greater than what would be expected by chance. Significantly enriched ontologies were reported if the Q-Value was <0.05, based on significance testing using the hypergeometric distribution.

Networks of potential interactions were generated using Ingenuity Pathway Analysis (IPA) software (Qiagen Inc., www.qiagenbioinformatics.com/products/ingenuity pathway-analysis). For IPA, each gene identifier was mapped to its corresponding gene object in the Ingenuity Knowledge Base and overlaid onto a molecular network derived from information accumulated in the Knowledge Base. Gene networks were algorithmically generated based on their "connectivity" derived from known interactions between the products of these genes. Networks were considered significant if their p-scores were >21.

The following results were obtained using the foregoing materials and methods.

Study Participants

Figure 6:
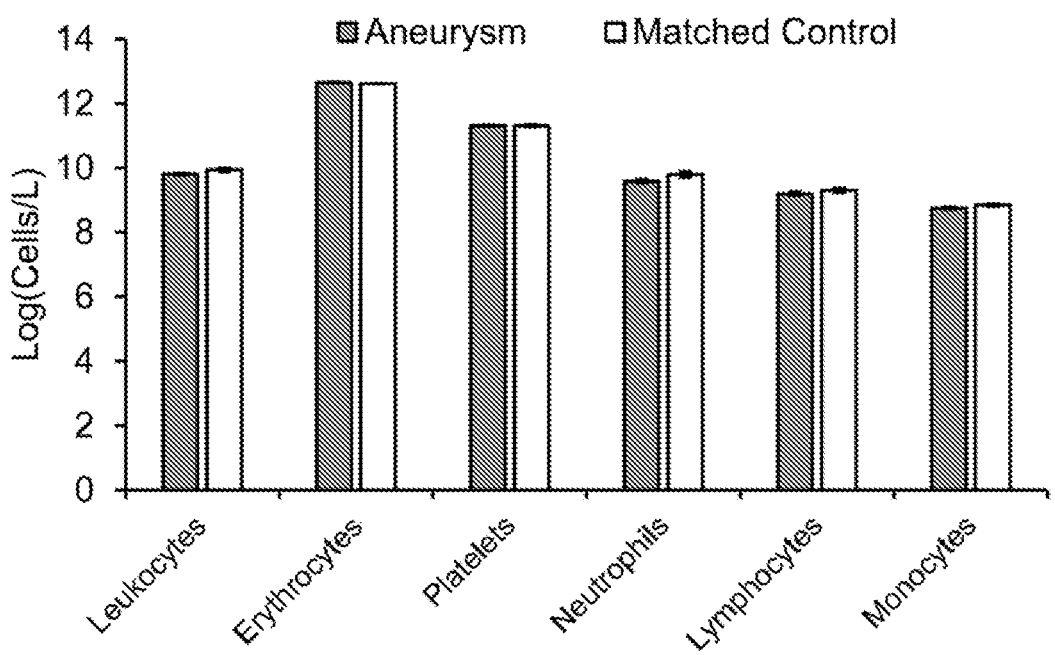
FIG. 6. White blood cell populations in the IA and control groups. There was no significant difference in white blood cell count or leukocyte ratios between patients with IAs (n=11) and controls (n=7, no data were available for 4 of the controls). (A) Complete blood count data recorded within 3 months of blood collection showed no significant difference between-groups in the concentrations of leukocytes, erythrocytes, platelets, neutrophils, lymphocytes, or monocytes ($p>0.05$, Student's t-test). (B) There was also no significant difference in the percentage (%) per 100 leukocytes for neutrophils, lymphocytes, monocytes, eosinophils, and basophils between patients with and without IA ($p>0.05$, Student's t-test). (Data points=average values, error bars=standard error).
Figure 6:
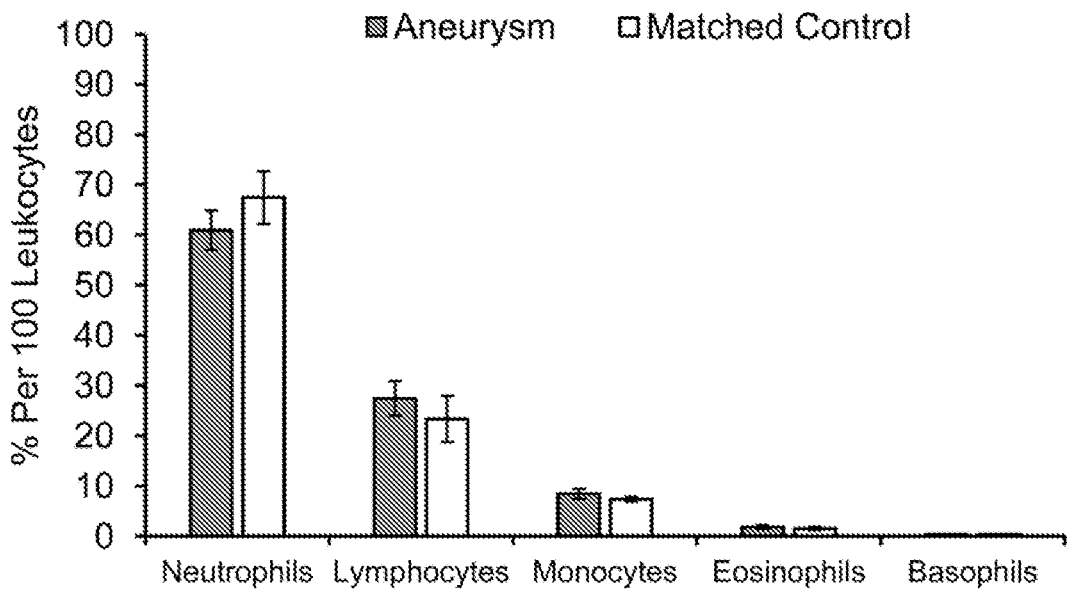

During the 6-month study period, we collected 77 blood samples (35 from patients with IA, 42 from control subjects) as well as angiographic images and medical records data from individuals undergoing cerebral DSA. Of the blood samples collected, 37 (16 from IA patients, 21 from controls) had a sufficient quality of neutrophil RNA for sequencing. Pairing on the basis of demographics and comorbidities resulted in a final cohort of 22 individuals, including 11 IA patients and 11 IA-free controls (Example 1, Table 1). These samples were of sufficient quality and had an average 260/280 of 2.02 and an average RIN of 7.04 (Example 1, S2 Table). Patients with IAs had aneurysms ranging in size from 1.5-19 mm, and included 3 individuals with multiple IAs (Example 1, S3 Table). There was no statistical difference in age (p>0.05, Student's t-test), and other factors (p>0.05, $\chi^2$ test) (Example 1, Table 1) as well as white blood cell populations between the two groups (p>0.05, Student's t-test) (FIG. 6).

Example 1,

TABLE 1

Clinical characteristics*

| | Patients with IA (n = 11) | Patients without IA (n = 11) | P-Value |
|---|---|---|---|
| Age (years) (Mean ± SE) | 66.91 ± 2.84 | 64.73 ± 4.22 | 0.67 |
| Age (years) [Median (Q1/Q3)] | 67 (60.5/72) | 70 (60/71.5) | |
| Sex | | | |
| Female | 63.64% | 54.55% | 0.66 |
| Current Smoker | | | |
| Yes | 18.18% | 18.18% | 1.00 |
| Comorbidities | | | |
| Hypertension | 63.64% | 81.82% | 0.34 |
| Hyperlipidemia | 45.45% | 54.55% | 0.67 |
| Heart disease | 18.18% | 27.27% | 0.61 |
| Stroke history | 0.00% | 9.09% | 0.31 |
| Diabetes mellitus | 18.18% | 36.36% | 0.34 |
| Osteoarthritis | 27.27% | 27.27% | 1.00 |

*We controlled for demographics and comorbidities so no factor was significantly higher in patients with IA or without IA (confirmed on imaging). There is no significant difference in age (p > 0.05 by Student's t-test) sex, smoking history, and comorbidities ($\chi^2$ > 0.05, chi-squared test) between the two groups. (IA = intracranial aneurysm, SE = standard error, Q = quartile)

Neutrophils Have an IA-Associated RNA Expression Signature

We performed RNA sequencing to identify differentially expressed neutrophil transcripts between 11 patients with IA and 11 paired controls. The sequencing had an average of 52.05 million sequences per sample and a 96.3% read mapping rate (% aligned) (Example 1, S4 Table). The volcano plot in FIG. 1 shows neutrophil expression differences between IA patients and controls in terms of average fold-change in expression and significance level. From 13,377 transcripts with testable expression differences, we identified 258 transcripts that were significantly differentially expressed (p<0.05) between the two groups. We defined an IA-associated RNA expression signature as significant transcripts that were increased or decreased by a factor of 2 or more. From the 258 transcripts, 82 met these criteria and are shown by the shaded circles in FIG. 1 and detailed in Example 1, Table 2. Post hoc power analysis estimated that a power of 0.8 was achieved in detecting expression differences of at least 1.68 fold at $\alpha=0.05$. Therefore, our statistical criteria of p<0.05 and absolute fold-change≥2 had power ≥0.8 in detecting this signature.

Example 1,

TABLE 2

82-transcript intracranial aneurysm-associated gene expression profile*

| Transcript | Gene ID | Accession No. | $Log_2$(F-C) | P-Value | Q-Value | |
|---|---|---|---|---|---|---|
| MAOA | 4128 | M69226.1 | 5.56 | 0.03455 | 0.9999 | |
| C21orf15 | 54055 | AY040090.1 | 2.38 | 0.00005 | 0.0836063 | * |
| CYP1B1 | 1545 | NM_000104.3 | 2.02 | 0.00005 | 0.0836063 | * |
| APMC12 | 221481 | NM_145028.4 | 1.95 | 0.0006 | 0.4459 | |
| CD177 | 57126 | NM_020406.3 | 1.81 | 0.001 | 0.585244 | |
| OLAH | 55301 | NM_018324.2 | 1.79 | 0.0057 | 0.9999 | |
| CYP1B1-AS1 | 285154 | NR_027252.1 | 1.73 | 0.004 | 0.9999 | |
| FLT3 | 2322 | NM_004119.2 | 1.63 | 0.00005 | 0.0836063 | * |
| CD163 | 9332 | DQ058615.1 | 1.62 | 0.0005 | 0.393441 | |
| KCNMA1 | 3778 | NM_001014797.2 | 1.61 | 0.050 | 0.9999 | |
| DACT1 | 51339 | NM_016651.5 | 1.60 | 0.0045 | 0.9999 | |
| FAM90A1 | 55138 | NM_018088.3 | 1.58 | 0.0059 | 0.9999 | |
| SCT | 6343 | AF244355.1 | 1.58 | 0.0232 | 0.9999 | |
| LOC100131289 | 100131289 | NR_038929.1 | 1.54 | 0.0095 | 0.9999 | |
| NOG | 9241 | NM_005450.4 | 1.52 | 0.013 | 0.9999 | |
| SCAMP5 | 192683 | NM_001178111.1 | 1.52 | 0.030 | 0.9999 | |
| PTGDS | 5730 | NM_000954.5 | 1.47 | 0.0052 | 0.9999 | |
| KIR2DS4 | 3809 | NM_012314.5 | 1.45 | 0.014 | 0.9999 | |
| CYP4F35P | 284233 | NR_026756. | 1.43 | 0.0082 | 0.9999 | |
| XKR3 | 150165 | NM_001318251.1 | 1.41 | 0.00005 | 0.0836063 | * |
| RPL39L | 116832 | NM_052969.2 | 1.40 | 0.017 | 0.9999 | |
| CDHR2 | 54825 | NM_001171976.1 | 1.35 | 0.013 | 0.9999 | |
| ENHO | 375704 | NM_198573.2 | 1.35 | 0.014 | 0.9999 | |
| SLC12A7 | 10723 | NM_006598.2 | 1.35 | 0.00005 | 0.0836063 | * |
| FLJ27354 | 400761 | NR_033981.1 | 1.34 | 0.025 | 0.9999 | |
| DGKH | 160851 | NM_152910.5 | 1.33 | 0.0039 | 0.9999 | |
| SDC3 | 9672 | AF248634.1 | 1.33 | 0.028 | 0.9999 | |
| THBS1 | 7057 | NM_003246.3 | 1.32 | 0.0019 | 0.85336 | |
| RCVRN | 5957 | NM_002903.2 | 1.30 | 0.016 | 0.9999 | |
| AKR1C1 | 1645 | NM_001353.5 | 1.30 | 0.030 | 0.9999 | |
| SCRG1 | 11341 | NM_001329597.1 | 1.28 | 0.027 | 0.9999 | |
| NRG1 | 3084 | NM_013959.3 | 1.26 | 0.030 | 0.9999 | |
| AK5 | 26289 | NM_174858.2 | 1.24 | 0.0024 | 0.9999 | |
| ITGA7 | 3679 | NM_001144996.1 | 1.23 | 0.017 | 0.9999 | |
| PAM | 5066 | NM_000919.3 | 1.20 | 0.00005 | 0.0836063 | * |
| LYPD2 | 137797 | NM_205545.2 | 1.19 | 0.028 | 0.9999 | |

TABLE 2-continued 82-transcript intracranial aneurysm-associated gene expression profile*

| Transcript | Gene ID | Accession No. | Log$_2$(F-C) | P-Value | Q-Value |
|---|---|---|---|---|---|
| PRUNE2 | 158471 | NM_015225.2 | 1.19 | 0.0009 | 0.547241 |
| SLC22A17 | 51310 | NM_020372.3 | 1.16 | 0.018 | 0.9999 |
| ADTRP | 84830 | NM_001143948.1 | 1.16 | 0.0054 | 0.9999 |
| ADAMTS1 | 9510 | NM_006988.4 | 1.15 | 0.0024 | 0.9999 |
| ECRP | 643332 | NR_033909.1 | 1.15 | 0.049 | 0.9999 |
| LOC100507387 | 100507387 | NR_03 8402.1 | 1.11 | 0.040 | 0.9999 |
| KLRC2 | 3822 | NM_002260.3 | 1.11 | 0.034 | 0.9999 |
| AKR1C3 | 8644 | NM_003739.5 | 1.09 | 0.0063 | 0.9999 |
| SEPT10 | 151011 | NM_144710.4 | 1.08 | 0.011 | 0.9999 |
| CYYR1 | 116159 | NM_001320768.1 | 1.08 | 0.037 | 0.9999 |
| TCL1A | 8115 | NM_021966.2 | 1.07 | 0.0024 | 0.9999 |
| VWF | 7450 | NM_000552.4 | 1.06 | 0.010 | 0.9999 |
| GNLY | 10578 | NM_001302758.1 | 1.06 | 0.0025 | 0.9999 |
| C4BPA | 722 | NM_000715.3 | 1.05 | 0.0027 | 0.9999 |
| LINC00482 | 284185 | NR_038080.1 | 1.05 | 0.048 | 0.9999 |
| K1AA1598 | 57698 | BC022348.1 | 1.04 | 0.0092 | 0.9999 |
| PID1 | 55022 | NM_017933.4 | 1.03 | 0.0090 | 0.9999 |
| SERPINF2 | 5345 | NM_000934.3 | 1.02 | 0.027 | 0.9999 |
| VWA8 | 23078 | NM_015058.1 | 1.01 | 0.0057 | 0.9999 |
| CYP4F2 | 8529 | NM_001082.4 | −1.00 | 0.039 | 0.9999 |
| FADS2 | 9415 | NM_004265.3 | −1.01 | 0.011 | 0.9999 |
| VLDLR | 7436 | NM_003383.4 | −1.03 | 0.0005 | 0.393441 |
| CARD17 | 440068 | NM_001007232.1 | −1.04 | 0.016 | 0.9999 |
| IL8 | 576 | AF043337.1 | −1.04 | 0.0001 | 0.148633 * |
| G0S2 | 50486 | NM_015714.3 | −1.05 | 0.003 | 0.9999 |
| FBXW8 | 26259 | NM_153348.2 | −1.08 | 0.0007 | 0.468195 |
| MFSD9 | 84804 | NM_032718.4 | −1.08 | 0.0002 | 0.26754 |
| CCL23 | 6368 | NM_005064.5 | −1.09 | 0.019 | 0.9999 |
| C1orf226 | 400793 | NM_001135240.1 | −1.11 | 0.020 | 0.9999 |
| GBP5 | 115362 | NM_052942.3 | −1.14 | 0.001 | 0.642096 |
| BATF2 | 116071 | NM_138456.3 | −1.17 | 0.0005 | 0.393441 |
| FCRL5 | 83416 | NM_031281.2 | −1.18 | 0.013 | 0.9999 |
| SERPING1 | 710 | NM_000062.2 | −1.21 | 0.0003 | 0.334425 |
| B4GALNT3 | 283358 | NM_173593.3 | −1.26 | 0.023 | 0.9999 |
| PDCD1LG2 | 80380 | NM_025239.3 | −1.28 | 0.0029 | 0.9999 |
| FBN1 | 2200 | NM_000138.4 | −1.33 | 0.00005 | 0.0836063 * |
| PRSS21 | 10942 | NM_006799.3 | −1.43 | 0.0016 | 0.797475 |
| ETV7 | 51513 | NM_016135.3 | −1.43 | 0.0005 | 0.393441 |
| SEPT4 | 5414 | NM_004574.4 | −1.46 | 0.009 | 0.9999 |
| EGR2 | 1959 | J04076.1 | −1.50 | 0.011 | 0.9999 |
| GBP1P1 | 400759 | NR_003133.2 | −1.70 | 0.0018 | 0.85336 |
| PSORS1C3 | 100130889 | AB932952.1 | −1.75 | 0.0035 | 0.9999 |
| HRK | 8739 | NM_003806.3 | −1.83 | 0.0079 | 0.9999 |
| NEB | 4703 | NM_001164507.1 | −1.98 | 0.020 | 0.9999 |
| GPC4 | 2239 | NM_001448.2 | −2.32 | 0.00005 | 0.0836063 * |
| LOC730441 | 207147 | BC039387.1 | −6.77 | 0.0498 | 0.9999 |

* Significantly differentially expressed transcripts with q-value <0.20 (20% FDR) are marked by "*".

Multiple hypothesis correction identified 9 transcripts with FDR<0.20; C21orf15, CYP1B1, FLT3, XKR3, SLC12A7, PAM, IL8, FBN1, and GPC4. Although this correction effectively reduced the number of significant transcripts, in embodiments, all 82 significant transcripts in the aneurysm-associated signature are analyzed. Individual genes that by themselves might not be significant (i.e., meet strict cutoffs of statistical tests that are not designed to find biologically relevant transcripts) could still play important roles in IA pathophysiology. To avoid missing potentially informative transcripts, we included all 82 transcripts in the IA-associated signature and in the clustering analysis.

Figure 2:
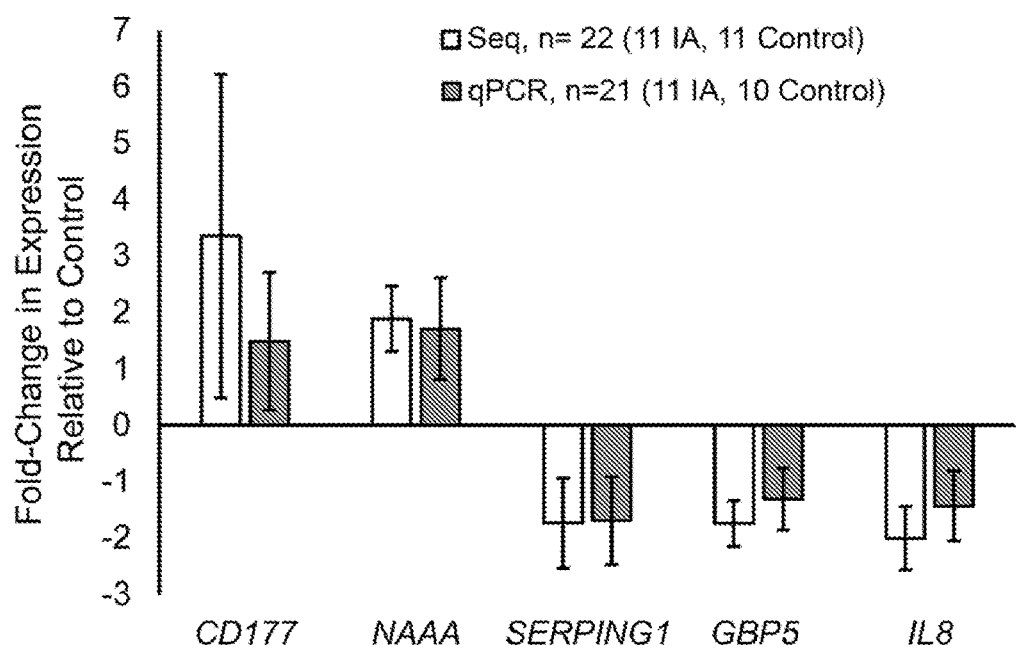
FIG. 2. Verification of RNA expression differences by RT-qPCR. Quantitative PCR performed on 5 prominent differentially expressed transcripts demonstrates that both the magnitude and direction of the fold-change in expression measured by RNA sequencing are similar to that measured by qPCR. Only 21 samples were analyzed by RT-qPCR because one control sample did not have enough RNA for the additional reactions. (Negative fold-change values calculated by negative inverse of fold-change, data points=average values, error bars=standard error.)

We confirmed differential expression of 5 prominent differentially expressed transcripts (CD177, NAAA, SERPING1, GBP5, and IL8) using RT-qPCR. FIG. 2 demonstrates that the expression differences between patients with and without IA are of the same direction and of similar magnitudes whether calculated from RNA sequencing or RT-qPCR. There was no statistically significant difference in fold-change of expression measured by the two methods (all p-values>0.05, Student's t-test).

Neutrophil RNA Expression Discriminates IA from Control Groups

Figure 3:
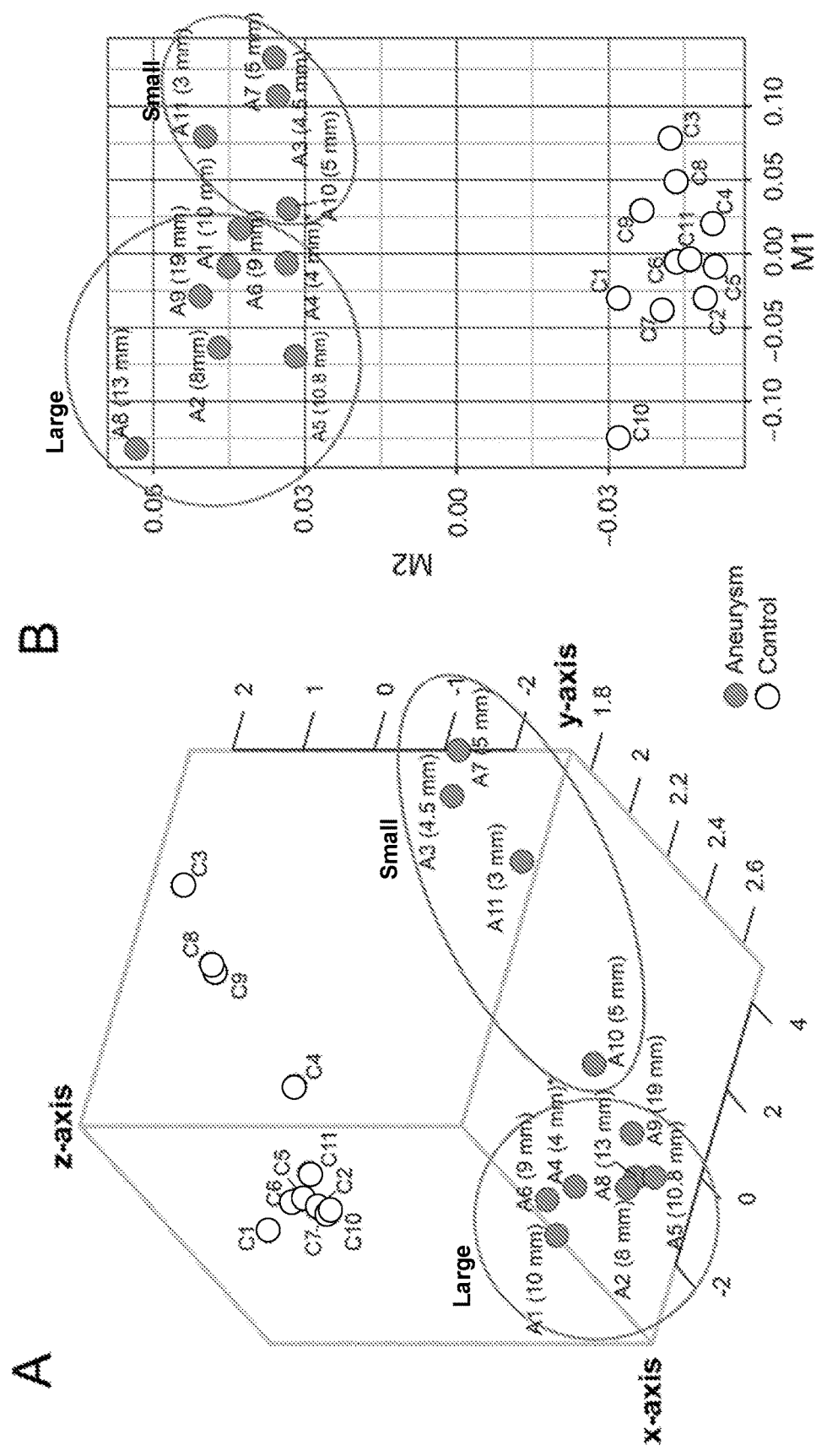
FIG. 3. Dimensionality reduction analyses separate blood samples from IA patients and controls. (A) Principal component analysis (PCA) using all transcriptome data demonstrates aggregation of samples from IA patients (dark filled dots) and controls (white dots). Transcriptome data further separated samples from IA patients by aneurysm size, forming groups of large IAs ($\geq 8$ mm, with one exception—see asterisk) and small IAs ($\leq 5$ mm). (B) Multidimensional scaling (MDS) of transcriptome data further reduces dimensionality and mirrors the PCA results, also showing separation of IA (dark filled dots) and control (white dots) samples. (C) Hierarchical clustering using only the 82-transcript IA-associated signature also demonstrates separation of IA and control groups. Four aneurysms samples on the right were more distinct than others, while the rest of the samples segregated into three main clusters, two containing all control and one containing all IA (with one exception). Overall, 91% of the samples were grouped with their respective group.
Figure 3:
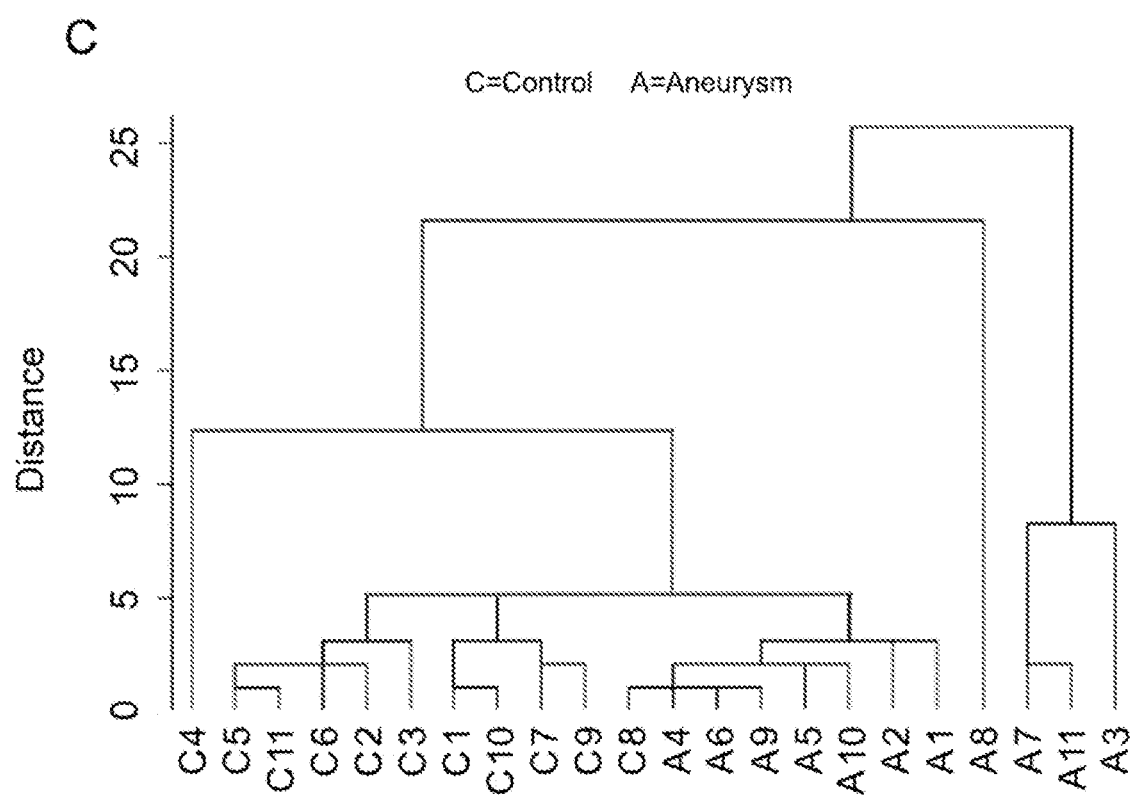

To visualize how well neutrophil RNA expression differentiated aneurysm samples from control samples, we performed dimensionality reduction analyses by PCA and MDS using all neutrophil transcriptome data (13,377 transcripts). FIG. 3A shows that the IA and control groups separated in the principal component space. Similarly, MDS also showed separation of patients with IAs and control subjects (FIG. 3B). We also found that the transcriptome data segregated the patients with IAs by the size of each patient's largest IA, forming two groups on both the PCA and MDS plots: large (≥8 mm, with one exception) and small (≤5 mm) (FIGS. 3A and 3B).

Using the expression signature of 82 transcripts (p<0.05 and absolute fold-change≥2), we performed supervised hierarchical clustering to determine whether it could also discriminate patients with IAs from controls. On the dendrogram in FIG. 3C, samples from IA and control groups are separated. Four samples from the IA group on the right were more distinct than the others. In the rest of the samples, one control (to the left) was separate, and all other samples segregated into 3 groups. Two groups contained all control samples and 1 group contained all IA samples (with 1 exception). In general, hierarchical clustering congregated 91% of the samples with their respective groups.

Expression Differences are Consistent with Leukocyte Activation

We performed bioinformatics analyses using gene set enrichment analysis and physiological pathway modeling. Some tightly controlled pathways can be regulated by transcripts that show small but significant changes. We performed bioinformatics analysis using all 258 differentially expressed transcripts ($p<0.05$) regardless of fold-change. As detailed in Example 1, Table 3, gene ontology analysis revealed that genes with higher neutrophil expression levels in the IA group were involved in defense response, leukocyte activation, stem cell maintenance, maintenance of cell number, cell activation, and stem cell development. Genes with lower expression levels in the IA group were involved in immune response and immune system process (Table 3).

Replication Study in a New, Unpaired Population

To determine whether expression of the IA-associated signature could separate patients with IAs from controls in an independent cohort, we performed a replication study. To do this, we recruited 10 additional patients (5 with IA, 5 IA-free controls) but did not control for demographics and comorbidities in order to assess the signature's potential for segregating patients in heterogeneous populations (see Example 1, S6 Table for clinical characteristics). Patients with IAs had aneurysms ranging in size from 1.4-7 mm and included one individual with multiple aneurysms (Example 1, S7 Table). From these patients' peripheral blood samples, we isolated neutrophils and extracted neutrophil RNA and performed next-generation RNA sequencing to obtain FPKM levels of the 82 IA-associated transcripts. To visualize how these transcripts could distinguish the IA group from the control group, we performed PCA and hierarchical clustering. With the exception of one IA sample, PCA demonstrated separation of the two groups in the principal

TABLE 3

Gene ontology (GO) analysis.*

| GO ID | Term | P-value | Q-value | Annotated Genes |
|---|---|---|---|---|
| | | Genes Increased in IA | | |
| GO:0006952 | Defense Response | 3.13E−06 | 2.36E−03 | KLRC2, VNN1, C4BPA, CD300E, SH2D1B, CD247, GNLY, INHBB, CD1D, KIR2DS4, PRF1, ORM2, STAB1, FCER1A, CD86 |
| GO:0045321 | Leukocyte Activation | 8.23E−06 | 6.21E−03 | VNN1, CD1D, CD7, PRF1, FCER1A, SH2D1B, SOX4, CD86, CD247 |
| GO:0019827 | Stem Cell Maintenance | 8.44E−06 | 6.37E−03 | NOG, TCL1A, KLF10, SCT, SOX4 |
| GO:0098727 | Maintenance of Cell Number | 8.95E−06 | 6.76E−03 | NOG, TCL1A, KLF10, SCT, SOX4 |
| GO:0001775 | Cell Activation | 1.18E−05 | 8.92E−03 | VNN1, CD7, VWF, SH2D1B, SOX4, CD247, CD1D, PRF1, FCER1A, CD86 |
| GO:0048864 | Stem Cell Development | 1.20E−05 | 9.10E−03 | NOG, DAB2, TCL1A, KLF10, SCT, SOX4 |
| | | Genes Decreased in IA | | |
| GO:0006955 | Immune Response | 1.17E−07 | 6.85E−05 | AIM2, LILRA4, FCRL5, IL8, MOV10, CYSLTR2, IFI35, PDCD1LG2, RGS1, CD274, CCL23, DDX60, OLFM4, GBP1 |
| GO:0002376 | Immune System Process | 3.32E−07 | 1.94E−04 | MOV10, CEBPE, SMPD3, IFI35, PDCD1LG2, CCL23, OLFM4, GBP1, AIM2, FCRL5, LILRA4, IL8, CYSLTR2, RGS1, CD274, DDX60 |

*Gene set enrichment analysis was performed on significantly differentially expressed genes (p < 0.05) in peripheral blood samples obtained from patients with intracranial aneurysms (IA). Significantly enriched ontologies present in genes with higher expression levels included defense response, leukocyte activation, stem cell maintenance, maintenance of cell number, cell activation, and stem cell development. Significantly enriched ontologies present in genes with lower expression levels included immune response and immune system process. Enriched ontologies from the GO database were considered significant at a false discovery rate-corrected p-value (q-value) <0.05.

Figure 4:
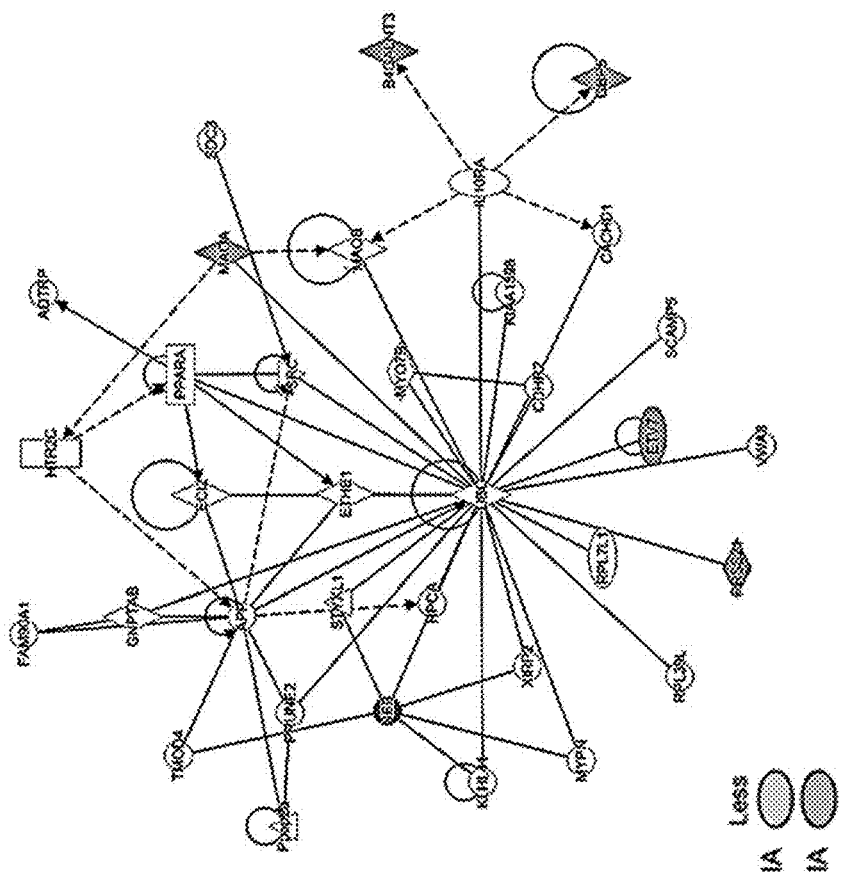
FIG. 4. The 4 most regulated networks. Networks were derived from IPA of differentially expressed transcripts ($p<0.05$) in neutrophils from IA patients and controls. Fold-change is represented by intensity of grey shading. Non-differentially expressed transcripts with known interactions have no grey color. (A) This network (p-score=41) shows regulation of transcripts with increased expression by an ERK1/2 and AP1. IL8, regulates transcripts with lower expression in samples from patients with IAs. (B) This network (p-score=30) shows regulation of transcripts by UBC. (C) This network (p-score=30) shows two nodes of regulation at AKT and VEGF. (D) This network (p-score=23) shows regulation of transcripts with lower expression in IA samples by IFNG.
Figure 4:
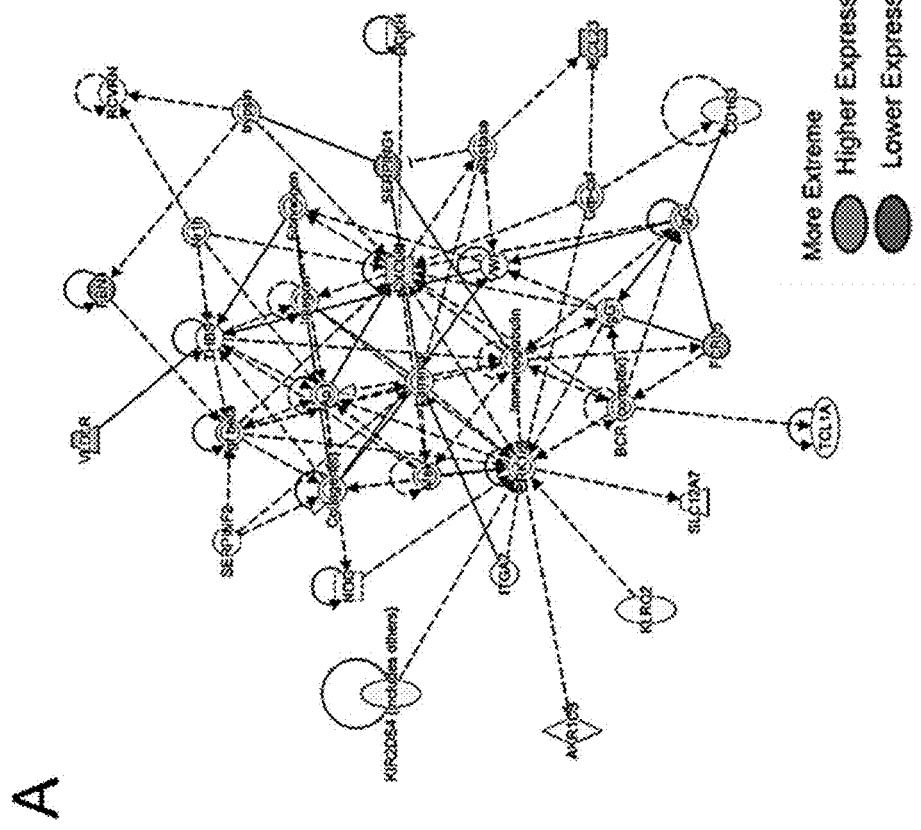
Figure 4:
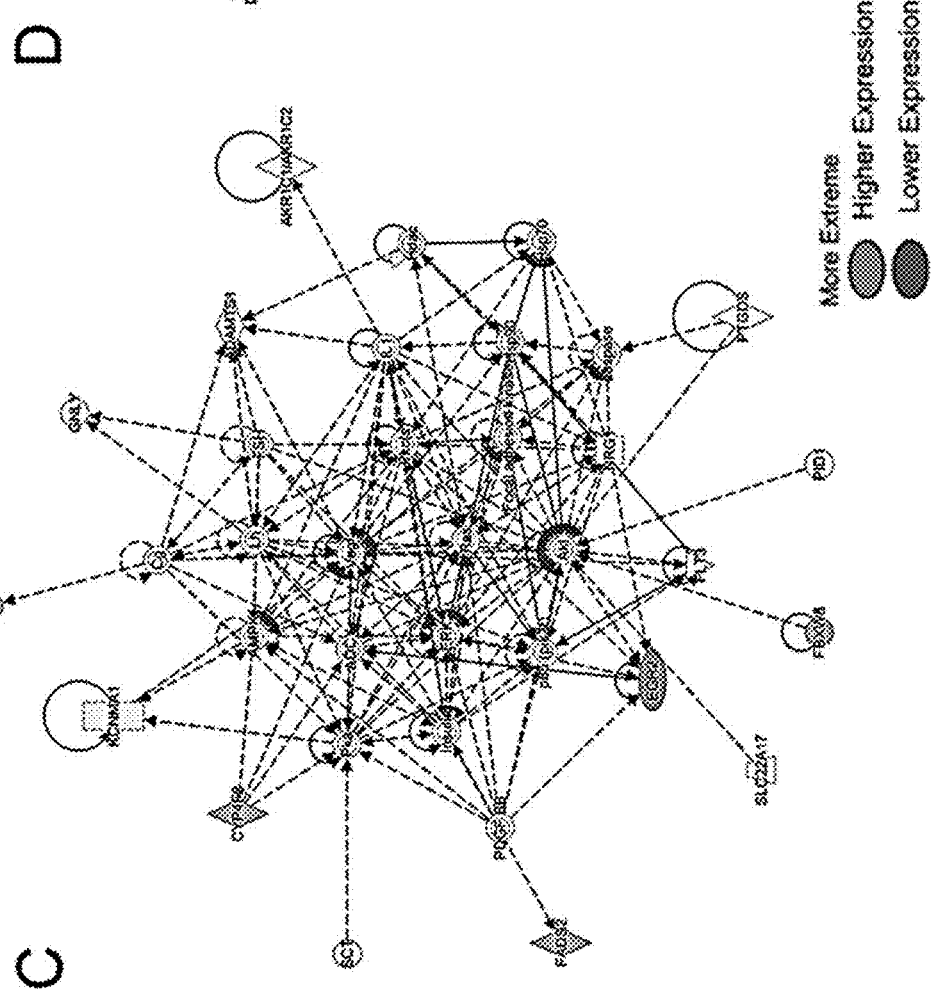
Figure 5:
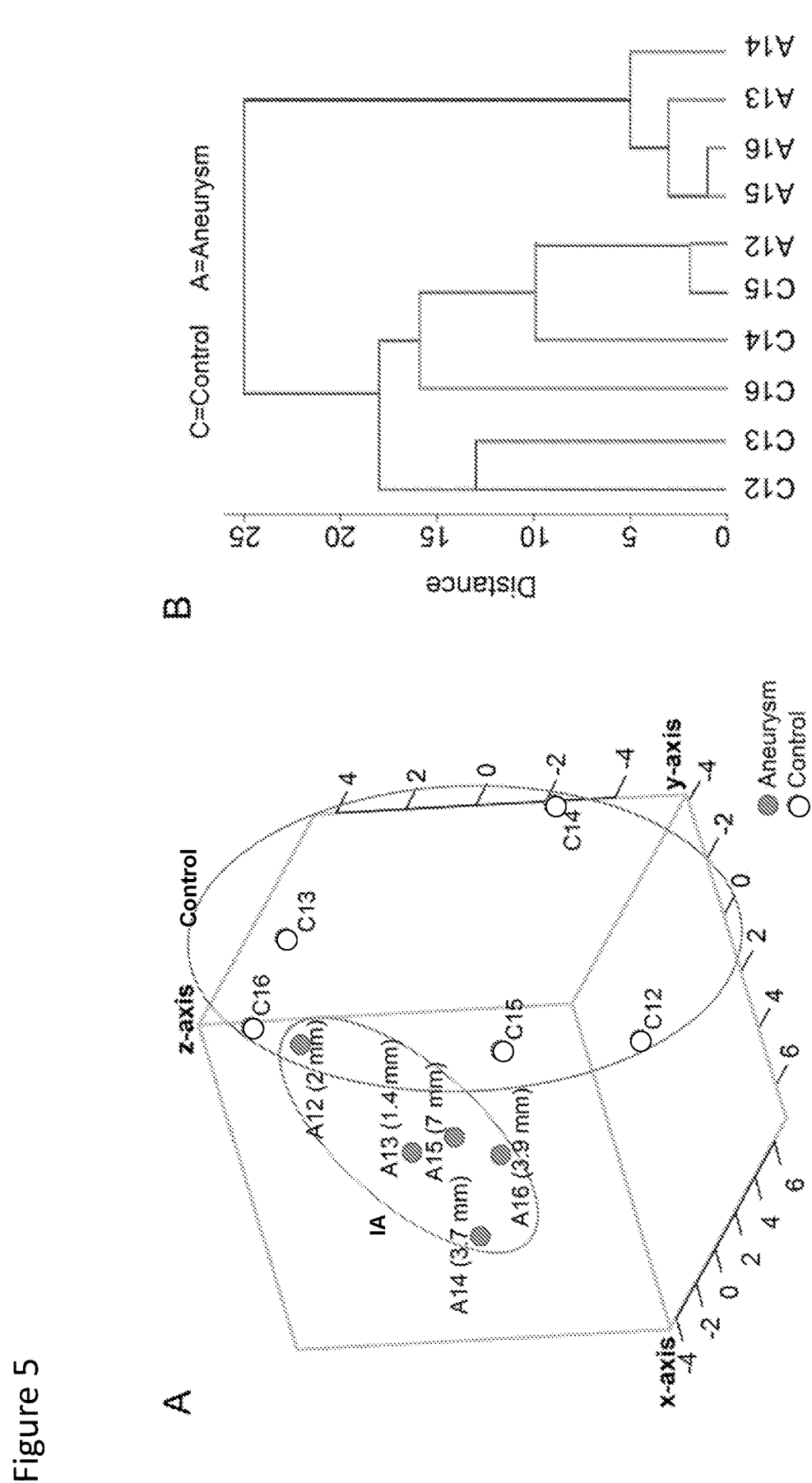
FIG. 5. Replication study in a cohort of 10 new patients (5 with IAs). (A) Principal component analysis performed using the 82 IA-associated transcripts shows separation of IA patients (dark filled dots) from controls (white dots) in this unmatched cohort. (B) Hierarchical cluster analysis demonstrates separation of the IA and control samples, with the exception of one IA sample that was grouped with controls.

Physiological pathway modeling to identify networks of potential interactions revealed 4 networks with 7 signaling nodes forming hubs within the networks (FIG. 4). These hubs included ERK1/2 and AP1; IL8 (CXCL8), AKT and VEGF; UBC; and IFNG. IPA indicated that these networks were consistent with activation of cellular movement and cardiovascular system function (network A), lipid metabolism (network B), cell-to-cell signaling and energy production (network C), and organismal injury, cell proliferation, and tissue morphology (network D). These functions are pertinent to neutrophil responses to intravascular perturbations. See Example 1, S5 Table for a list of names and biological functions of the transcripts in these 4 networks.

component space (FIG. 5A). Hierarchical clustering mirrored this result, grouping the IA and control samples separately, with the exception of one IA sample (FIG. 5B). Deidentified patient metadata is presented in Example 1, S8 Table.

It will be recognized by the foregoing description in this Example that we performed transcriptome profiling on circulating neutrophils from paired patients with and without IAs and identified an aneurysm-associated signature of 82 transcripts. These transcripts discriminated patients with and without IA in hierarchical cluster analysis. In a replication study, this signature also distinguished patients with IAs from controls in an unpaired cohort.

Previous Efforts in Search of Circulating Aneurysm Biomarkers

The search for circulating biomarkers for unruptured IAs has spanned more than two decades. A meta-analysis (Hussain S, Barbarite E, Chaudhry N S, Gupta K, Dellarole A, et al. (2015) Search for Biomarkers of Intracranial Aneurysms: A Systematic Review. World Neurosurg 84: 1473-1483) of IA biomarker publications from 1994-2015 found 5 studies that linked IA presence to specific biomolecules in the blood. These studies found that serum elastase-to-A1AT ratios and LPA, VEGF, MCP-1, IL-1β, TNF-α, and GM-CSF levels were elevated in patients with unruptured aneurysms. However, in the present Example, we did not observe significantly higher mRNA levels for these proteins in neutrophils from patients with IA. This may be because these proteins originate from sources other than neutrophils or may not be sufficiently unique to IA to be identified by our analysis.

One common trait of the previously-identified potential proteins markers, is that they are ubiquitous, being involved in a wide range of physiological and pathological functions. Thus, in addition to IA, they may also signify various vascular diseases. For example, serum VEGF is also increased during peripheral artery stenosis, plasma MCP-1 is also elevated in thromboembolic hypertension, and LPA is elevated in plasma of patients with vascular dementia. Perhaps for this reason, significant follow-up efforts have not been made towards subsequent biomarker development and validation on the basis of these studies.

An alternative approach to identifying potential biomarkers is to profile the transcriptome of the circulating blood, which affords screening for multitudes of potential markers and can provide insight into novel disease mechanisms that may be specific to IA. Recently, circulating RNA expression signatures of unruptured IAs were found in microarray studies. In IA patients, Jin et al. (Jin H, Li C, Ge H, Jiang Y, Li Y (2013) Circulating microRNA: a novel potential biomarker for early diagnosis of intracranial aneurysm rupture a case control study. J Transl Med 11: 296) found 77 differentially expressed plasma microRNAs that were involved in proliferation, apoptosis, molecular activation, transport, and differentiation; Li et al. (Li P, Zhang Q, Wu X, Yang X, Zhang Y, et al. (2014) Circulating microRNAs serve as novel biological markers for intracranial aneurysms. J Am Heart Assoc 3: e000972) discovered 119 differentially expressed plasma microRNAs related to inflammatory responses and connective tissue disorders; and Sabatino et al. (Sabatino G, Rigante L, Minella D, Novelli G, Della Pepa G M, et al. (2013) Transcriptional profile characterization for the identification of peripheral blood biomarkers in patients with cerebral aneurysms. J Biol Regul Homeost Agents 27: 729-738) identified 53 differentially expressed mRNAs from peripheral blood mononuclear cells that were related to increased cell proliferation and apoptosis. These findings indicate that IA is associated with altered expression of a large number of transcripts from various circulating blood components. As indicated, some Examples presented herein were conducted using next-generation RNA sequencing. This latest high-throughput technology affords two key advantages over microarrays used in previous investigations: (1) it offers a larger dynamic range, facilitating detection of expression differences in low-abundance transcripts; and (2) it avoids predetermined probes, allowing examination of novel RNAs (i.e., splice variants, non-coding RNAs, gene isoforms). These capabilities led us to discover a signature of 82 transcripts, containing several uncharacterized and/or non-coding RNAs, which cannot be detected on conventional microarrays. They include C21orf15, LOC100131289, FLJ27354, LOC100507387, LINC00482, C1orf226, and LOC730441. To our knowledge, these novel transcripts have not been associated with any other diseases.

We also designed the present approach to avoid common pitfalls of expression profiling studies. First, to avoid misclassification, we used DSA to confirm that the control subjects did not have aneurysms. Previous studies did not perform such imaging. Second, to find RNA expression differences due to the presence of an IA and not confounding factors, we paired the subjects by demographics and comorbidities. Previous studies typically used healthy subjects or spouses as controls. Third, we performed a replication study in an independent, unpaired cohort to investigate whether the signature can distinguish patients with IA in a general population. These measures helped to increase the likelihood that the discovered signature is associated with IA presence.

Circulating Neutrophils and Intracranial Aneurysms

Intracranial aneurysm natural history is characterized by mounting inflammatory responses and progressive degradation of the aneurysmal wall, starting from initial pro-inflammatory changes in smooth muscle cells that lead to overproduction of matrix metalloproteinases (MMPs). Once the aneurysmal pouch is formed, it harbors a hemodynamic environment conducive to macrophage and neutrophil infiltration into the wall, which is aided by a local increase of plasma chemokines and cytokines (IL-1β, IL-17, TNF-α) in the lumen. These inflammatory infiltrates massively produce MMPs to further degrade the aneurysm wall and advance its growth and rupture. This is evidenced by gene expression studies of human aneurysmal tissues, which found increased matrix degradation processes, inflammatory processes, and production of inflammatory cytokines and chemoattractant proteins in the IA wall. Furthermore, Yu et al. found that differences in DNA methylation in aneurysmal tissue act to promote inflammatory signaling through the NF-KB, JNK-STAT, and ERK/JNK pathways (Yu L, Wang J, Wang S, Zhang D, Zhao Y, et al. (2017) DNA Methylation Regulates Gene Expression in Intracranial Aneurysms. World Neurosurg 105: 28-36), uncovering a potential epigenetic underpinning to dysregulated inflammation during IA.

The role of neutrophils in IA pathophysiology may be complex and is not well understood. Besides secreting MMP-9, activated neutrophils also release NGAL and MPO, which indirectly contribute to extracellular matrix degradation and cytotoxicity, respectively. Increased NGAL in aneurysm tissue modulates the activity of MMP-9, protecting it from degradation and thus aiding aneurysm progression. Increased MPO, an inflammatory enzyme, elicits oxidative stress and pro-inflammatory cell signaling through production of reactive oxygen species. It has been observed that plasma levels of NGAL and MPO are increased in the blood of patients with aneurysms. Furthermore, both of these proteins can have autocrine effects that promote neutrophil activation, which could lead to expression changes observed in our study. Interestingly, we found significantly increased expression of SLC22A17, which is the NGAL receptor, in neutrophils from patients with IAs. This may reflect a possible interaction with circulating NGAL. However, we did not observe significantly higher levels of NGAL or MPO in circulating neutrophils, suggesting that these proteins may originate from the aneurysm sac itself, or other circulating cells.

Further analysis of the expression data described in this Example supports an association between activated circulating neutrophils and IA presence. Gene set enrichment analysis reveals that neutrophils from IA patients have higher levels of gene expression associated with leukocyte activation. This is evidenced by increased expression levels of several CD antigens from the "leukocyte activation" ontology (CD1D, CD7, CD86, and CD247) as well as CD177, a marker of neutrophil activation. IPA also reveals functions indicative of activated neutrophils, showing networks consistent with activation of cellular movement, cell-to-cell signaling, and cell proliferation. The fact that neutrophil expression data segregated aneurysms by size in PCA and MDS (FIGS. 3A and B) may indicate a correlation between the degree of IA advancement and neutrophil activation. The present disclosure thus indicates that peripheral neutrophil activation may play a role in IA development. Specifically, in this Example, we identified an IA-associated RNA expression signature of 82 transcripts in circulating neutrophils. This signature demonstrated a statistical power >0.80 and was able to distinguish patients with IAs from paired controls in several analyses. These transcripts also separated patients with IAs from unpaired controls in a small population.

Example 1,

S1 TABLE

Primers used for qPCR and their efficiencies.*

| Transcript | Primer Sequence | Annealing Temp. (° C.) | Eff. | PCR Prod. Length (bp) | SEQ ID NO |
|---|---|---|---|---|---|
| CD177 | 5'-ACACACGGAAACTTGGCTCA-3' | 60.0 | 1.04 | 124 | 1 |
|  | 5'-CCAGGGTTGATGTGAGTCCTAC-3' |  |  |  | 2 |
| NAAA | 5'-AACTTCGAAGCAGCTGTTGG-3' | 60.0 | 1.01 | 195 | 3 |
|  | 5'-TGGCTTCCAGTGGTCGTAAT-3' |  |  |  | 4 |
| SERPING1 | 5'-AGATCTTCCACAGCCCAGAC-3' | 60.0 | 0.94 | 104 | 5 |
|  | 5'-GGCGTCACTGTTGTTGCTTA-3' |  |  |  | 6 |
| GBP5 | 5'-TTGGGCATCACTCAGGCTAA-3' | 60.0 | 1.04 | 93 | 7 |
|  | 5'-CCCAGTTGAAAGCTGCACAT-3' |  |  |  | 8 |
| IL8 | 5'-CAGAGACAGCAGAGCACACA-3' | 60.0 | 1.07 | 70 | 9 |
|  | 5'-GTGAGATGGTTCCTTCCGGT-3' |  |  |  | 10 |
| GAPDH | 5'-CGCTCTCTGCTCCTCCTGTT-3' | 60.0 | 1.09 | 81 | 11 |
|  | 5'-CCATGGTGTCTGAGCGATGT-3' |  |  |  | 12 |

*Primers were selected using Primer3 and NCBI's Primer Blast. All efficiencies were within the range of 0.90-1.10. (bp = base pair, Eff = efficiency, Prod. = product, Temp. = temperature)

Example 1,

S2 TABLE

RNA Quality.*

| ID | Class | 260/280 | RIN |
|---|---|---|---|
| Discovery Cohort | | | |
| C1 | Control | 2.07 | 7.0 |
| C2 | Control | 2.02 | 7.4 |
| C3 | Control | 2.05 | 6.6 |
| C4 | Control | 1.92 | 6.5 |
| C5 | Control | 1.99 | 7.1 |
| C6 | Control | 2.08 | 7.1 |
| C7 | Control | 2.05 | 7.9 |
| C8 | Control | 1.96 | 6.7 |
| C9 | Control | 2.08 | 6.2 |
| C10 | Control | 2.04 | 7.3 |
| C11 | Control | 1.97 | 6.4 |
| A1 | Aneurysm | 2.04 | 7.8 |
| A2 | Aneurysm | 2.07 | 7.5 |
| A3 | Aneurysm | 2.06 | 8.1 |
| A4 | Aneurysm | 2.02 | 6.1 |
| A5 | Aneurysm | 2.03 | 7.3 |
| A6 | Aneurysm | 1.99 | 6.5 |
| A7 | Aneurysm | 2.02 | 7.5 |
| A8 | Aneurysm | 2.05 | 7.7 |
| A9 | Aneurysm | 2.07 | 6.0 |
| A10 | Aneurysm | 1.95 | 7.2 |
| A11 | Aneurysm | 1.97 | 6.9 |
| Replication Cohort | | | |
| C12 | Control | 2.03 | 6.0 |
| C13 | Control | 2.04 | 6.6 |
| C14 | Control | 2.05 | 6.0 |
| C15 | Control | 2.02 | 8.2 |
| C16 | Control | 2.04 | 6.0 |
| A12 | Aneurysm | 2.06 | 6.0 |
| A13 | Aneurysm | 1.97 | 6.4 |
| A14 | Aneurysm | 2.00 | 6.9 |
| A15 | Aneurysm | 1.96 | 7.4 |
| A16 | Aneurysm | 2.03 | 7.2 |

*The quality of the RNA samples was assessed by the 260/280 ratio and the RIN. (RIN = RNA integrity number)

Example 1,

S3 TABLE

Characteristics of 16 intracranial aneurysms in the group of 11 patients with IAs (3 patients had multiple intracranial aneurysms)* Example 1, S4 Table. RNA Sequencing Quality Control Analysis.*

| ID | IA Size (mm) | IA Location | Presence of Additional IAs | Family History of IA | Indications for DSA |
|---|---|---|---|---|---|
| A1 | 10 | VB junction | No | No | MRI for hand numbness indicated possible IA |
| A2 | 8 | Ophthalmic | No | No | Follow-up imaging of known IA |
| A3 | 4.5 | MCA | No | No | Incidental finding on CT indicated possible IA |
| A4 | 4 | Ophthalmic | Yes: +2 (1.5 mm and 3 mm ICA) | No | MRI for headache indicated possible IA |
| A5 | 10.8 | MCA | Yes: +2 (2.3 mm MCA, small AComA) | No | Incidental finding on MRI indicated possible IA |
| A6 | 9 | PComA | No | No | Follow-up of known IA |
| A7 | 5 | BT | No | No | MRA and CT for tremor revealed possible IA |
| A8 | 13 | ACA | No | Yes | MRI for decreased vision in left eye indicated possible IA |
| A9 | 19 | ICA | No | No | MRI for double vision indicated possible IA |
| A10 | 5 | ICA | Yes: +1 (3.5 mm ICA) | Yes | MRI for tremors indicated possible IA |
| A11 | 3 | BT | No | No | MRI for headache indicated possible IA |

*Aneurysm size ranged from 1.5 mm to 19 mm. Seven of 16 IAs (44%) were classified as small (greatest diameter <5 mm) and 9 (56%) were classified as large (greatest diameter ≥5 mm). The aneurysms were situated at various locations in the Circle of Willis, with most being around the internal carotid artery (ICA) and its branches. Two patients with IAs had a family history of the disease. In general, digital subtraction angiography was performed for either confirmation of IA presence after an incidental finding of IA on noninvasive imaging, or for follow-up imaging of a previously detected IA. (ACA = anterior cerebral artery, AComA = anterior communicating artery, BT = basilar terminus, CT = computed tomography, DSA = digital subtraction angiography, IA = intracranial aneurysm, ICA = internal carotid artery, MCA = middle cerebral artery, MRA = magnetic resonance angiography, MRI = magnetic resonance imaging, PComA = posterior communicating artery, VB = vertebrobasilar)

Example 1,

S4 TABLE

RNA Sequencing Quality Control Analysis.*

| ID | Class | M. Seqs. | Poor Qual. Seqs. | Seqs. Length | % GC | % Aligned | M. Aligned | Detected Transcripts |
|---|---|---|---|---|---|---|---|---|
| Discovery Cohort | | | | | | | | |
| C1 | Control | 27 | 0 | 51 | 48 | 96.50 | 24.8 | 17050 |
| C2 | Control | 59.3 | 0 | 51 | 49 | 96.50 | 54.4 | 17930 |
| C3 | Control | 35.9 | 0 | 51 | 49 | 94.90 | 32.3 | 18291 |
| C4 | Control | 68.9 | 0 | 51 | 49 | 96.60 | 63.3 | 18465 |
| C5 | Control | 53.3 | 0 | 51 | 50 | 95.80 | 48.5 | 17961 |
| C6 | Control | 80.3 | 0 | 51 | 50 | 96.30 | 73.5 | 18418 |
| C7 | Control | 97.4 | 0 | 51 | 50 | 96.00 | 88.9 | 18066 |
| C8 | Control | 67.8 | 0 | 51 | 49 | 96.40 | 62.2 | 18714 |
| C9 | Control | 36.2 | 0 | 51 | 49 | 96.10 | 33.2 | 17966 |
| C10 | Control | 79.3 | 0 | 51 | 49 | 96.80 | 72.7 | 17366 |
| C11 | Control | 89.1 | 0 | 51 | 50 | 95.70 | 81.1 | 18479 |
| A1 | Aneurysm | 48.1 | 0 | 51 | 49 | 96.90 | 44.5 | 18003 |
| A2 | Aneurysm | 35.7 | 0 | 51 | 48 | 96.80 | 32.9 | 17223 |
| A3 | Aneurysm | 60.4 | 0 | 51 | 49 | 96.90 | 55.9 | 18662 |
| A4 | Aneurysm | 55.9 | 0 | 51 | 49 | 96.90 | 51.4 | 18155 |
| A5 | Aneurysm | 61.3 | 0 | 51 | 49 | 97.20 | 56.9 | 17682 |
| A6 | Aneurysm | 23.4 | 0 | 51 | 49 | 95.90 | 21.4 | 17366 |
| A7 | Aneurysm | 35.8 | 0 | 51 | 49 | 96.40 | 32.3 | 18625 |
| A8 | Aneurysm | 26.9 | 0 | 51 | 50 | 97.10 | 24.9 | 16401 |
| A9 | Aneurysm | 29.1 | 0 | 51 | 50 | 96.60 | 26.8 | 17311 |
| A10 | Aneurysm | 59.5 | 0 | 51 | 49 | 96.00 | 54.1 | 18617 |
| A11 | Aneurysm | 14.6 | 0 | 51 | 49 | 95.00 | 13 | 17401 |
| Replication Cohort | | | | | | | | |
| C12 | Control | 74.4 | 0 | 51 | 50 | 95.10 | 66.8 | 18329 |
| C13 | Control | 66 | 0 | 51 | 50 | 95.50 | 60 | 18579 |
| C14 | Control | 58.5 | 0 | 51 | 51 | 95.50 | 53 | 18273 |
| C15 | Control | 64.3 | 0 | 51 | 51 | 94.90 | 57.9 | 18448 |
| C16 | Control | 47.3 | 0 | 51 | 50 | 95.30 | 42.7 | 18039 |
| A12 | Aneurysm | 42.2 | 0 | 51 | 51 | 95.50 | 38.3 | 17697 |
| A13 | Aneurysm | 75.3 | 0 | 51 | 51 | 95.90 | 68.6 | 18313 |
| A14 | Aneurysm | 64.9 | 0 | 51 | 50 | 96.60 | 59.5 | 17546 |

S4 TABLE-continued

RNA Sequencing Quality Control Analysis.*

| ID | Class | M. Seqs. | Poor Qual. Seqs. | Seqs. Length | % GC | % Aligned | M. Aligned | Detected Transcripts |
|---|---|---|---|---|---|---|---|---|
| A15 | Aneurysm | 39.8 | 0 | 51 | 50 | 97.40 | 36.8 | 18031 |
| A16 | Aneurysm | 42.1 | 0 | 51 | 50 | 95.20 | 38.2 | 17330 |

*The quality of the RNA sequencing experiments was measured. Overall, prior to alignment all samples had an average of 53.75M sequences. MultiQC reported that the sequencing experiments had an average of 49.09M mapped reads with a 96.13% read mapping rate, and detected an average of 17259 transcripts (transcripts with FPKM > 0). (Align. = alignment, M. = million, Seqs. = sequences, Qual. = quality)

Example 1,

S5 TABLE

Transcripts involved in the 4 networks constructed by Ingenuity Pathway Analysis (IPA).*

| Network | Molecules in Network | P-Score | Focus Molecules | Top Diseases and Functions |
|---|---|---|---|---|
| A | AKR1C3, Ap1, BCR (complex), CCL23, CD163, CXCL8, Collagen(s), DGKH, ERK1/2, FBN1, FCRL5, Fibrinogen, Gm-csf, ITGA7, IgG, IgG1, Immunoglobulin, Integrin, KIR2DS4 (includes others), KLRC2, Laminin, Mek, NOG, Nr1h, RCVRN, SERPINF2, SERPING1, SLC12A7, TCL1A, THBS1, Tgf beta, VLDLR, VWF, elastase, trypsin | 41 | 19 | Carbohydrate Metabolism, Cardiovascular System Development and Function, Cellular Movement |
| B | ADTRP, APP, B4GALNT3, CACHD1, CDHR2, ECI2, ETHE1, ETV7, FAM90A1, GBP5, GNPTAB, HPCA, HTR2C, IL10RA, KIAA1598, KLHL41, MAOA, MAOB, MY07B, MYPN, NEB, PPARA, PRSS21, PRUNE2, Ppap2a, RPL39L, RPL7L1, SCAMP5, SDC3, SRC, STYXL1, TMOD4, UBC, VWA8, XIRP2 | 30 | 15 | Cell-To-Cell Signaling and Interaction, Drug Metabolism, Energy Production |
| C | ADAMTS1, ADCY, AKR1C1/AKR1C2, AMPK, Akt, CYP4F2, Cg, EGR2, ERK, FADS2, FBXW8, FLT3, FSH, Focal adhesion kinase, G0S2, GNLY, Hdac, Hsp70, Hsp90, IL1, Insulin, KCNMA1, Lh, NRG1, PDGF BB, PID1, PTGDS, Pka, Pkc(s), Ras, SCT, SLC22A17, Vegf, caspase, p85 (pik3r) | 30 | 15 | Lipid Metabolism, Small Molecule Biochemistry, Behavior |
| D | AK5, AKR1C1/AKR1C2, ARFGAP3, ASS1, BATF2, C1R, C4BPA, CALB2, CAPG, CARD17, CCL23, CD177, CD276, CEBPA, CSF3, CTNNB1, CTNND2, Cebp, Collagen type VI, DACT1, DACT2, DACT3, DSPP, GPC4, HLA-F, HRK, IFNG, KLK8, LILRA2, OSM, PDCD1LG2, PRTN3, SLC16A1, VLDLR, WNT5A | 23 | 12 | Organismal Injury and Abnormalities, Tissue Morphology, Cellular Growth and Proliferation |

A table of the names of transcripts included in the top 4 networks derived from IPA, as well as the top diseases and functions of these transcripts. Neutrophil transcripts in bold were of the 82 differentially expressed transcripts between patients with and without IA (p-value < 0.05). Each network's p-score was derived from its p-value [p-score = −Log10 (p-value)] calculated by the Fisher's exact test. For a network with a p-score of 10, the odds of generating this network by chance alone is less than 1 out of $10^{10}$.

Example 1,

S6 TABLE

Clinical characteristics of the unpaired cohort of 5 patients with intracranial aneurysms and 5 control subjects without intracranial aneurysms (confirmed on imaging)*

|  | Patients with IA (n = 5) | Patients without IA (n = 5) |
|---|---|---|
| Age (years) (Mean ± SE) | 56.8 ± 3.95 | 48.8 ± 6.65 |
| Age (years) [Median (Q1/Q3)] | 56 (53/57) | 54 (51/55) |
| Sex |  |  |
| Female | 60% | 20% |
| Current smoker |  |  |
| Yes | 40% | 0% |
| Comorbidities |  |  |
| Hypertension | 40% | 40% |
| Hyperlipidemia | 20% | 20% |
| Heart disease | 20% | 0% |
| Previous stroke | 0% | 0% |
| Diabetes mellitus | 20% | 20% |
| Osteoarthritis | 20% | 20% |

*(IA = intracranial aneurysm, SE = standard error, Q = quartile)

Example 1,

S7 TABLE

Characteristics of 6 intracranial aneurysms in the replication group of 5 patients with IAs (one patients had multiple intracranial aneurysms)*

| IA Patient no. | IA Size (mm) | IA Location | Presence of Additional IAs | Family History of IA | Indications for DSA |
|---|---|---|---|---|---|
| 12 | 2 | ACA | No | No | Follow-up imaging of known IA |
| 13 | 1.4 | MCA | No | No | Incidental finding on MRI indicated possible IA |
| 14 | 3.7 | AComA | No | No | Incidental finding on CT for headache indicated possible IA |
| 15 | 7 | MCA | Yes: +1 (3.5 mm ACA) | No | Follow-up imaging of known IA |
| 16 | 3.9 | BT | no | No | Incidental finding on MRA for headache indicated possible IA |

*Aneurysm size ranged from 3.5 mm to 7 mm. Five of 6 IAs (83%) were classified as small (greatest diameter <5 mm) and 1 (17%) was classified as large (greatest diameter ≥5 mm). The aneurysms were situated at various locations in the Circle of Willis, with most being in the anterior vasculature (ACA and MCA). (ACA = anterior cerebral artery, AComA = anterior communicating artery, BT = basilar terminus, CT = computed tomography, DSA = digital subtraction angiography, IA, intracranial aneurysm, MCA = middle cerebral artery, MRA = magnetic resonance angiography, MRI = magnetic resonance imaging)

Example 2

This Example extends the disclosure of Example 1. In particular, in this Example, neutrophil RNA extracted from blood samples from 40 patients (20 with unruptured IA, 20 IA-free controls) was subjected to next-generation RNA sequencing to obtain neutrophil transcriptomes. In a randomly selected training cohort of 30 samples (n=15 with IA and n=15 controls), we performed differential expression analysis. Significantly differentially expressed transcripts (False Discovery Rate (FDR)<0.05, fold change of ≥1.5) were used to construct prediction models for IA using four known supervised machine learning approaches (linear discriminant analysis, k-nearest neighbors, nearest shrunken centroids, and support vector machines). These models were tested in the remaining 10 patients (testing cohort) and their performance was assessed by receiver-operating-characteristic curves. Real-time PCR was used to corroborate expression differences of 7 model transcripts in neutrophil samples from a new, independent cohort (n=10). The training cohort yielded 26 highly significantly differentially expressed neutrophil transcripts. Models using these transcripts identified IA patients in the testing cohort with accuracy ranging from 0.60 to 0.90. The best performing model was a diagonal linear discriminant analysis classifier (Area Under the Curve (AUC)=0.80 and accuracy=0.90). Six of seven differentially expressed genes were confirmed by quantitative PCR using isolated neutrophils from a separate patient cohort. Thus, this Example demonstrates use of machine learning methods to classify IA cases and create predictive models for unruptured IAs using circulating neutrophil transcriptome data.

The following materials and methods were used to produce the results described in this Example.

Cohort Generation

Study Population

This study was approved by the University at Buffalo Health Sciences Institutional Review Board. Methods were carried out in accordance with the approved protocol. Written informed consent was obtained from all subjects. 106 peripheral blood samples were collected from patients undergoing cerebral digital subtraction angiography (DSA) at Gates Vascular Institute in Buffalo, N.Y.: 51 patients had a positive IA diagnosis and 55 had a negative IA diagnosis (controls). Positive or negative IA diagnosis was confirmed by imaging, and patient medical records were collected.

Patients undergoing cerebral digital subtraction angiography (DSA) with positive and negative intracranial aneurysm (IA) diagnoses were enrolled in this study. Reasons for the patients to receive DSA included confirmation of findings from noninvasive imaging of the presence of IAs, vascular malformations, or carotid stenosis, or follow-up noninvasive imaging of previously detected IAs. All consenting patients were older than 18 years, were English speaking, and had not received previous treatment for IA. We excluded patients who potentially had altered immune systems; this included patients who were pregnant, had recently undergone invasive surgery, were undergoing chemotherapy, had a body temperature above 37.78° C. (100° F.), had received solid organ transplants, had autoimmune diseases, and those who were taking prednisone or any other immunomodulating drugs. Furthermore, included patients did not have any other known cerebrovascular malformations or extracranial aneurysms, including abdominal aortic aneurysms.

Neutrophil Isolation

Sixteen mL of blood was drawn from the access catheter in the femoral artery and transferred into two 8 mL, citrated, cell preparation tubes (BD, Franklin Lakes, N.J.). Neutrophils were isolated within 1 hour of peripheral blood collection, as described elsewhere (Jiang K, Sun X, Chen Y, Shen Y, Jarvis J N (2015) RNA sequencing from human neutrophils reveals distinct transcriptional differences associated with chronic inflammatory states. BMC Med Genomics 8:55). Cell preparation tubes were centrifuged at 1,700×g for 25 minutes to separate erythrocytes and neutrophils from mononuclear cells and plasma in the peripheral blood samples via a Ficoll density gradient. Erythrocytes and neutrophils were collected into a 3 mL syringe. Following hypotonic lysis of red blood cells, neutrophils were isolated by centrifugation at 400×g for 10 min and disrupted and stored in TRIzol reagent (Life Technologies, Carlsbad, Calif.) at −80° C. until further processing. Neutrophils isolated in this fashion are more than 98% CD66b+ by flow cytometry and contain no contaminating CD14+ monocytes. (Jarvis J N, Dozmorov I, Jiang K, Frank M B, Szodoray P, et al. (2004) Novel approaches to gene expression analysis of active polyarticular juvenile rheumatoid arthritis. Arthritis Res Ther 6: R15-r32.)

RNA Preparation

Neutrophil RNA was extracted using TRIzol, according to the manufacturer's instructions. Trace DNA was removed by DNase I (Life Technologies, Carlsbad, Calif.) treatment. RNA was purified using the RNeasy MinElute Cleanup Kit (Qiagen, Venlo, Limburg, Netherlands) and suspended in RNase-free water. The purity and concentration of RNA in each sample was measured by absorbance at 260 nm on a NanoDrop 2000 (Thermo Scientific, Waltham, Mass.), and 200-400 ng of RNA was sent to our university's Next-Generation Sequencing and Expression Analysis Core facility for further quality control. Precise RNA concentration was measured at the core facility via the Quant-iT RiboGreen Assay (Invitrogen, Carlsbad, Calif.) with a TBS-380 Fluorometer (Promega, Madison, Wis.), whereas the quality of the RNA samples was measured with an Agilent 2100 BioAnalyzer RNA 6000 Pico Chip (Agilent, Las Vegas, Nev.). RNA samples of acceptable purity (260/280 ratio of $\geq 1.9$) and integrity (RIN$\geq$5.0) were considered for RNA sequencing.

RNA Sequencing

RNA Libraries were Constructed using the Illuminal TruSeq RNA Library

Preparation Kit (Illumina, San Diego, Calif.). All samples were subjected to 50-cycle, single-read sequencing in the HiSeq2500 (Illumina) and were demultiplexed using Bcl2Fastq v2.17.1.14 (Illumina). Gene expression analysis was carried out using the Tuxedo Suite. For each sample, short RNA fragment data in the FASTQ format was compiled and aligned to the human reference genome (human genome 19-hg19) using TopHat v2.1.13. To evaluate the quality of RNA sequencing, we performed quality control analysis using FASTQC and visualized and compared the aggregate quality control data using MultiQC.

Transcript expression levels were calculated from counts using Transcripts Per Million (TPM) normalization for comparison of RNA levels between samples. Samples were processed in two batches. Therefore, we performed batch effect correction using ComBat under the default settings in R. This was performed on expression data for all transcripts with an average TPM>1.0 in at least one of the two groups. (See Example 2, Supplemental Table 1 for batch information).

Differential Expression Analysis

Prior to differential expression analysis, neutrophil transcriptomes were randomly divided into two cohorts: a training cohort (n=30) and a testing cohort (n=10), each containing half IA and half control transcriptomes. Differential gene expression analysis in the training cohort was carried out using F statistics to assess differential variation about the mean on a transcript-by-transcript basis. Multiple testing correction was performed by using the Benjamini-Hochberg method, and q-values were reported for each transcript. Transcripts were considered significantly differentially expressed at an FDR-adjusted p-value (q-value) <0.05.

Bioinformatics

We performed gene ontology term enrichment analysis using the open source Gene Ontology enRIchment anaLysis and visuaLizAtion tool (GORILLA) on all differentially expressed transcripts (q<0.05). This was done using a background gene list of neutrophil RNA expression (average fragments per kilo base of transcript per million (FPKM) mapped reads, FPKM>1.0) of 3 healthy individuals, described elsewhere. (Jiang K, Sun X, Chen Y, Shen Y, Jarvis J N (2015) RNA sequencing from human neutrophils reveals distinct transcriptional differences associated with chronic inflammatory states. BMC Med Genomics 8: 55.) This tool identified gene ontology (GO) terms that are enriched in genes with increased or decreased expression in IA compared to the background neutrophil expression using standard hyper geometric statistics. Associated gene ontology processes and functions were reported if the enrichment FDR adjusted p-value (q-value)<0.20 (20% FDR).

Classification Model Development

Feature Selection

Prior to model training, the set of differentially expressed transcripts was reduced by filtering. We retaining only transcripts with an FDR<0.05 and absolute fold-change $\geq$1.5. To visualize how the remaining transcripts separated IA from control samples, we performed principal component analysis (PCA) in R using the prcomp package under the default settings.

Model Training

Using the selected transcripts, we trained classification models using MATLAB Statistics and Machine Learning Toolbox and R bioconductor. Specifically, we considered four algorithms that have been successfully used for disease classification from gene expression data. These methods included K-Nearest Neighbors Classification, (Baker C J, Fiore A, Connolly E S, Jr., Baker K Z, Solomon R A (1995) Serum elastase and alpha-1-antitrypsin levels in patients with ruptured and unruptured cerebral aneurysms. Neurosurgery 37: 56-61; discussion 61-5) Linear Discriminant Analysis, (Phillips J, Roberts G, Bolger C, el Baghdady A, Bouchier-Hayes D, et al. (1997) Lipoprotein (a): a potential biological marker for unruptured intracranial aneurysms. Neurosurgery 40: 1112-1115; discussion 1115-1117), Nearest Centroids Classification, (Sandalcioglu I E, Wende D, Eggert A, Regel J P, Stolke D, et al. (2006) VEGF plasma levels in non-ruptured intracranial aneurysms. Neurosurg Rev 29: 26-29), and Support Vector Machines (SVM). (Zhang H F, Zhao M G, Liang G B, Song Z Q, Li ZQ (2013) Expression of pro-inflammatory cytokines and the risk of intracranial aneurysm. Inflammation 36: 1195-1200). Each method was applied to the training cohort separately and evaluated with a leave-one-out (LOO) cross-validation to estimate model performance and prevent overfitting. Nearest neighbors classification: The k-nearest neighbors method (Chalouhi N, Theofanis T, Starke R M, Zanaty M, Jabbour P, et al. (2015) Potential role of granulocyte-monocyte colony-stimulating factor in the progression of intracranial aneurysms. DNA Cell Biol 34: 78-8) with a cosine metric (Cosine Nearest Neighbors (cosine NN)) was employed.

The number of neighbors, k, was set as 5 for cosine NN. The resulting model classified test samples by calculating their distance to each training sample. The test samples' labels were predicted by majority vote, choosing the class that was most common among their k nearest neighbors. Linear discriminant analysis: We trained a classifier using diagonal linear discriminant analysis (DLDA) as described elsewhere. (Baker C J, Fiore A, Connolly E S, Jr., Baker K Z, Solomon R A (1995) Serum elastase and alpha-1-antitrypsin levels in patients with ruptured and unruptured cerebral aneurysms. Neurosurgery 37: 56-61; discussion 61-52). This method seeks the linear combination of transcripts which best separate two classes using a diagonal covariance matrix. The linear model coefficients associated with transcripts (discriminant scores) relayed importance of each transcript to the prediction model. (Chen J, Han L, Xu X, Tang H, Wang H, et al. (2015) Serum biomarkers VEGF-C and IL-6 are associated with severe human Peripheral Artery Stenosis. J Inflamm (Lond) 12: 50). Classification was performed by projecting a test sample onto the maximally separating direction which was determined by discriminant scores and calculating the corresponding posterior probability of IA. Nearest centroids classification: We used a modification of the nearest centroids technique, called Nearest Shrunken Centroids (NSC). (Sandalcioglu I E, Wende D, Eggert A, Regel J P, Stolke D, et al. (2006) VEGF plasma levels in non-ruptured intracranial aneurysms. Neurosurg Rev 29: 26-29). This method calculates class-specific centroids (standard deviation normalized averages) for each transcript and refined them by eliminating those with variable expression. Classification was performed by comparing the expression of the included model transcripts with the centroids of the two classes and assigning it to a class that is closest to in squared distance. (Sandalcioglu I E, Wende D, Eggert A, Regel J P, Stolke D, et al. (2006) VEGF plasma levels in non-ruptured intracranial aneurysms. Neurosurg Rev 29: 26-29). Support vector machine: The most complex classification algorithm we implemented was SVM. (Kimura H, Okada O, Tanabe N, Tanaka Y, Terai M, et al. (2001) Plasma monocyte chemoattractant protein-1 and pulmonary vascular resistance in chronic thromboembolic pulmonary hypertension. Am J Respir Crit Care Med 164: 319-324). To separate the binary labeled training samples, SVM finds a hyper-plane which is maximally distant from samples of either class. A linear kernel was used in model creation. The resulting model classified test samples by mapping them to a higher-dimensional space and making decisions based on their signed distance to the hyper-plane.

Classification Model Evaluation

Model Assessment in the Training Cohort

The performance of each model in the training cohort was estimated using the results of the LOO cross-validation. The model classifications were compared to each patient's clinical diagnosis from imaging, and the true positives (TP), true negatives (TN), false positives (FP), and false negatives (FN) were counted. Each model's performance was first assessed by calculating the model's sensitivity, specificity, and accuracy:

$$\text{Sensitivity} = TP/(TP+FN)$$
$$\text{Specificity} = \frac{TN}{TN+FP}$$
$$\text{Accuracy} = (TP+TN)/(TP+FP+FN+TN)$$

Based on model predictions, we created receiver operating characteristic (ROC) curves and calculated the area under the ROC curve (AUC) to assess model performance.

Validation of the Models in an Independent Testing Cohort

Classification models were independently tested on transcriptomes from the testing cohort. TPM values of these model features were input into the models for classification of IA presence. The classification results were compared to clinical diagnoses to calculate the true sensitivity, specificity, and accuracy for each model. ROC curves were constructed and AUCs were used to assess the performance of each classifier.

Cross-Validation Over All Samples

Since the models were fit using data points from a randomly selected training dataset (n=30), selection bias may introduce inconsistency in model predictions. To increase the models' reliability of prediction and to create algorithms more generalizable to the entire population, we implemented a LOO cross-validation using the expression levels of the 26 selected transcripts from all 40 patients for each model. This essentially retrained the models in 40 different training sets consisting of 39 samples and performed testing on the remaining sample. As before, classification results were used to calculate the sensitivity, specificity, and accuracy for each model, as well as find the AUC of the ROC curve for each modified classifier.

Positive and Negative Predictive Values of the Models

We further assessed the predictive value of the classification models by calculating their positive predictive values (PPV) and negative predictive values (NPV). (Li P, Zhang Q, Wu X, Yang X, Zhang Y, et al. (2014) Circulating microRNAs serve as novel biological markers for intracranial aneurysms. J Am Heart Assoc 3: e000972), PPVs and NPVs were estimated using the following formulas based on the Bayes' theorem:

$$PPV = \frac{\text{Sensitivity} \times \text{Prevalence}}{\text{Sensitivity} \times \text{Prevalence} + (1-\text{Specificity}) \times (1-\text{Prevalence})}$$

$$NPV = \frac{\text{Specificity} \times (1-\text{Prevalence})}{(1-\text{Sensitivity}) \times \text{Prevalence} + \text{Specificity} \times (1-\text{Prevalence})}$$

The PPV and NPV were calculated over a range of prevalence from 0-100%, noting the reported range of IA prevalence (3.2%-7%) according to established approaches: (Meng H, Tutino V M, Xiang J, Siddiqui A (2014) High WSS or low WSS? Complex interactions of hemodynamics with intracranial aneurysm initiation, growth, and rupture: toward a unifying hypothesis. AJNR Am J Neuroradiol 35: 1254-1262; Chalouhi N, Points L, Pierce G L, Ballas Z, Jabbour P, et al. (2013) Localized increase of chemokines in the lumen of human cerebral aneurysms. Stroke 44: 2594-2597; Frosen J, Tulamo R, Paetau A, Laaksamo E, Korja M, et al. (2012) Saccular intracranial aneurysm: pathology and mechanisms. Acta Neuropathol 123: 773-786; Yu L, Wang J, Wang S, Zhang D, Zhao Y, et al. (2017) DNA Methylation Regulates Gene Expression in Intracranial Aneurysms. World Neurosurg 105: 28-36).

Validation of Expression Differences by qPCR in an Independent Cohort

To validate expression differences in the 26 model genes, quantitative polymerase chain reaction (qPCR) was performed. Due to limitations in mRNA volume, qPCR was performed on 7 model transcripts in 10 additional patients (5 with IA and 5 controls), as described in Example 1. In brief, oligonucleotide primers were designed with a 60° C. melting temperature and a length of 15-25 nucleotides to produce PCR products with lengths of 50-250 base pairs using Primer3 software and Primer BLAST (NCBI, Bethesda, Md.). The replication efficiency of each primer set was tested by performing qPCR on serial dilutions of cDNA samples (primer sequences, annealing temperatures, efficiencies, and product lengths are shown in Example 2, Supplemental Table 2).

For reverse transcription, first-strand cDNA was generated from total RNA using OmniScript Reverse Transcriptase kit (Qiagen, Venlo, Limburg, Netherlands) according to the manufacturer's directions. Quantitative PCR was run with 10 ng of cDNA in 25 µL reactions in triplicate in the Bio-Rad CFX Connect (Bio-Rad, Hercules, Calif.) using ABI SYBR Green I Master Mix (Applied Biosystems, Foster City, Calif.) and gene-specific primers at a concentration of 0.02 µM each. The temperature profile consisted of an initial step of 95° C. for 10 min, followed by 40 cycles of 95° C. for 15 seconds and 60° C. for 1 min, and then a final melting curve analysis from 60° C. to 95° C. over 20 min.

Gene-specific amplification was demonstrated by a single peak using the Bio-Rad dissociation melt curve. Samples were normalized based on GAPDH, 18s rRNA, and GPI expression, which was run in parallel reactions to the genes of interest. These values were used to calculate average fold-change between the two groups using the $2^{-\Delta\Delta Ct}$ method. (Leopold J A (2015) The Central Role of Neutrophil Gelatinase-Associated Lipocalin in Cardiovascular Fibrosis. Hypertension 66: 20-22). These values were calculated for each housekeeping gene and averaged. Average fold-change in gene expression measured by qPCR data in the new cohort was then compared to the fold-change calculated from RNA sequencing in the training cohort.

The following results were obtained using the foregoing materials and methods described in this Example.

Study Participants

During the study period, we collected 106 blood samples (51 from patients with IA, 55 from control subjects) as well as angiographic images and medical records data from individuals undergoing cerebral digital subtraction angiography (DSA). Of the blood samples collected, 43 (20 from IA patients, 23 from controls) met our criteria and also had neutrophil RNA of sufficient quality and volume for sequencing. A total of forty patients (20 with IA and 20 controls) were then chosen and randomly divided into a 30 patient training cohort (n=15 IA and n=15 control) and a 10 patient testing cohort (n=5 IA and n=5 control). See Example 2, Table 1 for the characteristics of the two cohorts. These samples were of sufficient quality and had an average 260/280 of 2.02 (range 1.90-2.12) and an average RNA integrity number (RIN) of 6.88 (range 5.2-8.2) (Example 2, Supplemental Table 3). Patients with IAs had aneurysms ranging in size from 1-19 mm and included 5 individuals with multiple IAs (see Example 2, Supplemental Table 4). A portion of these samples (n=22) were described in Example 1, which analyzed neutrophil expression differences between patients with and without IA.

Differential RNA Expression in Neutrophils from Patients with IA vs. Control

Figure 7:
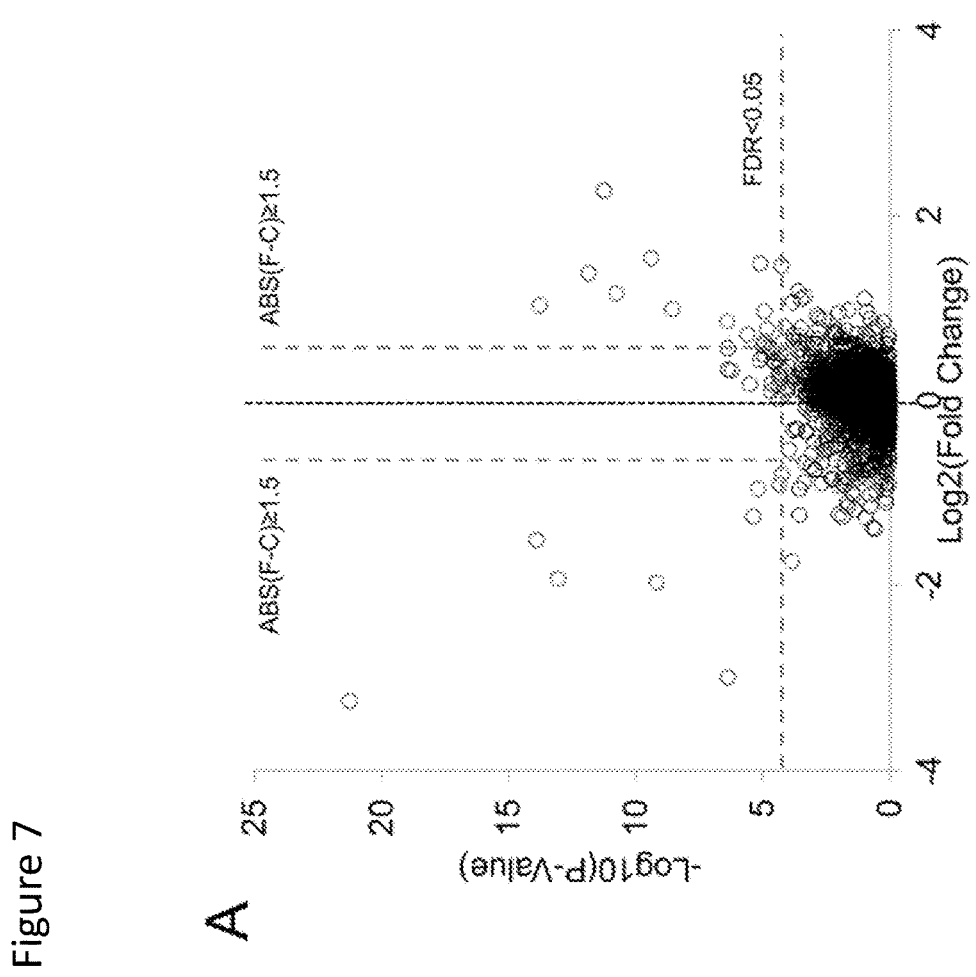
FIG. 7: Neutrophil RNA expression differences between patients with IA and IA-free controls and feature selection for classification model creation. (A) Transcriptome profiling demonstrated 95 differently expressed transcripts (q-value<0.05) between patients with intracranial aneurysm (IA) and controls. Of these, 26 had an FDR<0.05 and an absolute fold change $\geq 1.5$ (in grey). (B) Principal component analysis (PCA) using these 26 transcripts demonstrated general separation between patients with IA (dark filled dots—60% circled labeled "IA") and controls (white dots—80% circled labeled "control"). (C) Estimation of model performance during LOO cross-validation in the training cohort demonstrated that most models performed with an accuracy of 0.50-0.73. Overall Diagonal Linear Discriminant Analysis (DLDA) had the highest combination of sensitivity, specificity, and accuracy (0.67, 0.80, 0.73). (D) Receiver Operator Characteristic (ROC) analysis using classifications in the training dataset demonstrated that the models had Area Under the Curve (AUC) of 0.54 (SVM) to 0.72 (DLDA).
Figure 7:
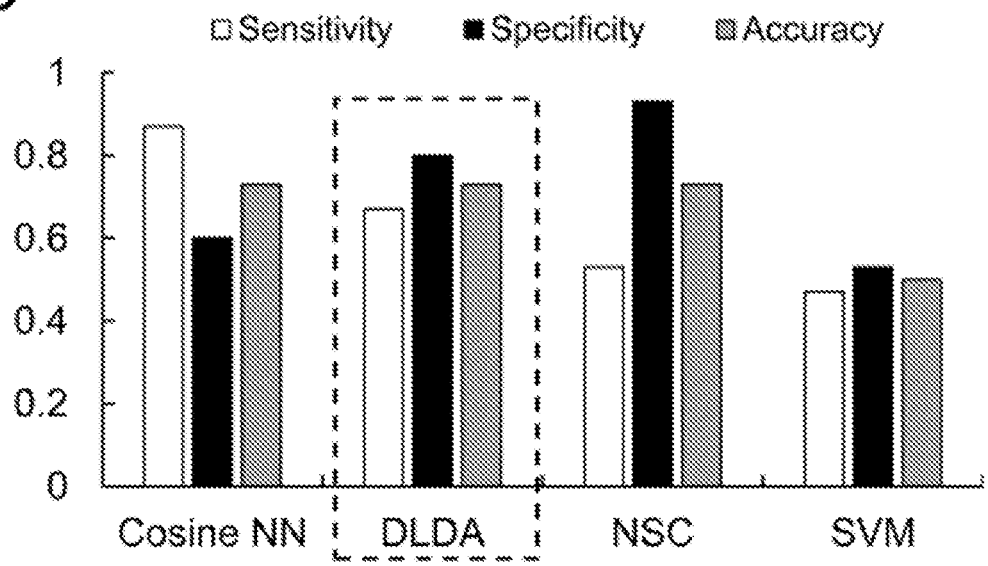
Figure 7:
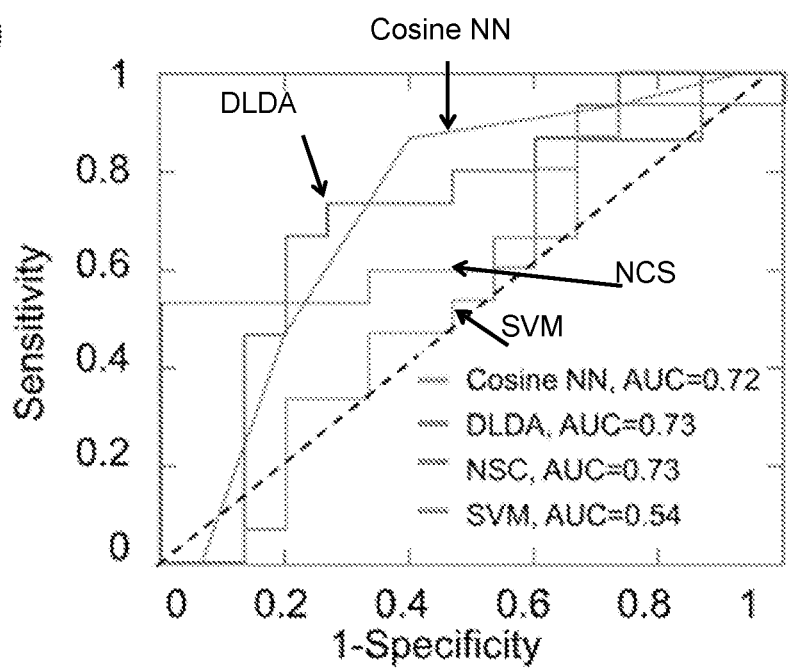

RNA sequencing data was used to identify differentially expressed neutrophil transcripts between the 15 patients with IA and 15 controls in the training cohort. Overall, our sequencing experiments had an average of 53.84 million sequences per sample and a 95.4% read mapping rate (% aligned) (see Example 2, Supplemental Table 5). The volcano plot in FIG. 7A shows neutrophil expression differences between IA patients and controls in terms of average fold-change in expression and significance level. From 12,775 transcripts with average TPM>1.0 in either group, differential expression analysis identified 95 transcripts that were significantly differentially expressed (q<0.05). Gene set enrichment analysis performed using these 95 differentially expressed transcripts showed genes with higher levels in the IA group were involved in defense response, leukocyte activation, stem cell maintenance, maintenance of cell number, cell activation, and stem cell development. Genes with lower levels in IAs were involved in regulation of glutathione and tetrapyrrole binding (Example 2, Table 2).

Selected Transcripts for Model Training

Prior to model training, we performed feature selection by filtering to identify disease-related transcripts and reduce the data dimensionality to facilitate downstream analysis. Our statistical criteria of false discovery rate (FDR)<0.05 and an absolute fold-change≥1.5 resulted in retention of the 26 transcripts that are demonstrated in shading in FIG. 7A and listed in Example 2, Table 3. The PCA in FIG. 7B shows that these 26 transcripts could generally discriminate patients with IAs from the controls. The top three principal components represented 47.8% of the variation; PC1 contained 22.4% variation, PC2 contained 15.3% variation, and PC3 contained 10.1% variation. Overall, 60% of the aneurysm samples and 80% of the control samples could be grouped together by PCA.

Classification Models of IA Have High Performance in Training and Testing Datasets Using the expression of these 26 transcripts, we trained four classification models, using cosine nearest neighbors (cosine NN), diagonal linear discriminant analysis (DLDA), nearest shrunken centroids (NSC), and support vector machines (SVM). FIG. 7C shows the sensitivity, specificity, and accuracy of the models, which were estimated from LOO cross-validation. There was moderate performance by each classification method, with accuracies that ranged from 0.50 to 0.73. Evaluation by ROC curve analysis showed a range in AUCs from 0.54 to 0.72 (FIG. 7D) across all methods. In this dataset, DLDA performed the best, with a sensitivity of 0.67, a specificity of 0.80, an accuracy of 0.73, and an AUC of 0.72.

Figure 8:
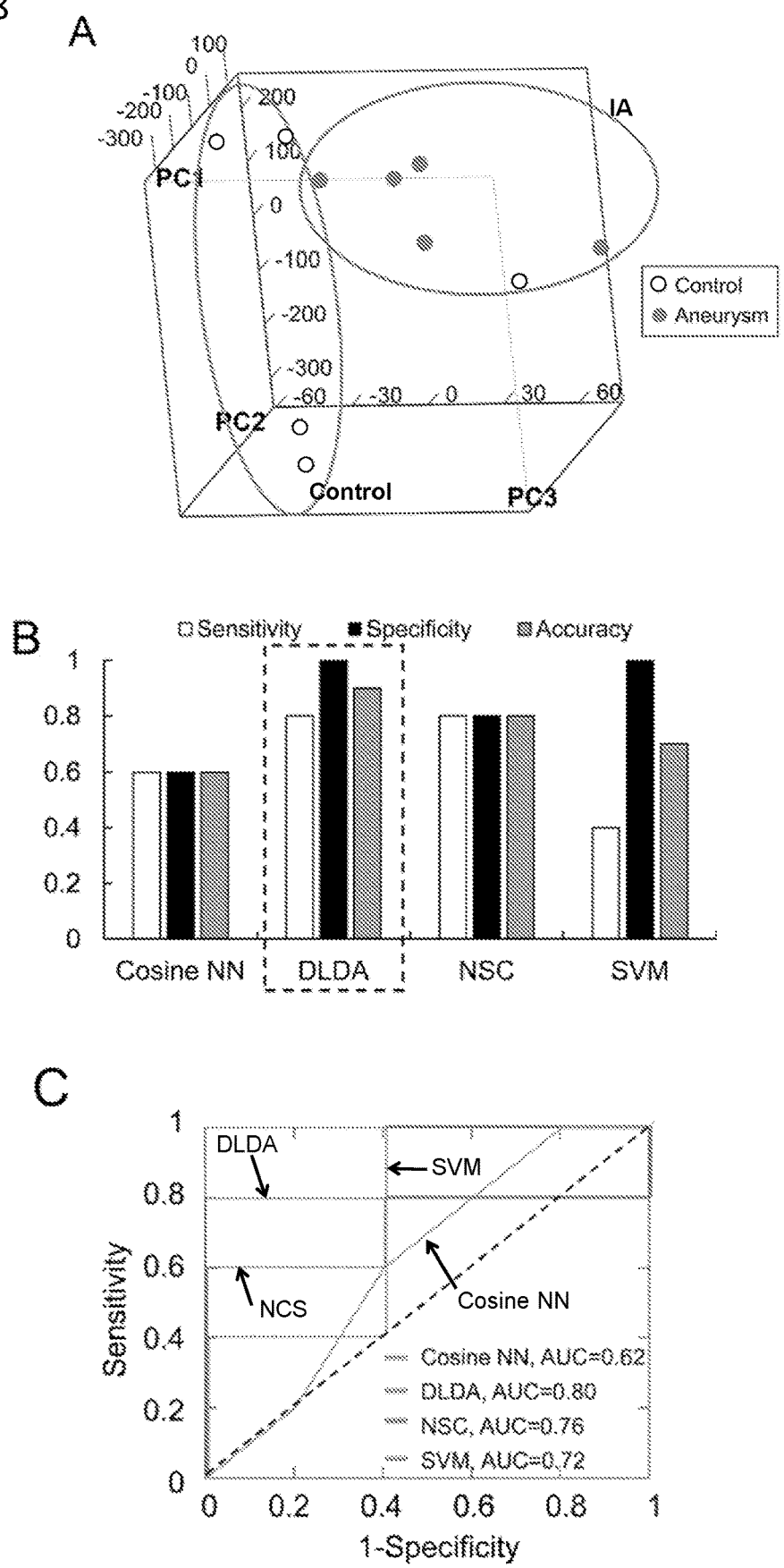
FIG. 8: Performance of the 4 classification models during model training and testing. (A) Principal component analysis using the 26 transcripts demonstrated general separation between patients with IA (dark filled dots—100% circled labeled "IA") and controls (white dots—80% circled labeled "control"). (B) Validation of the classification models in an independent testing cohort of patients demonstrated that DLDA had the best performance, with sensitivity, specificity, and accuracy of 0.80, 1.0, and 0.90, respectively. (C) ROC analysis in the testing cohort demonstrated that DLDA also had the best AUC (0.80).

To independently validate the models, we implemented them in the testing cohort neutrophil transcriptomes from 10 patients. The PCA in FIG. 8A shows that the 26 transcripts could discriminate patients with IAs from controls in the testing cohort as well. Overall, 100% of the aneurysm samples and 80% of the control samples could be grouped together by PCA. In the testing cohort, the models predicted the aneurysm status with a range in accuracy from 0.60 to 0.90 (FIG. 8B). The ROC analysis in FIG. 8C demonstrates that the models' AUCs ranged from 0.62 to 0.80. In this cohort, the DLDA classification model again performed the best, with a sensitivity of 0.80, specificity of 1.0, an accuracy of 0.90, and an AUC of 0.80.

Cross-Validation to Increase Model Reliability

Figure 9:
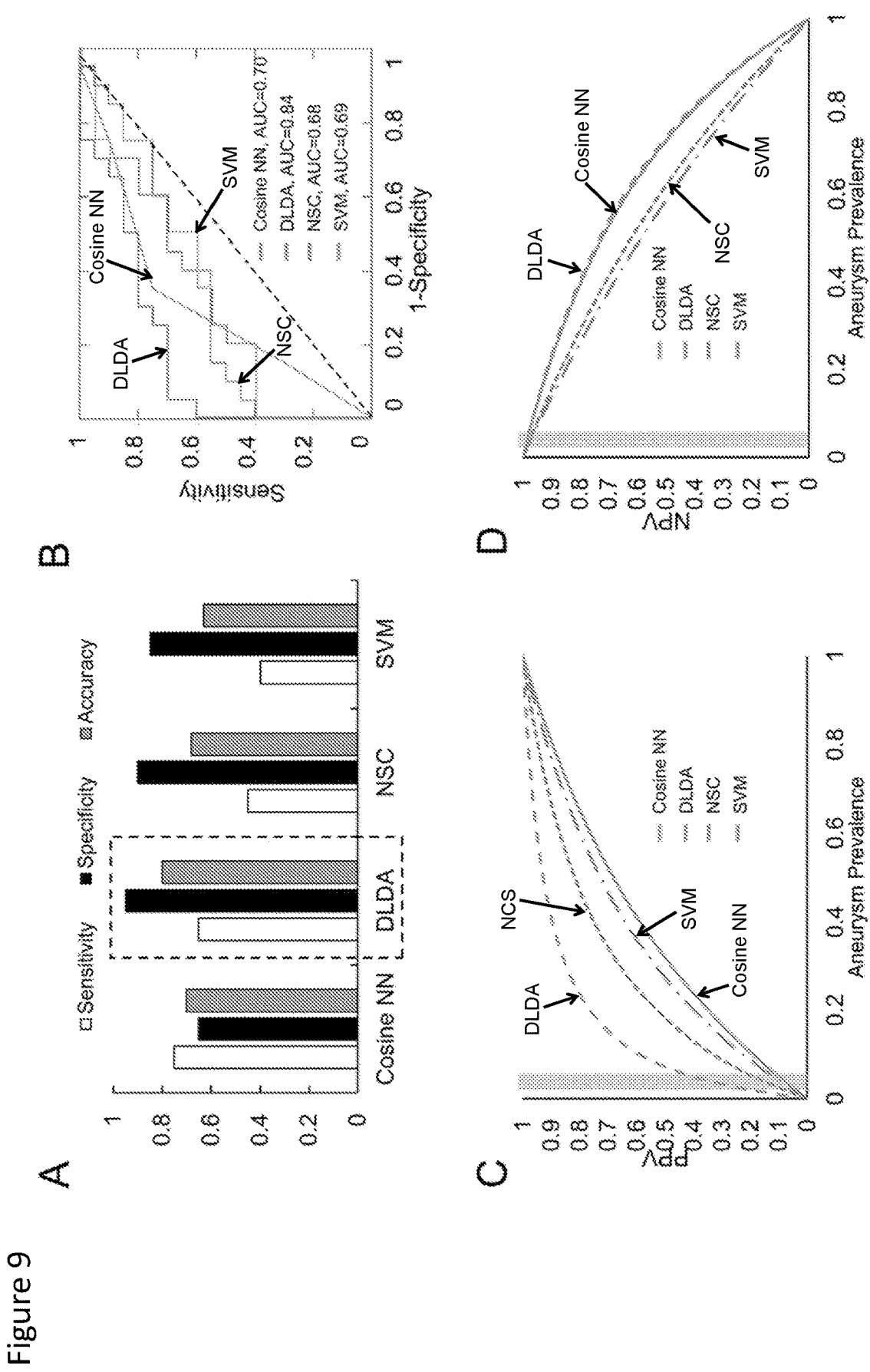
FIG. 9: Assessment of the model performance by LOO cross-validation over all data, and positive predictive value (PPV)/Negative Predictive Value (NPV). (A) Estimation of model performance showed that the models performed with an accuracy of 0.63-0.80. DLDA had the highest combination of sensitivity, specificity, and accuracy (0.65, 0.95, 0.80). (B) ROC analysis demonstrated that the models had AUC of 0.68 (Nearest Shrunken Centroids (NSC)) to 0.84 (DLDA). (C) The positive predictive value of all models across all possible prevalence. The best performing model (DLDA) had the highest PPV, and Support Vector Machines (SVM) demonstrated poorest PPV. (D) The DLDA models also had the best NPV, but only slightly better than that of the cosine NN, NSC, and SVM.

To increase the models' reliability, we employed LOO cross-validation using all patient transcriptomes and refit them in all 40 datasets (all combinations of 39 training samples and 1 testing sample). This analysis revealed the models' accuracy ranged from 0.63 to 0.80 (FIG. 9A) and their AUCs ranged from 0.69 to 0.84 (FIG. 9B). Again, the DLDA model performed the best, with a sensitivity of 0.65, specificity of 0.95, accuracy of 0.80, and an AUC of 0.84.

Models Have High Negative Predictive Value

Given their range of performance, we wanted to know how useful the models would be at detecting IA. Their value, however, would be inherently influenced by the prevalence of IA in a given target population. To estimate this, we plotted the positive predictive value (PPV) and negative predictive value (NPV) for each model (FIGS. 9C and D) using the sensitivity and specificity reported after the LOO cross-validation in all datasets. The rate aneurysm incidence found in the published literature ranged from 3.2% (Meng H, Tutino V M, Xiang J, Siddiqui A (2014) High WSS or low WSS? Complex interactions of hemodynamics with intracranial aneurysm initiation, growth, and rupture: toward a unifying hypothesis. AJNR Am J Neuroradiol 35: 1254-1262) to 7%, (Chalouhi N, Points L, Pierce G L, Ballas Z, Jabbour P, et al. (2013) Localized increase of chemokines in the lumen of human cerebral aneurysms. Stroke 44: 2594-2597) and is indicated as shown on the graph. At a 5% incidence of aneurysm, the models' PPV ranged from 0.10 to 0.41 and NPV ranged from 0.96 to 0.98. The DLDA classifier had the highest PPV (0.41) and NPV (0.98).

Independent Validation of Expression Differences by RT-qPCR

Figure 10:
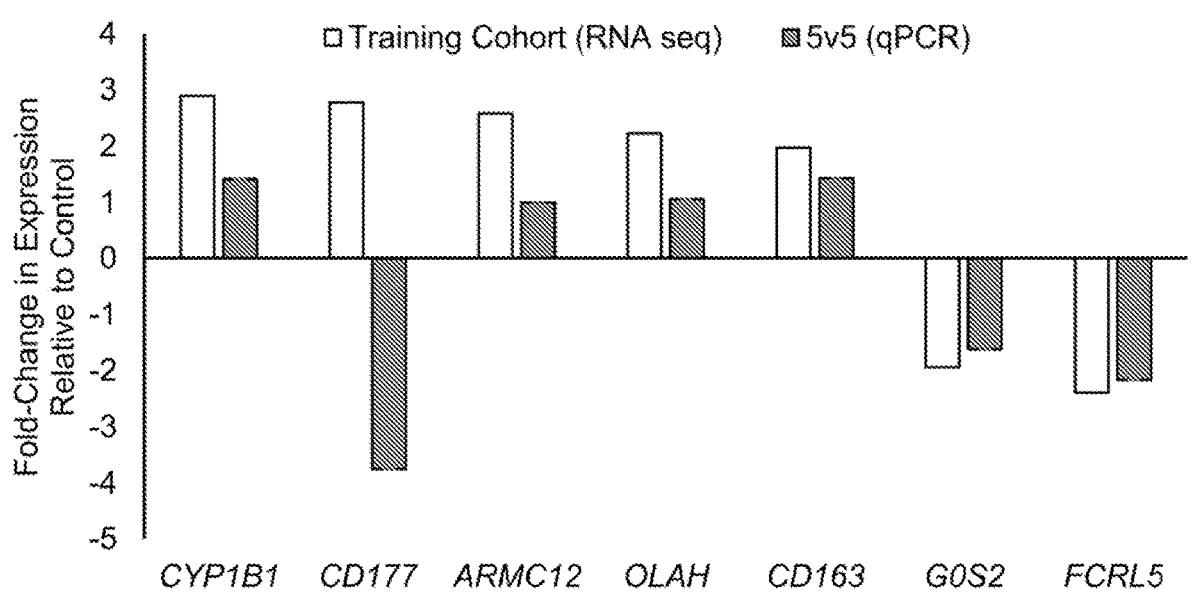
FIG. 10: Validation of RNA-Seq data for 7 transcripts by Quantitative Polymerase Chain Reaction (qPCR). Six of seven differentially expressed transcripts in patients with and without IA were also differentially expressed in neutrophils in the qPCR in an independent cohort.

We performed a corroboration study to determine if the differential expression of 7 model genes could be detected in a new population of IA and control patients. We used samples from 10 additional patients (5 with IA and 5 controls) from which we collected neutrophil RNA but did not sequence (see Example 2, Supplemental Table 6 for patient information for this cohort and Example 2, Supplemental Table 7 for aneurysm information from the IA patients in this cohort). These samples were used for quantitative polymerase chain reaction (qPCR) analysis differentially of CD177, CYP1B1, ARMC12, OLAH, CD163, G0S2, and FCRL5, which were selected because they were also expressed as described in Example 1. FIG. 10 shows the qPCR results of this corroborative study in comparison with expression differences obtained from RNA sequencing in the training cohort. Six of the 7 genes demonstrated average fold-change in the same direction and of similar magnitude to those in the original cohort. This indicated that the difference in expression of these transcripts between patients with IA and control is consistent.

It will be recognized from the foregoing description in this Example that Neutrophils play a role in the progressive inflammation that typifies IAs. Therefore, we analyzed whether gene expression patterns in circulating neutrophils could reflect the presence of the disease. As described in Example 1, we found that patients with unruptured IAs and aneurysm-free controls had significant RNA expression differences in circulating neutrophils. In this Example, we analyzed biomarkers using neutrophil RNA expression levels from blood samples to predict IA presence. We used RNA expression profiling in circulating neutrophils to identify 26 transcripts that were highly associated with the presence of IA. Machine learning algorithms were then implemented to develop classification models that used these 26 transcripts to predict the presence of aneurysm.

Classification Models of IA

Without intending to be constrained by any particular theory, it is believed this disclosure is the first to demonstrate IA prediction from RNA expression patterns in the blood. The four models we trained performed with an average classification accuracy of 80%, a level which indicates promise for further investigation of RNA expression biomarkers for IA. Overall, classification by DLDA achieved the best performance in our data. This model, consistently had the highest accuracy and AUC over multiple analyses, including cross-validation during model training (accuracy=0.73, AUC=0.72), independent model validation (accuracy=0.90, AUC=0.80) and cross-validation across the entire dataset (accuracy=0.80, AUC=0.84). See Example 2, Supplemental Table 8 for a detailed summary of the performance of all models.

The DLDA classifier may have performed better than other methods because it accommodated inter-sample variability in the 26 transcripts. While average expression of each transcript is significantly different between IA and controls, their expression levels may vary between individuals, and thus modeling techniques that broadly survey patterns of gene expression may afford better IA classification. Without intending to be constrained by any particular theory, it is considered that the DLDA method may have functioned as described herein because: (1) it ranks transcripts by importance, giving more weight to the most consistently informative transcripts (unlike non-parametric approaches such as nearest neighbors). And (2) it uses information from all transcripts to project test samples to the direction which best separate the classes. Thus, a linear combination of transcripts can generate a stable IA prediction, and accommodate for inter-sample variability. Additionally, ignoring correlations between genes as DLDA does, can provide a simple model and produced lower misclassification rates than more sophisticated classifiers, such as SVM.

In this disclosure, classifiers were developed based on 30 transcriptomes that were randomly selected from all available data (n=40). Randomization was used so we could test the viability of IA prediction in patients that have potentially confounding covariates (comorbidities and demographics). Example 2, Table 1 shows that, in the training cohort, there were differences in the rate of smoking between the IA and control groups, which may reflect an established association between IA and smoking. The approach in this Example was designed differently than as described in Example 1, in which we found an 82-transcript expression signature of IA by transcriptome profiling of a cohort-controlled group of patients. But even with this difference, 38% (10) of 26 classifier transcripts were part of the 82-transcript signature described herein. These include CYP1B1, CD177, ARMC12, OLAH, CD163, ADTRP, VWA8, G0S2, FCRL5, and C1orf226. Notably, when we performed qPCR validation in a new cohort of independent patients on seven of these genes, six of the seven (CYP1B1, ARMC12, OLAH, CD163, G0S2 and FCRL5) demonstrated consistent expression differences.

Biological Role of Classifier Transcripts

Our data demonstrate that differential expression between patients with and without IA reflects neutrophil activation. Gene set enrichment analysis performed on the 95 differentially expressed transcripts (q<0.05) found in the training dataset showed dysregulation of inflammatory and defense responses, and signaling (particularly IL-1, a major neutrophil activator) in neutrophils from patients with IA. These results mirror those of Example 1, which also showed differential expression was characteristic of increased peripheral activation. Indeed, several of the 26 classifier transcripts may be involved in neutrophil activation. CD177 is a cell surface glycoprotein that plays a role in the activation and transmigration of neutrophils, while IL18R1 contributes to neutrophil activation through IL-18 signaling. Nectin-2 (PVRL2), a membrane glycoprotein, and PDE9A, a cGMP-specific phosphodiesterase, are both involved in cell adhesion. Additionally, lower PTGES expression may be partially responsible for increasing the lifespan of neutrophils, since it is involved in p53-induced apoptosis. Based on these findings, the neutrophil activation responses that may be dynamically involved in IA are reflected in our classification model, with aberrant expression of these transcripts increasing the likelihood of IA classification.

The differential expression of many other classifier transcripts reflects a complex inflammatory response in neutrophils in patients with IA. For example, CD163 has been shown to be increased in neutrophils during sepsis and could be contributing to vascular inflammation during IA. Expression differences of other transcripts, like TGS1 and CYP26B1 (that are differentially expressed in tuberculosis, and juvenile idiopathic arthritis, respectively) could be related neutrophil functions that are pertinent to many responses to intravascular perturbations during IA. Other transcripts—such as ADTRP (expressed by macrophages in coronary artery plaques), OCLN (increased in activated T-lymphocytes and in whole blood during sepsis), and OLAH (increased in PBMCs during non-small cell lung cancer)—are involved in inflammation but have not been reported to be differentially expressed in neutrophils. Still, the roles of several other model transcripts (such as MTRNR2L10, ARMC12, and LOC100506299) are widely unknown. Thus, it is believed the present disclosure provides the first demonstration of IA prediction from RNA expression patterns in the blood.

Example 2,

TABLE 1

Clinical characteristics.*

|  | Training Cohort | | Testing Cohort | |
| --- | --- | --- | --- | --- |
|  | Control (n = 15) | Aneurysm (n = 15) | Control (n = 5) | Aneurysm (n = 5) |
| Age (Mean ± SE) | 59 ± 4.8 | 63 ± 2.8 | 63 ± 7.2 | 52.6 ± 6.6 |
| Age [Median (Q1/Q3)] | 61 (52.5/71.5) | 64 (56.5/68.5) | 68 (62/71) | 53 (47/54) |
| Gender (number of patients) | | | | |
| Female | 40% | 66.67% | 60% | 40% |
| Smoking (number of patients) | | | | |
| Yes | 0% | 20% | 40% | 60% |
| Comorbidities (number of patients) | | | | |
| Hypertension | 60% | 60% | 60% | 20% |
| Heart Disease | 6.67% | 26.67% | 40% | 0% |
| High Cholesterol | 26.67% | 40% | 60% | 0% |
| Stroke History | 6.67% | 0% | 0% | 0% |
| Diabetes | 33.33% | 20% | 20% | 0% |
| Osteoarthritis | 20% | 33.33% | 20% | 0% |

*Clinical characteristics of the randomly-created training and testing cohorts. With the exception of age, these factors were quantified as binary data points. The clinical factors were retrieved from the patients' medical records via the latest Patient Medical History form administered prior to imaging. Since this medical record contained self-reported information, the presence of each comorbidity was corroborated with each patients' reported list of medications (e.g. hypertension with Lisinopril, hyperlipidemia with simvastatin, heart disease with metoprolol, stroke history with clopidogrel, diabetes mellitus with metformin, and osteoarthritis with NSAIDs/tramadol).

Example 2,

TABLE 2

Gene ontology (GO) analysis.*

| Category | GO Term | Description | p-value | q-value |
| --- | --- | --- | --- | --- |
| Transcripts with higher expression in IA | | | | |
| Process | GO:0031347 | Regulation of Defense Response | 5.11E−06 | 0.0658 |
| Process | GO:0050727 | Regulation of Inflammatory Response | 1.01E−05 | 0.0652 |
| Process | GO:0019934 | cGMP-Mediated Signaling | 3.77E−05 | 0.162 |
| Process | GO:0032101 | Regulation of Response to External Stimulus | 3.90E−05 | 0.125 |
| Process | GO:0031348 | Negative Regulation of Defense Response | 4.45E−05 | 0.115 |
| Process | GO:0050728 | Negative Regulation of Inflammatory Response | 5.21E−05 | 0.112 |
| Process | GO:0007165 | Signal Transduction | 6.64E−05 | 0.122 |
| Function | GO:0004908 | Interleukin-1 Receptor Activity | 2.25E−06 | 0.00858 |
| Function | GO:0004872 | Receptor Activity | 7.22E−05 | 0.138 |
| Function | GO:0060089 | Molecular Transducer Activity | 7.22E−05 | 0.092 |
| Function | GO:0038023 | Signaling Receptor Activity | 1.32E−04 | 0.127 |
| Transcripts with lower expression in IA | | | | |
| Function | GO:0043295 | Glutathione Binding | 1.16E−04 | 0.148 |
| Function | GO:0046906 | Tetrapyrrole Binding | 1.40E−04 | 0.134 |

*Gene set enrichment analysis was performed on the 95 significantly differentially expressed genes (q < 0.05) in peripheral blood samples obtained from patients with intracranial aneurysms (IA). Significantly enriched ontologies with an false discovery rate adjusted p-value (q-value) <0.20 were considered (FDR of 20%). Transcripts with higher expression in IA demonstrated regulation of inflammatory and defense responses, signaling and cell motility. Significantly enriched ontologies in transcripts with lower expression in IA demonstrated regulation of glutathione and tetrapyrrole binding.

Example 2,

TABLE 3

26 transcripts selected for classification model training.*

| Transcript | Gene ID | Accession No. | Log2 (F-C) | P-Value | Q-Value |
|---|---|---|---|---|---|
| PVRL2 | 5819 | NM_002856.2 | 2.27 | 5.54E−12 | 6.94E−09 |
| CYP1B1 | 1545 | NM_000104.3 | 1.53 | 4.13E−10 | 3.88E−07 |
| CD177 | 57126 | NM_020406.3 | 1.48 | 8.04E−06 | 2.91E−03 |
| PDE9A | 5152 | NM_002606.2 | 1.45 | 5.67E−05 | 9.90E−03 |
| ARMC12 | 221481 | NM_145028.4 | 1.37 | 1.38E−12 | 2.07E−09 |
| OLAH | 55301 | NM_018324.2 | 1.15 | 1.71E−11 | 1.83E−08 |
| TGS1 | 96764 | NM_024831.7 | 1.02 | 1.72E−14 | 4.31E−11 |
| CD163 | 9332 | NM_004244.5 | 0.98 | 2.65E−09 | 1.99E−06 |
| LOC100506229 | 100506229 | NR_03 9975.1 | 0.96 | 1.23E−05 | 3.55E−03 |
| OCLN | 100506658 | NM_002538.3 | 0.85 | 4.07E−07 | 2.37E−04 |
| SEMA6B | 10501 | NM_032108.3 | 0.80 | 7.62E−05 | 1.19E−02 |
| ADTRP | 84830 | NM_001143948.1 | 0.77 | 1.61E−05 | 4.47E−03 |
| VWA8 | 23078 | NM_015058.1 | 0.70 | 2.56E−06 | 1.20E−03 |
| MTRNR2L10 | 100463488 | NM_001190708.1 | 0.63 | 1.21E−05 | 3.55E−03 |
| HOXB2 | 3212 | NM_002145.3 | 0.62 | 6.25E−05 | 1.02E−02 |
| EPCAM | 4072 | NM_002354.2 | 0.60 | 1.02E−05 | 3.50E−03 |
| IL18R1 | 8809 | NM_003855.3 | 0.59 | 1.17E−05 | 3.55E−03 |
| IGSF23 | 147710 | NM_001205280.1 | −0.80 | 5.87E−05 | 9.94E−03 |
| PTGES | 9536 | NM_004878.4 | −0.91 | 4.78E−05 | 8.98E−03 |
| G0S2 | 50486 | NM_015714.3 | −0.96 | 6.71E−06 | 2.66E−03 |
| FCRL5 | 83416 | NM_031281.2 | −1.26 | 4.31E−06 | 1.80E−03 |
| C1orf226 | 400793 | NM_001135240.1 | −1.51 | 1.27E−14 | 4.31E−11 |
| UTS2 | 10911 | NM_021995.2 | −1.93 | 8.85E−14 | 1.66E−10 |
| HBG2 | 3048 | NM_000184.2 | −1.97 | 6.62E−10 | 5.53E−07 |
| CYP26B1 | 56603 | NM_019885.3 | −2.99 | 4.32E−07 | 2.37E−04 |
| C1QL1 | 10882 | NM_006688.4 | −3.25 | 5.16E−22 | 3.88E−18 |

*Significantly differentially expressed transcripts with FDR <0.05 and fold-change ≥1.5. Bolded transcripts are additional to those 82 transcripts from Example .1 (F-C = fold-change)

The cDNA nucleotide sequences of the 26 biomarkers in this table are provided as SEQ ID NOs 13-38, respectively.

Example 2,

SUPPLEMENTAL TABLE 1

Batch Assignment.*

| ID | Class | Batch (i.e. Example 1 or new pt in Example 2) |
|---|---|---|
| | Training Cohort | |
| C1 | Control | 1 |
| C2 | Control | 1 |
| C3 | Control | 1 |
| C4 | Control | 1 |
| C5 | Control | 1 |
| C6 | Control | 1 |
| C7 | Control | 1 |
| C8 | Control | 2 |
| C9 | Control | 2 |
| C10 | Control | 2 |
| C11 | Control | 2 |
| C12 | Control | 2 |
| C13 | Control | 2 |
| C14 | Control | 2 |
| C15 | Control | 2 |
| A1 | Aneurysm | 1 |
| A2 | Aneurysm | 1 |
| A3 | Aneurysm | 1 |
| A4 | Aneurysm | 1 |
| A5 | Aneurysm | 1 |
| A6 | Aneurysm | 1 |
| A7 | Aneurysm | 1 |
| A8 | Aneurysm | 1 |
| A9 | Aneurysm | 2 |
| A10 | Aneurysm | 2 |
| A11 | Aneurysm | 2 |
| A12 | Aneurysm | 2 |
| A13 | Aneurysm | 2 |
| A14 | Aneurysm | 2 |
| A15 | Aneurysm | 1 |
| | Testing Cohort | |
| C16 | Control | 1 |
| C17 | Control | 1 |
| C18 | Control | 1 |
| C19 | Control | 2 |
| C20 | Control | 1 |
| A16 | Aneurysm | 1 |
| A17 | Aneurysm | 1 |
| A18 | Aneurysm | 2 |
| A19 | Aneurysm | 2 |
| A20 | Aneurysm | 2 |

*Over the study period to samples were collected and processed in two main batches. The earlier batch is designated as "1" and the later batch is designated as "2." When creating the training and testing cohorts, data from each batch was randomly partitioned into each group.

Example 2,

SUPPLEMENTAL TABLE 2

Primers used for qPCR and their efficiencies.*

| Transcript | Primer Sequence | Annealing Temp. (° C.) | Eff. | PCR Prod. Length (bp) | SEQ ID NO |
|---|---|---|---|---|---|
| CD177 | 5'-ACACACGGAAACTTGGCTCA-3' | 60.0 | 1.04 | 124 | 1 |
|  | 5'-CCAGGGTTGATGTGAGTCCTAC-3' |  |  |  | 2 |
| CYP1B1 | 5'-CAGTGAATTTGGGCTGCTGT-3' | 60.0 | 0.95 | 148 | 39 |
|  | 5'-TGACGACTGGGCCTACATAC-3' |  |  |  | 40 |
| ARMC12 | 5'-CCTCAACAACCTTCCACTGCC-3' | 60.0 | 1.04 | 130 | 41 |
|  | 5'-CAGGTAGCTCAGCAGTCGTA-3' |  |  |  | 42 |
| OLAH | 5'-GCAGCCAGTCATCCAGGATA-3' | 60.0 | 0.92 | 175 | 43 |
|  | 5'-ATCTTTGGGAATGCGATGCC-3' |  |  |  | 44 |
| CD163 | 5'-TGTCGTGGGAATGAGTCAGC-3' | 60.0 | 0.99 | 109 | 45 |
|  | 5'-TGGATCCATCTGAGCAGGTC-3' |  |  |  | 46 |
| G0S2 | 5'-CACTAAGGTCATTCCCGCCT-3' | 60.0 | 0.91 | 125 | 47 |
|  | 5'-AGCACGTACAGCTTCACCAT-3' |  |  |  | 48 |
| FCRL5 | 5'-TCAGTGTCTACCTGCCCAAG-3' | 60.0 | 1.07 | 89 | 49 |
|  | 5'-GCCTTGACTTGCTGGGTTAC-3' |  |  |  | 50 |
| GAPDH | 5'-CGTCTCTGCTCCTCCTGTT-3' | 60.0 | 1.09 | 81 | 11 |
|  | 5'-CCATGGTGTCTGAGCGATGT-3' |  |  |  | 12 |
| 18s rRNA | 5'-GGCCCTCTAATTGGAAGAGTC-3' | 60.0 | 1.09 | 145 | 51 |
|  | 5'-CCAAGATCCAACTACGAGCTT-3' |  |  |  | 52 |
| GPI | 5'-AGGCTGCTGCCACATAAGGT-3' | 60.0 | 0.95 | 240 | 53 |
|  | 5'-AGCGTCGTGAGAGGTCACTTG-3' |  |  |  | 54 |

*Primers were selected using Primer3 and NCBI's Primer Blast. All efficiencies were within the range of 0.90-1.10. (bp = base pair, Eff = efficiency, Prod. = product, Temp. = temperature)

Example 2, Supplemental

TABLE 3

RNA Quality.*

| ID | Class | 260/280 | RIN |
|---|---|---|---|
| Training Cohort | | | |
| C1 | Control | 2.02 | 7.4 |
| C2 | Control | 1.92 | 6.5 |
| C3 | Control | 2.08 | 7.1 |
| C4 | Control | 2.05 | 7.9 |
| C5 | Control | 1.96 | 6.7 |
| C6 | Control | 2.08 | 6.2 |
| C7 | Control | 2.04 | 7.3 |
| C8 | Control | 2.04 | 6.6 |
| C9 | Control | 2.04 | 6.0 |
| C10 | Control | 2.05 | 6.0 |
| C11 | Control | 2.10 | 5.5 |
| C12 | Control | 2.01 | 7.9 |
| C13 | Control | 2.03 | 6.0 |
| C14 | Control | 1.90 | 5.2 |
| C15 | Control | 2.02 | 8.2 |
| A1 | Aneurysm | 2.04 | 7.8 |
| A2 | Aneurysm | 2.07 | 7.5 |
| A3 | Aneurysm | 2.02 | 6.1 |
| A4 | Aneurysm | 2.03 | 7.3 |
| A5 | Aneurysm | 1.99 | 6.5 |
| A6 | Aneurysm | 2.02 | 7.5 |
| A7 | Aneurysm | 2.05 | 7.7 |
| A8 | Aneurysm | 1.95 | 7.2 |
| A9 | Aneurysm | 2.07 | 6.7 |
| A10 | Aneurysm | 2.00 | 6.9 |
| A11 | Aneurysm | 1.97 | 6.4 |
| A12 | Aneurysm | 2.12 | 7.3 |
| A13 | Aneurysm | 1.96 | 7.4 |
| A14 | Aneurysm | 2.07 | 7.8 |
| A15 | Aneurysm | 1.97 | 6.9 |
| Testing Cohort | | | |
| C16 | Control | 2.07 | 7.0 |
| C17 | Control | 2.05 | 6.6 |
| C18 | Control | 1.99 | 7.1 |
| C19 | Control | 1.92 | 6.6 |
| C20 | Control | 1.97 | 6.4 |
| A16 | Aneurysm | 2.06 | 8.1 |
| A17 | Aneurysm | 2.07 | 6.0 |
| A18 | Aneurysm | 2.08 | 7.1 |
| A19 | Aneurysm | 2.03 | 7.2 |
| A20 | Aneurysm | 2.06 | 6.0 |

*The quality of the RNA samples was assessed by the 260/280 ratio and the RIN. (RIN = RNA integrity number)

Example 2,

SUPPLEMENTAL TABLE 4

Characteristics of 27 aneurysms in all patients with
IAs (5 patients had multiple intracranial aneurysms)*

| ID | IA Size | IA Location | Presence of Additional IAs | Family History of IA | Indications for DSA |
|---|---|---|---|---|---|
| | | | Training Cohort | | |
| A1 | 10 mm | VB Junction | No | No | MRI for hand numbness indicated possible IA |
| A2 | 8 mm | ICA Paraophthalmic | No | No | Follow-up imaging of known IA |
| A3 | 4 mm | Ophthalmic | +2 (1.5 mm ICA, 3 mm clinoid segment) | No | MRI for headache indicated possible IA |
| A4 | 10.8 mm | MCA | +2 (2.3 mm MCA, small ACom) | No | Incidental finding on MRI indicated possible IA |
| A5 | 9 mm | PCom | No | No | Follow-up of known IA |
| A6 | 5 mm | BT | No | No | MRA and CT for tremor revealed possible IA |
| A7 | 13 mm | ACA | No | Yes | MRI for decreased vision in left eye indicated possible IA |
| A8 | 5 mm | ICA | +1 (3.5 mm paraophthalmic) | Yes | MRI for tremors indicated possible IA |
| A9 | 6 mm | MCA | No | No | MRA following vehicle accident indicated possible IA |
| A10 | 3.7 mm | ACom | No | No | Incidental finding on CT for headache indicated possible IA |
| A11 | 1.4 mm | MCA | No | No | Incidental finding on MRI indicated possible IA |
| A12 | 2 mm | PCA | +1 (2 mm ICA) | No | MRI for migraine indicated possible IA |
| A13 | 3.9 mm | BT | No | No | Incidental finding on MRA for headache indicated possible IA |
| A14 | 1 mm | ICA | No | Yes | Follow-up imaging of known IA |
| A15 | 3 mm | BT | No | No | MRI for headache indicated possible IA |
| | | | Testing Cohort | | |
| A16 | 4.5 mm | MCA | No | No | Incidental finding on CT indicated possible IA |
| A17 | 19 mm | ICA | No | No | MRI for double vision indicated possible IA |
| A18 | 5.1 mm | ICA | No | No | MRI for headache indicated possible IA |
| A19 | 7 mm | MCA | +1 (3.5 mm ACA) | No | Follow-up imaging of known IA |
| A20 | 2 mm | ACA | No | No | Follow-up imaging of known IA |

*Aneurysm size ranged from 1 mm to 19 mm. Sixteen IAs (60%) were classified as small (diameter <5 mm) and 11 (40%) were classified as large (diameter ≥5 mm). The aneurysms were situated at various locations in the Circle of Willis, with most being around the internal carotid artery (ICA) and its branches. Three patients with IAs had a family history of the disease. In general, digital subtraction angiography was performed for either confirmation of IA presence after an incidental finding of IA on noninvasive imaging, or for follow-up imaging of a previously detected IA. (ACA = anterior cerebral artery, AComA = anterior communicating artery, BT = basilar terminus, CT = computed tomography, DSA = digital subtraction angiography, IA = intracranial aneurysm, ICA = internal carotid artery, MCA = middle cerebral artery, MRA = magnetic resonance angiography, MRI = magnetic resonance imaging, PComA = posterior communicating artery, VB = vertebrobasilar)

Example 2, Supplemental

SUPPLEMENTAL TABLE 5

RNA Sequencing Quality Control Analysis.*

| ID | Class | M. Seqs. | Poor Qual. Seqs. | Seqs. Length | % GC | % Aligned | M. Aligned | Detected Transcripts |
|---|---|---|---|---|---|---|---|---|
| | | | | Training Cohort | | | | |
| C1 | Control | 59.3 | 0 | 51 | 49 | 96.50% | 54.4 | 11434 |
| C2 | Control | 68.9 | 0 | 51 | 49 | 96.60% | 63.3 | 11928 |
| C3 | Control | 80.3 | 0 | 51 | 50 | 96.30% | 73.5 | 11829 |
| C4 | Control | 97.4 | 0 | 51 | 50 | 96.00% | 88.9 | 11064 |

SUPPLEMENTAL TABLE 5-continued

RNA Sequencing Quality Control Analysis.*

| ID | Class | M. Seqs. | Poor Qual. Seqs. | Seqs. Length | % GC | % Aligned | M. Aligned | Detected Transcripts |
|---|---|---|---|---|---|---|---|---|
| C5 | Control | 67.8 | 0 | 51 | 49 | 96.40% | 62.2 | 12135 |
| C6 | Control | 36.2 | 0 | 51 | 49 | 96.10% | 33.2 | 12057 |
| C7 | Control | 79.3 | 0 | 51 | 49 | 96.80% | 72.7 | 10117 |
| C8 | Control | 66.0 | 0 | 51 | 50 | 95.50% | 60.0 | 12048 |
| C9 | Control | 74.4 | 0 | 51 | 50 | 95.10% | 66.8 | 12154 |
| C10 | Control | 64.3 | 0 | 51 | 51 | 94.90% | 57.9 | 11866 |
| C11 | Control | 36.9 | 0 | 51 | 51 | 96.30% | 33.7 | 11072 |
| C12 | Control | 51.5 | 0 | 51 | 50 | 95.60% | 46.8 | 11823 |
| C13 | Control | 58.5 | 0 | 51 | 51 | 95.50% | 53.0 | 11779 |
| C14 | Control | 64.6 | 0 | 51 | 51 | 94.10% | 57.7 | 11304 |
| C15 | Control | 47.3 | 0 | 51 | 50 | 95.30% | 42.7 | 12191 |
| A1 | Aneurysm | 48.1 | 0 | 51 | 49 | 96.90% | 44.5 | 11656 |
| A2 | Aneurysm | 35.7 | 0 | 51 | 48 | 96.80% | 32.9 | 11101 |
| A3 | Aneurysm | 55.9 | 0 | 51 | 49 | 96.90% | 51.4 | 11725 |
| A4 | Aneurysm | 61.3 | 0 | 51 | 49 | 97.20% | 56.9 | 11087 |
| A5 | Aneurysm | 23.4 | 0 | 51 | 49 | 95.90% | 21.4 | 11951 |
| A6 | Aneurysm | 35.8 | 0 | 51 | 49 | 96.40% | 32.3 | 12108 |
| A7 | Aneurysm | 26.9 | 0 | 51 | 50 | 97.10% | 24.9 | 10151 |
| A8 | Aneurysm | 59.5 | 0 | 51 | 49 | 96.00% | 54.1 | 12111 |
| A9 | Aneurysm | 86.9 | 0 | 51 | 51 | 84.60% | 70.0 | 10809 |
| A10 | Aneurysm | 64.9 | 0 | 51 | 50 | 96.60% | 59.5 | 10869 |
| A11 | Aneurysm | 75.3 | 0 | 51 | 51 | 95.90% | 68.6 | 11938 |
| A12 | Aneurysm | 47.2 | 0 | 51 | 51 | 89.50% | 39.9 | 11512 |
| A13 | Aneurysm | 42.1 | 0 | 51 | 50 | 95.20% | 38.2 | 11185 |
| A14 | Aneurysm | 32.3 | 0 | 51 | 50 | 88.50% | 27.2 | 11903 |
| A15 | Aneurysm | 14.6 | 0 | 51 | 49 | 95.00% | 13.0 | 12127 |
| Testing Cohort | | | | | | | | |
| C16 | Control | 27 | 0 | 51 | 48 | 96.50% | 24.8 | 11433 |
| C17 | Control | 35.9 | 0 | 51 | 49 | 94.90% | 32.3 | 12158 |
| C18 | Control | 53.3 | 0 | 51 | 50 | 95.80% | 48.5 | 11626 |
| C19 | Control | 44.2 | 0 | 51 | 49 | 96.00% | 40.6 | 12115 |
| C20 | Control | 89.1 | 0 | 51 | 50 | 95.70% | 81.1 | 11580 |
| A16 | Aneurysm | 60.4 | 0 | 51 | 49 | 96.90% | 55.9 | 12063 |
| A17 | Aneurysm | 29.1 | 0 | 51 | 50 | 96.60% | 26.8 | 11442 |
| A18 | Aneurysm | 55.6 | 0 | 51 | 51 | 93.90% | 49.3 | 10817 |
| A19 | Aneurysm | 39.8 | 0 | 51 | 50 | 97.40% | 36.8 | 11347 |
| A20 | Aneurysm | 42.2 | 0 | 51 | 51 | 95.50% | 38.3 | 12018 |

*The quality of the RNA sequencing experiments. Overall, prior to alignment all samples had an average of 53.84M sequences. The sequencing experiments had an average of 48.4M mapped reads with a 95.37% read mapping rate, and detected an average of 11591 transcripts (transcripts with TPM > 1 after batch effect correction). (M. = million, Seqs. = sequences, Qual. = quality)

Example 2,

SUPPLEMENTAL TABLE 6

Clinical characteristics of the additional cohort of 5 patients with intracranial aneurysms and 5 control subjects without intracranial aneurysms (confirmed on imaging) used for qPCR validation.*

| | Patients with IA (n = 5) | Control Patients without IA (n = 5) |
|---|---|---|
| Age (Mean ± SE) | 54.6 ± 3.60 | 50.6 ± 6.23 |
| Age [Median (Q1/Q3)] | 58 (46/60) | 50 (39/62) |
| Gender | | |
| Female | 40% | 80% |
| Smoking Status | | |
| Yes | 60% | 0% |
| Comorbidities | | |
| Hypertension | 0% | 20% |
| High Cholesterol | 60% | 40% |
| Heart Disease | 20% | 0% |

SUPPLEMENTAL TABLE 6-continued

Clinical characteristics of the additional cohort of 5 patients with intracranial aneurysms and 5 control subjects without intracranial aneurysms (confirmed on imaging) used for qPCR validation.*

| | Patients with IA (n = 5) | Control Patients without IA (n = 5) |
|---|---|---|
| Stroke History | 20% | 40% |
| Diabetes | 0% | 20% |
| Osteoarthritis | 20% | 20% |

Clinical information, with the exception of age was quantified as binary data points. Clinical factors were retrieved from the patients' medical records via the latest Patient Medical History form administered prior to imaging, and the presence of each comorbidity was corroborated with each patients' reported list of medications. (IA = intracranial aneurysm, SE = standard error, Q = quartile)

Example 2,

SUPPLEMENTAL TABLE 7

Characteristics of intracranial aneurysms in the group of 5 patients with IAs used for qPCR validation.*

| IA Patient no. | IA Size (mm) | IA Location | Presence of Additional IAs | Family History of IA | Indications for DSA |
|---|---|---|---|---|---|
| A21 | 7 | MCA | No | No | Noninvasive imaging for extremity weakens indicated possible IA |
| A22 | 10 | MCA | No | No | Noninvasive imaging seizure indicated possible IA |
| A23 | 6.1 | ICA | No | No | Screening due to family history of IA |
| A24 | 2.8 | ICA | No | No | MRI for migraine indicated possible IA |
| A25 | 3.2 | MCA | No | No | CTA imaging indicated possible IA |

*Aneurysm size ranged from 2.8 mm to 7 mm. Two of the 5 IAs (40%) were classified as small (<5 mm) and three (60%) were classified as large (≥5 mm). The aneurysms were situated in the Circle of Willis, in the anterior vasculature (MCA) and at the ICA. (CTA = computed tomography angiography, IA = intracranial aneurysm, ICA = internal carotid artery, MCA = middle cerebral artery, MRI = magnetic resonance imaging)

Example 2,

SUPPLEMENTAL TABLE 8

Summary of model performances across different analyses.*

| | Sen. | Spec. | Acc. | AUC | PPV* | NPV* |
|---|---|---|---|---|---|---|
| Model training (LOO cross-validation) | | | | | | |
| Cosine NN | 0.87 | 0.60 | 0.73 | 0.72 | 0.10 | 0.99 |
| DLDA | *0.67* | *0.80* | *0.73* | *0.72* | *0.15* | *0.98* |
| NSC | 0.53 | 0.93 | 0.73 | 0.69 | 0.28 | 0.97 |
| SVM | 0.47 | 0.53 | 0.50 | 0.54 | 0.05 | 0.95 |
| Model testing | | | | | | |
| Cosine NN | 0.60 | 0.60 | 0.60 | 0.62 | 0.07 | 0.97 |
| DLDA | *0.80* | *1.00* | *0.90* | *0.80* | *1.00* | *0.99* |
| NSC | 0.80 | 0.80 | 0.80 | 0.76 | 0.17 | 0.99 |
| SVM | 0.40 | 1.00 | 0.70 | 0.72 | 1.00 | 0.97 |
| Cosine NN | 0.75 | 0.65 | 0.70 | 0.70 | 0.10 | 0.98 |
| DLDA | *0.65* | *0.95* | *0.80* | *0.84* | *0.41* | *0.98* |
| NSC | 0.45 | 0.90 | 0.68 | 0.68 | 0.19 | 0.97 |
| SVM | 0.40 | 0.85 | 0.63 | 0.69 | 0.12 | 0.96 |

*Model performances during training, testing and LOO retraining. Sensitivity, specific, accuracy, and AUC.
*PPV and NPV calculated at 5% IA prevalence.
Bold and italic numbers indicate best performing model.
(Sen. = sensitivity, Spec. = specificity, Acc. = accuracy, AUC = area under the receiver operating characteristic curve, PPV = positive predictive value, NPV = negative predictive value)

Example 3

This Example provides data demonstrating the use of biomarkers to discriminate large from small aneurysms. This is meaningful because the most widely-used metric for assessing the risk of an aneurysm rupturing is the aneurysms size. This size metric was adopted from longitudinal prospective studies which reported that larger aneurysms are more dangerous because they are more likely to rupture.

To determine if genes in circulating signatures of aneurysm could be used to assess the risk of aneurysm rupture, we assessed the capability of transcriptome profiling to identify significant differences between small and large intracranial aneurysms (small defined as <5 mm, large as ≥5 mm).

Study Population

This study was approved by the University at Buffalo Health Sciences Institutional Review. Methods were carried out in accordance with the approved protocol. Written informed consent was obtained from all subjects. Patients undergoing cerebral digital subtraction angiography (DSA) with positive and negative intracranial aneurysm (IA) diagnoses were enrolled in this study. Reasons for the patients to receive DSA included confirmation of findings from noninvasive imaging of the presence of IAs, vascular malformations, or carotid stenosis, or follow-up noninvasive imaging of previously detected IAs. All consenting patients were older than 18 years, were English speaking, and had not received previous treatment for IA. We excluded patients who potentially had altered immune systems; this included patients who were pregnant, had recently undergone invasive surgery, were undergoing chemotherapy, had a body temperature above 37.78° C. (100° F.), had received solid organ transplants, had autoimmune diseases, and those who were taking prednisone or any other immunomodulating drugs. Furthermore, included patients did not have any other known cerebrovascular malformations or extracranial aneurysms, including abdominal aortic aneurysms.

Neutrophil Isolation

Sixteen mL of blood was drawn from the access catheter in the femoral artery and transferred into two 8 mL, citrated, cell preparation tubes (BD, Franklin Lakes, N.J.). Neutrophils were isolated within 1 hour of peripheral blood collection. wwCell preparation tubes were centrifuged at 1,700×g for 25 minutes to separate erythrocytes and neutrophils from mononuclear cells and plasma in the peripheral blood samples via a Ficoll density gradient. Erythrocytes and neutrophils were collected into a 3 mL syringe. Following hypotonic lysis of red blood cells, neutrophils were isolated by centrifugation at 400×g for 10 min and disrupted and stored in TRIzol reagent (Life Technologies, Carlsbad, Calif.) at −80° C. until further processing. Neutrophils isolated in this fashion are more than 98% CD66b+ by flow cytometry and contain no contaminating CD14+ monocytes.

RNA Preparation

Neutrophil RNA was extracted using TRIzol, according to the manufacturer's instructions. Trace DNA was removed by DNase I (Life Technologies, Carlsbad, Calif.) treatment. RNA was purified using the RNeasy MinElute Cleanup Kit (Qiagen, Venlo, Limburg, Netherlands) and suspended in RNase-free water. The purity and concentration of RNA in each sample was measured by absorbance at 260 nm on a NanoDrop 2000 (Thermo Scientific, Waltham, Mass.), and 200-400 ng of RNA was sent to our university's Next-Generation Sequencing and Expression Analysis Core facility for further quality control. Precise RNA concentration was measured at the core facility via the Quant-iT RiboGreen Assay (Invitrogen, Carlsbad, Calif.) with a TBS-380 Fluorometer (Promega, Madison, Wis.), whereas the quality of the RNA samples was measured with an Agilent 2100 BioAnalyzer RNA 6000 Pico Chip (Agilent, Las Vegas, Nev.). RNA samples of acceptable purity (260/280 ratio of ≥1.9) and integrity (RIN≥5.0) were considered for RNA sequencing.

Results

The original cohort (as described in Example 1) contained 22 individuals (11 with IA, 11 without 11), from which we developed the 82-transcript signature. Subsequently, we added 18 patients (as described in Example 2), making our cohort 40 individuals (20 with IA, 20 without IA). Using this group, we developed the 26-transcript model. In this Example we added 26 more samples, resulting in a cohort of 66 samples (31 with IA, 35 without IA).

In the dataset of 31 samples from patients with aneurysms, there were 15 small aneurysm (<5 mm) samples and 16 large aneurysm (≥5 mm) samples. We applied the same statistical requirements described in Example 2 to evaluate differences in the transcriptomes of circulating neutrophils between control and aneurysm patients (TPM>1, q-value<0.05, and absolute fold-change>2). We found that 9 differentially expressed genes (ARMC12, C1orf226, CD177, OLAH, HRK, ITGA7, LYPD2, PTGDS, RPL39L) are present in the original 82-gene list developed in the 11v11 analysis (Example 1). Furthermore, 6 significantly differently expressed genes (ARMC12, C1orf226, CD177, HBG2, LOC100506229, OLAH) were present in the 26-gene signature/model described in Example 2 (developed from 15v15 analysis. These transcripts are reported in Example 3, Table 1 as "Gene Set 1". The transcripts bolded indicate they are present in both 82-gene signature and 26-gene model. With the exception of LYPD2 and PTGDS, the genes with increased expression IA from the signature and the model had even higher expression in larger aneurysms, and the genes with decreased expression in IA based on the signature and the model had even lower expression in larger aneurysms. This indicates that the present disclosure provides a method for generating a prediction of a size or size range of the aneurysm, and thus a risk of rupture. HRK, ITGA7, RPL39L were part of the original 82-gene set, but not part of the 26 gene panel, but still are significantly different between individuals with large and small aneurysms. Therefore, the disclosure encompasses determining these biomarkers. In certain embodiments, the disclosure encompasses including analysis of these biomarkers for use in differentiation of patients with large vs small IAs.

Example 3,

TABLE 1

| Gene Set 1 | | | |
|---|---|---|---|
| Transcript | Log2 fold-change | P-value | Q-value |
| ARMC12 | 1.48 | 1.78E−06 | 1.12E−04 |
| C1orf226 | −2.11 | 6.30E−18 | 1.25E−14 |
| CD177 | 2.77 | 2.09E−11 | 8.71E−09 |
| HBG2 | −1.26 | 2.93E−04 | 5.90E−03 |
| HRK | −1.42 | 3.83E−06 | 2.07E−04 |
| ITGA7 | 1.04 | 8.06E−08 | 9.32E−06 |
| LOC100506229 | 1.38 | 5.29E−09 | 9.38E−07 |
| LYPD2 | −1.13 | 2.54E−06 | 1.48E−04 |
| OLAH | 1.23 | 4.04E−04 | 7.60E−03 |
| PTGDS | −2.12 | 7.58E−12 | 3.77E−09 |
| RPL39L | 1.58 | 1.13E−06 | 7.97E−05 |

In this dataset we created a machine learning algorithm using a quadratic discriminant analysis model to relate the set of 11 IA-associated genes to the size of the IA (small<5 mm, large≥5 mm). We used expression levels of these transcripts to train biomarker models using the machine learning toolbox in MATLAB. Five-fold cross-validation in this cohort estimated the model's accuracy to be 0.61 with an AUC of 0.61.

While the invention has been described through specific embodiments, routine modifications will be apparent to those skilled in the art and such modifications are intended to be within the scope of the present invention.

What is claimed is:

1. A method comprising analyzing a neutrophil sample from a subject for expression of biomarkers comprising neutrophil RNA expression, wherein determining expression of the biomarkers that is different from a control neutrophil RNA expression obtained from individuals who do not have an intracranial aneurysm indicates the presence of an intracranial aneurysm in the subject, and wherein analyzing the biological sample comprises:
   i) determining that expression of the following neutrophil RNA expression biomarkers is increased relative to the control: PVRL2, CYP1B1, CD177, PDE9A, ARMC12, OLAH, TGS1, CD163, LOC100506229, OCLN, SEMA6B, ADTRP, VWA8, MTRNR2L1, HOXB2, EPCAM, and IL18R1,
   and
   ii) determining that expression of the following neutrophil RNA expression biomarkers is decreased by a statistically significant difference relative to the control: IGSF23, PTGES, G0S2, FCRL5, C1orf226, UTS2, HBG2, CYP26B1, and C1QL1, to thereby determine the presence of the intracranial aneurysm, the method further comprising treating the intracranial aneurysm with a flow diverter, endovascular coiling, or surgical clipping.

2. The method of claim 1, further comprising determining increased expression of C21orf15, CYP1B1, FLT3, XKR3, SLC12A7, and PAM, relative to the control, and/or determining decreased expression of GPC4, FBN1, and IL-8 relative to the control.

3. The method of claim 1, further comprising determining increased expression C21orf15, CYP1B1, FLT3, XKR3, SLC12A7, PAM, and TCL1A relative to the control, and/or determining decreased expression of GPC4, FBN1, IL-8, GBP5, ETV7, MFSD9, SERPING1 and CARD17 relative to the control.

4. The method of claim 1, further comprising determining increased expression of TCL1A relative to the control, and/or determining decreased expression of CARD17 relative to the control.

* * * * *

SEQUENCE LISTING

<160> NUMBER OF SEQ ID NOS: 54

<210> SEQ ID NO 1
<211> LENGTH: 20
<212> TYPE: DNA
<213> ORGANISM: artificial sequence
<220> FEATURE:
<223> OTHER INFORMATION: Primer

<400> SEQUENCE: 1
acacacggaa acttggctca                                              20

<210> SEQ ID NO 2
<211> LENGTH: 22
<212> TYPE: DNA
<213> ORGANISM: artificial sequence
<220> FEATURE:
<223> OTHER INFORMATION: Primer

<400> SEQUENCE: 2
ccagggttga tgtgagtcct ac                                              22

<210> SEQ ID NO 3
<211> LENGTH: 20
<212> TYPE: DNA
<213> ORGANISM: artificial sequence
<220> FEATURE:
<223> OTHER INFORMATION: Primer

<400> SEQUENCE: 3
aacttcgaag cagctgttgg                                                 20

<210> SEQ ID NO 4
<211> LENGTH: 20
<212> TYPE: DNA
<213> ORGANISM: artificial sequence
<220> FEATURE:
<223> OTHER INFORMATION: Primer

<400> SEQUENCE: 4
tggcttccag tggtcgtaat                                                 20

<210> SEQ ID NO 5
<211> LENGTH: 20
<212> TYPE: DNA
<213> ORGANISM: artificial sequence
<220> FEATURE:
<223> OTHER INFORMATION: Primer

<400> SEQUENCE: 5
agatcttcca cagcccagac                                                 20

<210> SEQ ID NO 6
<211> LENGTH: 20
<212> TYPE: DNA
<213> ORGANISM: artificial sequence
<220> FEATURE:
<223> OTHER INFORMATION: Primer

<400> SEQUENCE: 6
ggcgtcactg ttgttgctta                                                 20

<210> SEQ ID NO 7
<211> LENGTH: 20
<212> TYPE: DNA
<213> ORGANISM: artificial sequence
<220> FEATURE:
<223> OTHER INFORMATION: Primer

<400> SEQUENCE: 7
ttgggcatca ctcaggctaa                                                 20

<210> SEQ ID NO 8
<211> LENGTH: 20
<212> TYPE: DNA
<213> ORGANISM: artificial sequence
<220> FEATURE:
<223> OTHER INFORMATION: Primer

<400> SEQUENCE: 8
cccagttgaa agctgcacat                                                 20

<210> SEQ ID NO 9
<211> LENGTH: 20
<212> TYPE: DNA
<213> ORGANISM: artificial sequence

```
<220> FEATURE:
<223> OTHER INFORMATION: Primer

<400> SEQUENCE: 9
cagagacagc agagcacaca                                                    20

<210> SEQ ID NO 10
<211> LENGTH: 20
<212> TYPE: DNA
<213> ORGANISM: artificial sequence
<220> FEATURE:
<223> OTHER INFORMATION: Primer

<400> SEQUENCE: 10
gtgagatggt tccttccggt                                                    20

<210> SEQ ID NO 11
<211> LENGTH: 20
<212> TYPE: DNA
<213> ORGANISM: artificial sequence
<220> FEATURE:
<223> OTHER INFORMATION: Primer

<400> SEQUENCE: 11
cgctctctgc tcctcctgtt                                                    20

<210> SEQ ID NO 12
<211> LENGTH: 20
<212> TYPE: DNA
<213> ORGANISM: artificial sequence
<220> FEATURE:
<223> OTHER INFORMATION: Primer

<400> SEQUENCE: 12
ccatggtgtc tgagcgatgt                                                    20

<210> SEQ ID NO 13
<211> LENGTH: 2166
<212> TYPE: DNA
<213> ORGANISM: Homo sapiens

<400> SEQUENCE: 13
agaattcttt ggcaggggcg accttagaat cctggggagg agcgagaatg gaatcccggg        60
gaggaacagg ggtggaatcc gggggcgggg tcagaacgc caggaggggg cggggccgga       120
gccagggtcg gcttgactcg ggggagcagc gggtggatcc tgtgacgtca gcgggttcga       180
accgccggag ctgagcgaga ggccgggggt gccgagccgg gcggggagag ctgggccggg       240
agagcagaac agggaggcta gagcgcagcg ggaaccggcc cggagccgga gccggagccc       300
cacaggcacc tactaaaccg cccagccgat cggcccccac agagtggccc gcgggcctcc       360
ggccgggccc agtcccctcc cgggccctcc atggcccggg ccgctgccct cctgccgtcg       420
agatcgccgc cgacgccgct gctgtggccg ctgctgctgc tgctgctcct ggaaaccgga       480
gcccaggatg tgcgagttca agtgctaccc gaggtgcgag gccagctcgg gggcaccgtg       540
gagctgccgt gccacctgct gccacctgtt cctggactgt acatctccct ggtgacctgg       600
cagcgcccag atgcacctgc gaaccaccag aatgtggccg ccttccaccc taagatgggt       660
cccagcttcc ccagcccgaa gcctggcagc gagcggctgt ccttcgtctc tgccaagcag       720
agcactgggc aagacacaga ggcagagctc caggacgcca cgctggccct ccacgggctc       780
acggtggagg acgagggcaa ctacacttgc gagtttgcca ccttccccaa ggggtccgtc       840
```

| | |
|---|---|
| cgagggatga cctggctcag agtcatagcc aagcccaaga accaagctga ggcccagaag | 900 |
| gtcacgttca gccaggaccc tacgacagtg gccctctgca tctccaaaga gggccgccca | 960 |
| cctgcccgga tctcctggct ctcatccctg gactgggaag ccaaagagac tcaggtgtca | 1020 |
| gggaccctgg ccggaactgt cactgtcacc agccgcttca ccttggtgcc ctcgggccga | 1080 |
| gcagatggtg tcacggtcac ctgcaaagtg gagcatgaga gcttcgagga accagccctg | 1140 |
| atacctgtga ccctctctgt acgctaccct cctgaagtgt ccatctccgg ctatgatgac | 1200 |
| aactggtacc tcggccgtac tgatgccacc ctgagctgtg acgtccgcag caacccagag | 1260 |
| cccacgggct atgactggag cacgacctca ggcaccttcc cgacctccgc agtggcccag | 1320 |
| ggctcccagc tggtcatcca cgcagtggac agtctgttca ataccacctt cgtctgcaca | 1380 |
| gtcaccaatg ccgtgggcat gggccgcgct gagcaggtca tctttgtccg agaaacccc | 1440 |
| agggcctcgc cccgagatgt gggcccgctg gtgtgggggg ccgtgggggg gacactgctg | 1500 |
| gtgctgctgc ttctggctgg ggggtccttg gccttcatcc tgctgagggt gaggaggagg | 1560 |
| aggaagagcc ctggaggagc aggaggagga gccagtggcg acgggggatt ctacgatccg | 1620 |
| aaagctcagg tgttgggaaa tggggacccc gtcttctgga caccagtagt ccctggtccc | 1680 |
| atggaaccag atggcaagga tgaggaggag gaggaggagg aagagaaggc agagaaaggc | 1740 |
| ctcatgttgc ctccacccc agcactcgag gatgacatgg agtcccagct ggacggctcc | 1800 |
| ctcatctcac ggcgggcagt ttatgtgtga cctggacaca gacagagaca gagccaggcc | 1860 |
| cggccctccc gccccgacc tgaccacgcc ggcctagggt tccagactgg ttggacttgt | 1920 |
| tcgtctggac gacactggag tggaacactg cctcccactt tcttgggact tggagggagg | 1980 |
| tggaacagca cactggactt ctcccgtctc tagggctgca tggggagccc ggggagctga | 2040 |
| gtagtgggga tccagagagg accccgccc cagagactt ggttttggct ccagccttcc | 2100 |
| cctggccccg tgacactcag gagttaataa atgccttgga ggaaaacatc aaaaaaaaaa | 2160 |
| aaaaaa | 2166 |

<210> SEQ ID NO 14
<211> LENGTH: 5160
<212> TYPE: DNA
<213> ORGANISM: Homo sapiens

<400> SEQUENCE: 14

| | |
|---|---|
| aaaacccgga ggagcgggat ggcgcgcttt gactctggag tgggagtggg agcgagcgct | 60 |
| tctgcgactc cagttgtgag agccgcaagg gcatgggaat tgacgccact caccgacccc | 120 |
| cagtctcaat ctcaacgctg tgaggaaacc tcgactttgc caggtcccca agggcagcgg | 180 |
| ggctcggcga gcgaggcacc cttctccgtc cccatcccaa tccaagcgct cctggcactg | 240 |
| acgacgccaa gagactcgag tgggagttaa agcttccagt gagggcagca ggtgtccagg | 300 |
| ccgggcctgc gggttcctgt tgacgtcttg ccctaggcaa aggtcccagt tccttctcgg | 360 |
| agccggctgt ccccgcgcca ctggaaaccgc acctccccgc agcatgggca ccagcctcag | 420 |
| cccgaacgac ccttggccgc taaacccgct gtccatccag cagaccacgc tcctgctact | 480 |
| cctgtcggtg ctggccactg tgcatgtggg ccagcggctg ctgaggcaac ggaggcggca | 540 |
| gctccggtcc gcgcccccgg gccgttttgc gtggccactg atcggaaacg cggcggcggt | 600 |
| gggccaggcg gctcacctct cgttcgctcg cctggcgcgg cgctacggcg acgttttcca | 660 |
| gatccgcctg ggcagctgcc ccatagtggt gctgaatggc gagcgcgcca tccaccaggc | 720 |
| cctggtgcag cagggctcgg ccttcgccga ccggccggcc ttcgcctcct tccgtgtggt | 780 |

```
gtccggcggc cgcagcatgg cttcggcca ctactcggag cactggaagg tgcagcggcg    840
cgcagcccac agcatgatgc gcaacttctt cacgcgccag ccgcgcagcc gccaagtcct    900
cgagggccac gtgctgagcg aggcgcgcga gctggtggcg ctgctggtgc gcggcagcgc    960
ggacggcgcc ttcctcgacc cgaggccgct gaccgtcgtg gccgtggcca acgtcatgag   1020
tgccgtgtgt ttcggctgcc gctacagcca cgacgacccc gagttccgtg agctgctcag   1080
ccacaacgaa gagttcgggc gcacggtggg cgcgggcagc ctggtggacg tgatgccctg   1140
gctgcagtac ttccccaacc cggtgcgcac cgttttccgc gaattcgagc agctcaaccg   1200
caacttcagc aacttcatcc tggacaagtt cttgaggcac tgcgaaagcc ttcggcccgg   1260
ggccgccccc cgcgacatga tggacgcctt tatcctctct gcggaaaaga aggcggccgg   1320
ggactcgcac ggtggtggcg cgcggctgga tttggagaac gtaccggcca ctatcactga   1380
catcttcggc gccagccagg acaccctgtc caccgcgctg cagtggctgc tcctcctctt   1440
caccaggtat cctgatgtgc agactcgagt gcaggcagaa ttggatcagg tcgtggggag   1500
ggaccgtctg ccttgtatgg gtgaccagcc caacctgccc tatgtcctgg ccttccttta   1560
tgaagccatg cgcttctcca gctttgtgcc tgtcactatt cctcatgcca ccactgccaa   1620
cacctctgtc ttgggctacc acattcccaa ggacactgtg gttttgtca accagtggtc   1680 tgtgaatcat gacccactga gtggcctaa cccggagaac tttgatccag ctcgattctt   1740
ggacaaggat ggcctcatca acaaggacct gaccagcaga gtgatgattt ttcagtggg   1800 caaaaggcgg tgcattggcg aagaactttc taagatgcag ctttttctct tcatctccat   1860
cctggctcac cagtgcgatt tcagggccaa cccaaatgag cctgcgaaaa tgaatttcag   1920
ttatggtcta accattaaac ccaagtcatt taaagtcaat gtcactctca gagagtccat   1980
ggagctcctt gatagtgctg tccaaaattt acaagccaag gaaacttgcc aataagaagc   2040
aagaggcaag ctgaaatttt agaaatattc acatcttcgg agatgaggag taaaattcag   2100 ttttttttcca gttcctcttt tgtgctgctt ctcaattagc gtttaaggtg agcataaatc   2160
aactgtccat caggtgaggt gtgctccata cccagcggtt cttcatgagt agtgggctat   2220
gcaggagctt ctgggagatt tttttgagtc aaagacttaa agggcccaat gaattattat   2280
atacatactg catcttggtt atttctgaag gtagcattct ttggagttaa aatgcacata   2340
tagacacata cacccaaaca cttacaccaa actactgaat gaagcagtat tttggtaacc   2400
aggccatttt tggtgggaat ccaagattgg tctcccatat gcagaaatag acaaaaagta   2460
tattaaacaa agtttcagag tatattgttg aagagacaga gacaagtaat ttcagtgtaa   2520
agtgtgtgat tgaaggtgat aagggaaaag ataaagacca gaaattccct tttcaccttt   2580
tcaggaaaat aacttagact ctagtattta tgggtggatt tatccttttg ccttctggta   2640
tacttcctta cttttaagga taaatcataa agtcagttgc tcaaaagaa atcaatagtt   2700 gaattagtga gtatagtggg gttccatgag ttatcatgaa ttttaaagta tgcattatta   2760
aattgtaaaa ctccaaggtg atgttgtacc tctttgctt gccaaagtac agaatttgaa   2820
ttatcagcaa agaaaaaaaa aaagccagc caagctttaa attatgtgac cataatgtac   2880
tgatttcagt aagtctcata ggttaaaaaa aaagtcacc aaatagtgtg aaatatatta   2940
cttaactgtc cgtaagcagt atattagtat tatcttgttc aggaaaaggt tgaataatat   3000
atgccttgta taatattgaa aattgaaaag tacaactaac gcaaccaagt gtgctaaaaa   3060
tgagcttgat taaatcaacc acctatttt gacatggaaa tgaagcaggg tttcttttct   3120
```

-continued

```
tcactcaaat tttggcgaat ctcaaaatta gatcctaaga tgtgttctta tttttataac    3180
atctttattg aaattctatt tataatacag aatcttgttt tgaaaataac ctaattaata    3240
tattaaaatt ccaaattcat ggcatgctta aatttttaact aaatttttaaa gccattctga  3300 ttattgagtt ccagttgaag ttagtggaaa tctgaacatt ctcctgtgga aggcagagaa    3360
atctaagctg tgtctgccca tgaataatg gaaaatgcca tgaattacct ggatgttctt     3420
tttacgaggt gacaagagtt ggggacagaa ctcccattac aactgaccaa gtttctcttc    3480
tagatgattt tttgaaagtt aacattaatg cctgcttttt ggaaagtcag aatcagaaga    3540
tagtcttgga agctgtttgg aaaagacagt ggagatgagg tcagttgtgt tttttaagat    3600
ggcaattact ttggtagctg ggaaagcata aagctcaaat gaaatgtatg cattcacatt    3660
tagaaaagtg aattgaagtt tcaagtttta aagttcattg caattaaaact tccaaagaaa   3720 gttctacagt gtcctaagtg ctaagtgctt attacatttt attaagcttt ttggaatctt    3780
tgtaccaaaa ttttaaaaaa gggagttttt gatagttgtg tgtatgtgtg tgtggggtgg    3840
ggggatggta agagaaaaga gagaaacact gaaaagaagg aaagatggtt aaacattttc    3900
ccactcattc tgaattaatt aatttggagc acaaaattca aagcatggac atttagaaga    3960
aagatgtttg gcgtagcaga gttaaatctc aaataggcta ttaaaaaagt ctacaacata    4020
gcagatctgt tttgtggttt ggaatattaa aaaacttcat gtaattttat tttaaaattt    4080
catagctgta cttcttgaat ataaaaaatc atgccagtat ttttaaaggc attagagtca    4140
actacacaaa gcaggcttgc ccagtacatt taaattttt ggcacttgcc attccaaaat     4200
attatgcccc accaaggctg agacagtgaa tttgggctgc tgtagcctat tttttttagat   4260 tgagaaatgt gtagctgcaa aaataatcat gaaccaatct ggatgcctca ttatgtcaac    4320
caggtccaga tgtgctataa tctgttttta cgtatgtagg cccagtcgtc atcagatgct    4380
tgcggcaaaa ggaaagctgt gtttatatgg aagaaagtaa ggtgcttgga gtttacctgg    4440
cttatttaat atgcttataa cctagttaaa gaaggaaaa gaaaacaaaa aacgaatgaa     4500
aataactgaa tttggaggct ggagtaatca gattactgct ttaatcagaa accctcattg    4560
tgtttctacc ggagagagaa tgtatttgct gacaaccatt aaagtcagaa gttttactcc    4620
aggttattgc aataaagtat aatgtttatt aaatgcttca tttgtatgtc aaagctttga    4680
ctctataagc aaattgcttt ttccaaaaac aaaaagatgt ctcaggtttg ttttgtgaat    4740
tttctaaaag ctttcatgtc ccagaactta gcctttacct gtgaagtgtt actacagcct    4800
taatattttc ctagtagatc tatattagat caaatagttg catagcagta tatgttaatt    4860
tgtgtgtttt tagctgtgac acaactgtgt gattaaaagg tatactttag tagacattta    4920
taactcaagg ataccttctt atttaatctt ttcttatttt tgtactttat catgaatgct    4980
tttagtgtgt gcataatagc tacagtgcat agttgtagac aaagtacatt ctggggaaac    5040
aacatttata tgtagccttt actgtttgat ataccaaatt aaaaaaaaat tgtatctcat    5100
tacttatact gggacaccat taccaaaata ataaaaatca ctttcataat cttgaaaaaa    5160
```

<210> SEQ ID NO 15
<211> LENGTH: 2238
<212> TYPE: DNA
<213> ORGANISM: Homo sapiens

<400> SEQUENCE: 15

```
aaaggacttg tttcctgctg aaaaagcaga aagagattac cagccacaga cgggtcatga              60
gcgcggtatt actgctggcc ctcctggggt tcatcctccc actgccagga gtgcaggcgc             120
```

```
tgctctgcca gtttgggaca gttcagcatg tgtggaaggt gtccgacctg ccccggcaat    180 ggaccccta  gaacaccagc tgcgacagcg gcttggggtg ccaggacacg ttgatgctca    240
ttgagagcgg accccaagtg agcctggtgc tctccaaggg ctgcacggag gccaaggacc    300
aggagccccg cgtcactgag caccggatgg gccccggcct ctccctgatc tcctacacct    360
tcgtgtgccg ccaggaggac ttctgcaaca acctcgttaa ctccctcccg ctttgggccc    420
cacagccccc agcagaccca ggatccttga ggtgcccagt ctgcttgtct atggaaggct    480
gtctggaggg gacaacagaa gagatctgcc ccaaggggac cacacactgt tatgatggcc    540
tcctcaggct caggggagga ggcatcttct ccaatctgag agtccaggga tgcatgcccc    600
agccagtttg caacctgctc aatgggacac aggaaattgg gcccgtgggt atgactgaga    660
actgcgatat gaaagatttt ctgacctgtc atcgggggac caccattatg acacacggaa    720
acttggctca agaacccact gattggacca catcgaatac cgagatgtgc gaggtggggc    780
aggtgtgtca ggagacgctg ctgctcctag atgtaggact cacatcaacc ctggtgggga    840
caaaaggctg cagcactgtt ggggctcaaa attcccagaa gaccaccatc cactcagccc    900
ctcctggggt gcttgtggcc tcctataccc acttctgctc ctcggacctg tgcaatagtg    960
ccagcagcag cagcgttctg ctgaactccc tccctcctca agctgcccct gtcccaggag   1020
accggcagtg tcctacctgt gtgcagcccc ttggaacctg ttcaagtggc tcccccgaa    1080 tgacctgccc caggggcgcc actcattgtt atgatgggta cattcatctc tcaggaggtg   1140
ggctgtccac caaaatgagc attcagggct gcgtggccca accttccagc ttcttgttga   1200
accacaccag acaaatcggg atcttctctg cgcgtgagaa gcgtgatgtg cagcctcctg   1260
cctctcagca tgagggaggt ggggctgagg gcctggagtc tctcacttgg ggggtggggc   1320
tggcactggc cccagcgctg tggtggggag tggtttgccc ttcctgctaa ctctattacc   1380
cccacgattc ttcaccgctg ctgaccaccc acactcaacc tccctctgac ctcataacct   1440
aatggccttg acaccagat  tctttcccat tctgtccatg aatcatcttc cccacacaca   1500
atcattcata tctactcacc taacagcaac actggggaga gcctggagca tccggacttg   1560
ccctatggga gaggggacgc tggaggagtg gctgcatgta tctgataata cagaccctgt   1620
cctttctccc agtgctggga tttctccatg tgagggggca gcaggacacc cagggatcta   1680
gcgtggggga ggagaggagc ctaatgagaa aatgaccatc taaagcctgc ccttcattgg   1740
tctggttcac gtctccaaac cagcttggat ggtagcagag acttcagggt gctccagcca   1800
aacgtatttg ggcatcacca tgacctggga ggggaagatg cactgagacg tatgaggctt   1860
ccagcctagc agccagggcc ctagcacaaa caggaggctc gccccatctg agcaactgca   1920
ggagaggtta gtacagtcat gcattgctta acgacaggga cgtgtcgtta gaatgtgtc    1980 gttaggtgat tttatgacca taggaacatt gtagcgtgca cttacaccaa cccagatggt   2040
acagcccaat acacacccag gatggacgct agagtcgact gctcctaggc tacaagcctg   2100
cagtgcatgt tatggtgtga atactgcagg caatcttaac accacggcaa gtatttgtgc   2160
atctacacac atctaaacat agaaaaggta cagcataaat acactattgt catctcagca   2220
gaaaaaaaaa aaaaaaaa                                                 2238
```

<210> SEQ ID NO 16
<211> LENGTH: 2103
<212> TYPE: DNA
<213> ORGANISM: Homo sapiens

<400> SEQUENCE: 16

```
tcccgcggcg gctggcgtcg ggaaagtaca gtaaaaagtc cgagtgcagc cgccgggcgc      60
aggatgggat ccggctcctc cagctaccgg cccaaggcca tctacctgga catcgatgga     120
cgcattcaga aggtaatctt cagcaagtac tgcaactcca cgacatcat ggacctgttc      180
tgcatcgcca ccggcctgcc tcggaacacg accatctccc tgctgaccac cgacgacgcc     240
atggtctcca tcgaccccac catgcccgcg aattcagaac gcactccgta caaagtgaga     300
cctgtggcca tcaagcaact ctccgctggt gtcgaggaca agagaaccac aagccgtggc     360
cagtctgctg agagaccact gagggacaga cggggttgtgg gcctggagca gccccggagg     420
gaaggagcat ttgaaagtgg acaggtagag cccaggccca gagagcccca gggctgctac     480
caggaaggcc agcgcatccc tccagagaga aagaattaa ccagagcgt gctggcgcag       540
gttgcagagc agttctcaag agcattcaaa atcaatgaac tgaaagctga agttgcaaat     600
cacttggctg tcctagagaa acgcgtggaa ttggaaggac taaaagtggt ggagattgag     660
aaatgcaaga gtgacattaa aagatgagg gaggagctgg cggccagaag cagcaggacc      720
aactgccct gtaagtacag ttttttggat aaccacaaga agttgactcc tcgacgcgat      780
gttcccactt accccaagta cctgctctct ccagagacca tcgaggccct gcggaagccg     840
acctttgacg tctggctttg ggagcccaat gagatgctga gctgcctgga gcacatgtac     900
cacgacctcg ggctggtcag ggacttcagc atcaaccctg tcaccctcag gaggtggctg     960
ttctgcgtcc acgacaacta cagaaacaac cccttccaca acttccggca ctgcttctgc    1020
gtggcccaga tgatgtacag catggtctgg ctctgcagtc tccaggagaa gttctcacaa    1080
acggatatcc tgatcctaat gacagcggcc atctgccacg atctggacca tcccggctac    1140
aacaacacgt accagatcaa tgcccgcaca gagctggcgg tccgctacaa tgacatctca    1200
ccgctggaga accaccactg cgccgtggcc ttccagatcc tcgccgagcc tgagtgcaac    1260
atcttctcca acatcccacc tgatgggttc aagcagatcc gacagggaat gatcacatta    1320
atcttggcca ctgacatggc aagacatgca gaaattatgg attctttcaa agagaaaatg    1380
gagaattttg actacagcaa cgaggagcac atgaccctgc tgaagatgat tttgataaaa    1440
tgctgtgata tctctaacga ggtccgtcca atggaagtcg cagagccttg ggtggactgt    1500
ttattagagg aatattttat gcagagcgac cgtgagaagt cagaaggcct tcctgtggca    1560
ccgttcatgg accgagacaa agtgaccaag gccacagccc agattgggtt catcaagttt    1620
gtcctgatcc caatgtttga aacagtgacc aagctcttcc ccatggttga ggagatcatg    1680
ctgcagccac tttgggaatc ccgagatcgc tacgaggagc tgaagcggat agatgacgcc    1740
atgaaagagt acagaagaa gactgacagc ttgacgtctg gggccaccga aagtccaga     1800
gagagaagca gagatgtgaa aacagtgaa ggagactgtg cctgaggaaa gcggggggcg    1860
tggctgcagt tctggacggg ctggccgagc tgcgcgggat ccttgtgcag ggaagagctg    1920
ccctgggcac ctggcaccac aagaccatgt tttctaagaa ccatttttgtt cactgataca    1980
aaaaaaaaaa aaggaattca tgatgctgta cagaattta tttttaaact gtctttaaa     2040
taatatattc ttatacggaa aaaaaaaaaa aaaaaaaaaa aaaaaaaaaa aaaaaaaaa     2100
aaa                                                                 2103
```

<210> SEQ ID NO 17
<211> LENGTH: 1231
<212> TYPE: DNA
<213> ORGANISM: Homo sapiens

<400> SEQUENCE: 17

```
agagttctgg ttccggaagg ccccccacag gtgccttggg cctagctctc acctgggccc        60
agggcaacac tgaagacatg ggcaagagca tcccccaata cctggggcaa ctggacatcc       120
gcaaaagcgt agtcagcctg ccacaggcg ccggggcgat ctacctgctc tacaaggcca       180
tcaaggctgg cataaaatgc aaaccacccc tctgtagcaa ctcacccatc tgcatcgccc       240
gtgagtgtcc gggccctggg gagagggctc tgccccagga ggcacctgct cccgaggcct       300
ctgctgtggg agggcccaaa ggcctggcag tcgagcgaga gcggcacggg cgggactcag       360
gtgagctccg gaggctcctc aactcttttgg agtgcaaaca ggatgagtat gccaagagca       420
tgatcctgca cagtatcact cgctgtgtgt acttgctgga ggctgaggcc tctgcttgta       480
ctacggatga catcgtgttg ctgggctaca tgctggatga caaggacaac agtgtcaaaa       540
cccaagctct gaatacactt aaagctttct ctggcatcag aaaattcagg ctcaaaatcc       600
aggaacactc catcaaagta ctcgaactga tctccaccat ctgggacacg gaactgcaca       660
ttgcgggcct cagactcctc aacaaccttc cactgcccga ctatgtgcat ccacagctgc       720
gacgggtgat gcctgccttg atggagatcc tgcagtcaga ctacatcctg gcacaggtgc       780
aagccgtacg actgctgagc tacctggcac agaagaatga ccttctctat gacattctca       840
actgccaggt tcactccaac ttcctaaacc tgttccagcc cacacagtca gggagtctcc       900
tgtatgaggt actggtgttt gctgagcggc tgagtgaggg ccggaacgca ccccactacc       960
acgtggtgaa atggcattac aacgaacagt ccctgcatga atccctcttt ggggaagagt      1020
cccgactggc agaccgacta cttgccctgg tcatccaccc tgaggaagat gttcagatcc      1080
aggcctgcaa ggtcattgtc agcctgcagt atccccagga cttgagagcc ggccctcct      1140
cctgccagcc cagtcgttcc tactttaaaa acacggaata aaattaagga gagccaataa      1200
atgagtatag gagagaaact tgaaaaaaaa a                                      1231
```

<210> SEQ ID NO 18
<211> LENGTH: 1834
<212> TYPE: DNA
<213> ORGANISM: Homo sapiens

<400> SEQUENCE: 18

```
acctcatttc ctgtgtcctc tctttctttg gcaatccaaa gaaagtcatc tttcagattg        60
tctgctcaga gttcatctca aagcctggca aggattggag aggtcaataa gagtcagcgc       120
cttaaaaaag aaatctactc actcttctgt gtgcataagg ccgagcagag gttcttcgtc       180
tcaagaggaa ctgacttctg ttgagcactc aacacgccac agagaccagc catcttgcaa       240
cctcacctca cagcatggag agaggagacc aacctaagag aaccaggaat gaaaacattt       300
tcaactgctt atacaaaaac cctgaggcaa cttttaagct gatttgcttt ccctggatgg       360
gaggtggctc cactcatttt gccaaatggg gccaagatac tcatgatttg ctggaagaga       420
cagcatctca ccatgttgcc aaggctggtc tcaaactccg gcgctcaagt gatcctcctg       480
cttcagccta cccatgtgct ggcgtgagcc accgtaggcg tgagccaccg tgcctggcca       540
aaattcttgg tctattctgg attctaattt tttttatgca ctccttaagg cttcctggaa       600
gagaaagcag agttgaagaa cctcttgaaa atgacatctc ccagttagtt gatgaagttg       660
tttgtgctct gcagccagtc atccaggata aaccatttgc atttttttggc cacagtatgg       720
gatcctacat tgcttttagg actgcactag gtctaaaaga aaacaatcaa ccagaaccat       780
```

| | |
|---|---|
| tgcatttatt tttgtcaagt gcaactcctg tacattcaaa ggcctggcat cgcattccca | 840 |
| aagatgatga attgtcagaa gaacaaataa gtcattacct tatggaattt ggaggcaccc | 900 |
| ccaagcattt tgctgaagcc aaggaatttg tgaaacaatg tagtcccatc ataagggcag | 960 |
| atctgaacat tgttagaagt tgcacctcta acgtaccatc taaggctgtt ctttcctgtg | 1020 |
| acttgacatg ttttgttgga tctgaagaca tagcaaagga catggaagcc tggaaagatg | 1080 |
| taaccagtgg aaatgctaaa atttaccagc ttccagggg tcactttat cttctggatc | 1140 |
| ctgcgaacga gaaattaatc aagaactaca taatcaagtg tctagaagta tcatcgatat | 1200 |
| ccaattttta gatattttcc ctttcacttt taaaataatc aaagtaatat catactcttc | 1260 |
| tcagttattc agatatagct cagttttatt cagattggaa attacacatt ttctactgtc | 1320 |
| agggagattc gttacataaa tatatttacg tatctgggga caaaggtcaa gccagtaaag | 1380 |
| aatacttctg gcagcacttt gggaggccaa ggcgggcgga tcacgaggtc aggagatcga | 1440 |
| gaccgtcctg gctaacaccg tgaaacccca tctctactaa aaatacacaa aattagccgg | 1500 |
| gcgtggtggt gggcacctgt agtcccagct actcggagg ctgaggcagg agaatggtgt | 1560 |
| gaacctggga ggtggagctt gcagtgaacc gagatcgctc cactgcactc cagcctgggt | 1620 |
| gacagatcca gactctgtct caaaaaaaaa aaaaaaaaaa atacttctgg cagagtcttt | 1680 |
| tatcttccta ttaaaatctc acttgattct cctttatggg aagtttgtcg acaaaattca | 1740 |
| tgattagtaa attatccatt ttttccttca gttagtttaa tggtgaagat gattaacagg | 1800 |
| ggaaatgctt gaagtaaatg attgtttcaa tggc | 1834 |

<210> SEQ ID NO 19
<211> LENGTH: 4691
<212> TYPE: DNA
<213> ORGANISM: Homo sapiens

<400> SEQUENCE: 19

| | |
|---|---|
| ataggcgggg gcaggggcag gggcagctct cctttacct agagcggcga cagaagctct | 60 |
| tcggggatc agtggccaag ggggcggaca gatttgcacg gcggattcct ccgaagcaac | 120 |
| ccgtgtgaaa gaagccaagc ggcggctgca gcccggcccg cgatgggggt gacaccgccc | 180 |
| gtggtcccgc cccttcccgt ggcccctcgg agccacttcc ggcggcagcg tccgggctag | 240 |
| ttcccggcgc gagcggccgc gggccagttt ctatctcctc atccaggct tgcgggcgag | 300 |
| gcctgtttta agtctccagt aaccgagcgg aggcccggca ggcgcgaccc gggctgcgta | 360 |
| cgtcagagct gcctccgaag tggtaaaatg tgctgcgaga agtggagccg cgtgcggaa | 420 |
| atgtttctct tcattgagga gcgggaggat tgtaagatac tgtgcctttg ctccagggca | 480 |
| tttgtggagg atcgaaaatt gtacaatttg ggattaaaag gctattacat cagagacagt | 540 |
| ggcaacaatt caggagacca ggcgacagaa gaagaggaag gtggttattc ctgtggtact | 600 |
| gcagaatcac atgacagcaa aggcataggc ctggatgaaa gtgaacttga ttctgaggct | 660 |
| gaactcatga gaagtatggg attgccactt caatttggta ggataactgc acataaggat | 720 |
| tttgaggtat ctatgaatac tagaaataaa gttaaaataa aaagaaaaa acatcaaaag | 780 |
| aaatacttag atgaaattgt gcaagaatct tggagaaaag aatatgaaga agacgacatt | 840 |
| ttggcttcag atgatccatc ttcaattgaa cagtatgaga acaccagaac atatgaactt | 900 |
| caaagcaaaa aagatactga gacagaaaat cctccagttg aaaacacatt atctccaaag | 960 |
| ctagaaaatta cagagaaatg ggaaaagtat tggaatgaat atgaggagg actattgtgg | 1020 |
| caaagttggc aagaaaaaca tccgggtcaa gcactatctt ctgaaccttg gactttcct | 1080 |

```
gatacaaagg aagaatggga gcaacattat agtcaacttt attggtatta tttggaacaa    1140
tttcagtatt gggaagctca gggttggact tttgatgcct cgcaaagctg tgatacagat    1200
acttacacat ctaaaacaga agctgatgac aagaacgatg aaaaatgcat gaaagttgac    1260
ttagtatctt ttccatcttc acctattatg gttgataatg atagctctgg tacaagtgat    1320
aaggatcata gtgaaatact tgatggaatt agtaacataa aactgaattc agaggaagta    1380
acacagagcc aattagattc ctgtacaagt catgatggtc atcaacagct aagtgaagtt    1440
agtagcaaaa gagagtgccc tgcttccggc caaagtgaac cacgtaatgg aggaaccaat    1500
gaggaaagca actcatcggg gaatacaaac acagacccac cagctgagga ttcacagaag    1560
tcttcaggag caaacacaag caaagacaga ccacatgcca gtggtactga tggagatgaa    1620
agtgaggaag accccacctga gcataagcca agcaaactga agaggagcca tgaactggac    1680
attgatgaaa acccagcttc agactttgat gacagtggtt cccttctagg attcaagtat    1740
ggctcaggac aaaaatatgg tggaatccca aatttcagtc atcggcaggt caggtattta    1800
gagaagaatg tgaagcttaa gtctaagtac ctagacatgc gcagacaaat aaagatgaaa    1860
aacaaacaca tcttctttac caaagagtca gaaaaaccat ttttcaagaa aagcaaaatt    1920
ctgagtaagg tagaaaaatt cctcacatgg gttaataaac caatggatga agaagcatca    1980
caggaatcat cttctcatga caatgtgcac gacgcttcca caagtagtga ttcagaggaa    2040
caagacatgt ctgttaaaaa aggtgatgac ctactggaga ctaataatcc agaacctgaa    2100
aagtgtcaga gcgtatcttc agctggtgaa cttgaaacag aaaactatga agagacagc     2160 ttgctagcaa ctgttccaga tgagcaggat tgtgttactc aagaagtgcc agactcccgc    2220
caggcagaaa ctgaagctga agtgaaaaag aagaagaaca agaagaagaa caaaaaggtg    2280
aatggtctgc ctcctgaaat agctgctgtt cctgagctgg caaaatactg ggcccagagg    2340
tacaggctct tctcccgttt tgatgatggg attaagttgg acagagaggg ctggttttca    2400
gttacacccg agaagattgc tgaacacatt gctggccgtg ttagtcagtc cttcaagtgt    2460
gacgttgtag tagacgcatt ctgtggagtt ggaggaaata ccattcagtt tgccttaaca    2520
ggaatgagag tgattgccat tgatatcgat cctgttaaga ttgcccttgc tcgcaataat    2580
gcagaagttt atgggatagc agataagata gagttcatct gtggagattt cttgctgctg    2640
gcttcttttt taaaggctga tgttgtgttc ctcagcccac cttggggagg gccagactat    2700
gccactgcag agacctttga cattagaaca atgatgtctc ctgatggctt tgaaattttc    2760
agactttcta agaagatcac taataatatt gtttatttc ttccaagaaa tgctgatatt    2820
gaccaggtgg catccttagc tgggcctgga gggcaagtgg aaatagaaca gaacttcctt    2880
aacaacaaat tgaagacaat cactgcatat tttggtgacc taattcgaag accagcctct    2940
gaaacctaac tatgcagcag tgcgaggaca aaagatcatg gagtggtcaa atattcaga     3000 tgagacattt ggcatgtctt cctttattca ctgatatttt ctacccatgg tcttatatca    3060
ccgtatgaaa tggaaactta caggacttaa atatcagtga atattttga gatctttgaa      3120 taattccttt agaggaatta tacaaaatta atatatatga gtcctttgta atttattttt     3180
ttttgagaca ggatctcact tttaccgccc aggctggagt gcagtgccat gatcacagct    3240
cactgcaggt tcagccttct gagttcaagc aatccttctg tctcagtctc ctcagtagct    3300
ggggctttag gtgggcactg ccacaccgta ctaattttg tattttttgt agagacgagg      3360
tcccaccatg ttgcccaggc tggtgtcaaa ctcctgggct cagtcagtcc cccatctca    3420
```

| | |
|---|---|
| ccctcccccaa gtgctggaat tacaggcgtg agctactgtg cccagcctta cggacatcct | 3480 |
| tttgaattat cttttttcact catagaatat gaatacattt atttagactt tttctagaac | 3540 |
| tttcctgttt tcatgtcttt gcttcatctg gaattggctt aacacccttt tataaagttt | 3600 |
| gtgtttgtaa aatttccatt gtgacatcaa tacgcaatat attttgtaat ataggagttt | 3660 |
| ctattttttt attaaaatgg caatgaaagc aagagggata tgtgttgctt aattattcat | 3720 |
| ctaaaaagtt tgttcagtca tttttacaag taggcaaaaa aatagtgaca tacaacactt | 3780 |
| gtccattgaa ggttagacct gggacttcta tattttaata atatgagcgt gttaaacatt | 3840 |
| aaacagaaca tgatactggc tgggataaga ttagagaatt gaaacaaatt tggggaattt | 3900 |
| ccaataaata ctagaaaatt agactagaaa aatagctgtt atataaataa ctttgttgga | 3960 |
| atatgctaat tttagtgtct tgaaagttta caatttatct gattgctctg cagtacagta | 4020 |
| gcaactgagc tgatcaataa aggtgaaatt acttttttcat taattcgcaa tttcaaaatc | 4080 |
| tgtccaaatg ttcttggttt ttaaacttta tgtagcattc tttttttttt ttttagacag | 4140 |
| agtcttgctc tgtcgcccag gctggagtgc aatggcgtga tctcagctta ctgcaacctc | 4200 |
| cacctcctac ctcagcctcc cgagtagctg ggactacagg cacctgccac cacatccagc | 4260 |
| taatttttta tattttttagt agctatgggg tttcaccgtg ttagccagga tggtctcgat | 4320 |
| ctcctgacct tgtgatccaa ccacctcagc ctcccgtagt tctgggatta caggcgtgag | 4380 |
| ccaccgcgcc tggctttatg tagcattctt aaagtcacta gggagatggc aggtgaagta | 4440 |
| aaggcagatt tccaaaatca ctaatttttt ttagtttttt gtcacttaac ctttcttgca | 4500 |
| tatacttctt tccacagctc attttcttac ttgtatatta ataaagctaa ctcatcttcc | 4560 |
| tgaatataca tgattttaca tgagaagagc aggaagctta ggcttggtta gctaaaacta | 4620 |
| agatattgct gcccactaat cacacaggga taaaactaat agactgttaa gattgtcagt | 4680 |
| actcaatagg a | 4691 |

<210> SEQ ID NO 20
<211> LENGTH: 4190
<212> TYPE: DNA
<213> ORGANISM: Homo sapiens

<400> SEQUENCE: 20

| | |
|---|---|
| atatgtagcc ttttcatttt catgaaagtg aagtgatttt tagaattctt agttgttttc | 60 |
| tttagaagaa catttctagg gaataataca agaagattta ggaatcattg aagttataaa | 120 |
| tctttggaat gagcaaactc agaatggtgc tacttgaaga ctctggatct gctgacttca | 180 |
| gaagacattt tgtcaacttg agtcccttca ccattactgt ggtcttactt ctcagtgcct | 240 |
| gttttgtcac cagttctctt ggaggaacag acaaggagct gaggctagtg gatggtgaaa | 300 |
| acaagtgtag cgggagagtg gaagtgaaag tccaggagga gtggggaacg gtgtgtaata | 360 |
| atggctggag catggaagcg gtctctgtga tttgtaacca gctgggatgt ccaactgcta | 420 |
| tcaaagcccc tggatgggct aattccagtg caggttctgg acgcatttgg atggatcatg | 480 |
| tttcttgtcg tgggaatgag tcagctcttt gggattgcaa acatgatgga tggggaaagc | 540 |
| atagtaactg tactcaccaa caagatgctg gagtgacctg ctcagatgga tccaatttgg | 600 |
| aaatgaggct gacgcgtgga gggaatatgt gttctggaag aatagagatc aaattccaag | 660 |
| gacggtgggg aacagtgtgt gatgataact tcaacataga tcatgcatct gtcatttgta | 720 |
| gacaacttga atgtgaagt gctgtcagtt tctctggttc atctaatttt ggagaaggct | 780 |
| ctggaccaat ctggtttgat gatcttatat gcaacggaaa tgagtcagct ctctggaact | 840 |

```
gcaaacatca aggatgggga aagcataact gtgatcatgc tgaggatgct ggagtgattt      900
gctcaaaggg agcagatctg agcctgagac tggtagatgg agtcactgaa tgttcaggaa      960
gattagaagt gagattccaa ggagaatggg ggacaatatg tgatgacggc tgggacagtt     1020
acgatgctgc tgtggcatgc aagcaactgg gatgtccaac tgccgtcaca gccattggtc     1080
gagttaacgc cagtaaggga tttggacaca tctggcttga cagcgtttct gccagggac      1140 atgaacctgc tatctggcaa tgtaaacacc atgaatgggg aaagcattat tgcaatcaca     1200
atgaagatgc tggcgtgaca tgttctgatg gatcagatct ggagctaaga cttagaggtg     1260
gaggcagccg ctgtgctggg acagttgagg tggagattca gagactgtta gggaaggtgt     1320
gtgacagagg ctggggactg aaagaagctg atgtggtttg caggcagctg ggatgtggat     1380
ctgcactcaa acatcttat caagtgtact ccaaaatcca ggcaacaaac acatggctgt      1440
ttctaagtag ctgtaacgga aatgaaactt ctctttggga ctgcaagaac tggcaatggg     1500
gtggacttac ctgtgatcac tatgaagaag ccaaaattac ctgctcagcc cacagggaac    1560
ccagactggt tggagggac attccctgtt ctggacgtgt tgaagtgaag catggtgaca      1620 cgtgggctc catctgtgat tcggacttct ctctggaagc tgccagcgtt ctatgcaggg      1680
aattacagtg tggcacagtt gtctctatcc tggggggagc tcactttgga gagggaaatg    1740
gacagatctg ggctgaagaa ttccagtgtg agggacatga gtcccatctt tcactctgcc    1800
cagtagcacc ccgcccagaa ggaacttgta gccacagcag ggatgttgga gtagtctgct    1860
caagatacac agaaattcgc ttggtgaatg caagaccccc gtgtgagggc agagtggagc    1920
tcaaaacgct tggtgcctgg ggatccctct gtaactctca ctgggacata aagatgccc     1980 atgttctttg ccagcagctt aaatgtggag ttgccctttc taccccagga ggagcacgtt    2040
ttggaaaagg aaatggtcag atctggaggc atatgtttca ctgcactggg actgagcagc    2100
acatgggaga ttgtcctgta actgctctag gtgcttcatt atgtccttca gagcaagtgg    2160
cctctgtaat ctgctcagga aaccagtccc aaacactgtc ctcgtgcaat tcatcgtctt    2220
tgggcccaac aaggcctacc attccagaag aaagtgctgt ggcctgcata gagagtggtc    2280
aacttcgcct ggtaaatgga ggaggtcgct gtgctgggag agtagagatc tatcatgagg    2340
gctcctgggg caccatctgt gatgacagct gggacctgag tgatgcccac gtggtttgca    2400
gacagctggg ctgtggagag gccattaatg ccactggttc tgctcatttt ggggaaggaa    2460
cagggcccat ctggctggat gagatgaaat gcaatggaaa agaatcccgc atttggcagt    2520
gccattcaca cggctggggg cagcaaaatt gcaggcacaa ggaggatgcg ggagttatct    2580
gctcagaatt catgtctctg agactgacca gtgaagccag cagagaggcc tgtgcagggc    2640
gtctggaagt tttttacaat ggagcttggg gcactgttgg caagagtagc atgtctgaaa    2700
ccactgtggg tgtggtgtgc aggcagctgg gctgtgcaga caaagggaaa atcaaccctg    2760
catctttaga caaggccatg tccattccca tgtgggtgga caatgttcag tgtccaaaag    2820
gacctgacac gctgtggcag tgcccatcat ctccatggga aagagactg gccagcccct    2880 cggaggagac ctggatcaca tgtgacaaca agataagact tcaggaagga cccacttcct    2940
gttctggacg tgtggagatc tggcatggag gttcctgggg gacagtgtgt gatgactctt    3000
gggacttgga cgatgctcag gtggtgtgtc aacaacttgg ctgtggtcca gctttgaaag    3060
cattcaaaga agcagagttt ggtcagggga ctggaccgat atggctcaat gaagtgaagt    3120
gcaaagggaa tgagtcttcc ttgtgggatt gtcctgccag acgctgggc catagtgagt    3180
```

| | |
|---|---|
| gtgggcacaa ggaagacgct gcagtgaatt gcacagatat ttcagtgcag aaaaccccac | 3240 |
| aaaaagccac aacaggtcgc tcatcccgtc agtcatcctt tattgcagtc gggatccttg | 3300 |
| gggttgttct gttggccatt tcgtcgcat tattcttctt gactaaaaag cgaagacaga | 3360 |
| gacagcggct tgcagtttcc tcaagaggag agaacttagt ccaccaaatt caataccggg | 3420 |
| agatgaattc ttgcctgaat gcagatgatc tggacctaat gaattcctca gaaaattccc | 3480 |
| atgagtcagc tgatttcagt gctgctgaac taatttctgt gtctaaattt cttcctattt | 3540 |
| ctggaatgga aaaggaggcc attctgagcc acactgaaaa ggaaaatggg aatttataac | 3600 |
| ccagtgagtt cagcctttaa gatacccttga tgaagacctg gactattgaa tggagcagaa | 3660 |
| attcacctct ctcactgact attacagttg cattttatg gagttcttct tctcctagga | 3720 |
| ttcctaagac tgctgctgaa tttataaaaa ttaagtttgt gaatgtgact acttagtggt | 3780 |
| gtatatgaga cttttcaaggg aattaaataa ataataaga atgttattga tttgagtttg | 3840 |
| cttttaattac ttgtccttaa ttctattaat ttctaaatgg gcttcctaat tttttgtaga | 3900 |
| gtttcctaga tgtattataa tgtgttttat ttgacagtgt ttcaatttgc atatacagta | 3960 |
| ctgtatattt tttcttattt ggtttgaata attttcctat taccaaataa aaataaattt | 4020 |
| atttttactt tagtttttct aagacaggaa aagttaatga tattgaaggg tctgtaaata | 4080 |
| atatatggct aactttataa ggcatgactc acaacgattc tttaactgct ttttgttact | 4140 |
| gtaattctgt tcactagaat aaaatgcaga gccacacctg gtgagggcac | 4190 |

<210> SEQ ID NO 21
<211> LENGTH: 1529
<212> TYPE: DNA
<213> ORGANISM: Homo sapiens

<400> SEQUENCE: 21

| | |
|---|---|
| agtgagcaat gcaattctgg gaatgttcag gctctctctg ttctttcctc tcttgcaaac | 60 |
| catgggcacc cttgggtccc ttggggtcac tatgttacac ctgctttta tctgtctggg | 120 |
| caagagctgc tcaagccaca ccttgtgaca ctgagatcag ctatgaaaat acccagccgg | 180 |
| cctgcagccc tcccggcaga tgctgaaaag gaaacccgac tgggagatgc cgcccaccct | 240 |
| tatccccaga gagctgcgtt gtttcctctt gccttggcct ttggatccgg ccatagcaag | 300 |
| catccctggg cacctggctg aagctggaaa ctcgggataa gaatggaagc cctggaaggg | 360 |
| aagaagaacc gaggagtgag cttgccctga ggacagcaca ttgcactctc acctcctttg | 420 |
| cagttaagtg tgaaatagtg ccaatagagt gtaaaagaaa agaaagaaga tgattcacct | 480 |
| cccaaagatt ccccactgct gtgtcccttc tatcaacttg atacaaaaaa acacaatggc | 540 |
| cccgggaacc acgtgttgaa gatgagagag ctaaaagatg gaaagagact ggagccctga | 600 |
| gtcaccacct ggaggaaaac tacccaccca tcaggaattt ctactacaca tttgggagtt | 660 |
| tttgggggtta cagcagctaa tttaacgaaa cacccagag acaagagcta ttactgcaca | 720 |
| aattggttaa gttacctttt tgtatgtttg ggtcctctct attcgatgag actgcgcgtt | 780 |
| cctttgaagc aaatctgttt aaaattctta tatccccaga gggcctagca gagagtatgc | 840 |
| acagagtgag ccttcagtaa atgctgagta ataagctcc taatgatgatga aactgtgtct | 900 |
| tcgaagtttg ttctgaccag tacttagtat aggattttgt gctgttggtc acttttcata | 960 |
| aaggttcttg ctattaagga acttgacatc caatgtactc atagaaagta gaaattcagg | 1020 |
| ggaaacaaat agaagagata tgtccaaaaa tccatttaaa atttcattga cagatattta | 1080 |
| tctcttttaat cctggaagtt gtttcatgta agggaaggtt cagtagaatg aaaacaggac | 1140 |

```
tgtaagctgg gaggagattt ggggtctctt ggccaactct gccacaaatt gtgttacctt    1200
caacttccct gcctgtaaaa tgaagtcagt ggtccctaaa atgaaattgg actaatggca    1260
aattagctag catttgatta tacatcgata gtttccccat gtgattttaa cgcacaaatc    1320
agattttgga accattaggt aggtgatctt atcttatgag tttatctttt tcaacatgga    1380
aaaataaatt tgttttgctg accgaaggct gtgtaactta gaactggaaa gagacatgta    1440
attgaataac ccatctctat ggggcaaaaa aatgaaacac ctttagtttg ttcaaagatg    1500
aaatggaaaa ataaacatgt tttaagatg                                     1529
```

<210> SEQ ID NO 22
<211> LENGTH: 6451
<212> TYPE: DNA
<213> ORGANISM: Homo sapiens

<400> SEQUENCE: 22

```
gcctctctcc atcagacacc ccaaggttcc atccgaagca ggcggagcac cgaacgcacc      60
ccggggtggt cagggacccc catccgtgct gcccccctagg agcccgcgcc tctcctctgc    120
gccccgcctc tcgggccgca acgtcgcgcg gttccttaaa cagcgcgctg gcagggtgtg    180
ggaagcagga ccgcgtcctc ccgccccctc ccatccgagt ttcaggtgaa ttggtcaccg    240
agggaggagg ccgacacacc acacctacac tcccgcgtcc acctctccct ccctgcttcc    300
tctggcggag gcggcaggaa ccgagagcca ggtccagagc gccgaggagc cggtctagga    360
cgcagcagat tggtttatct tggaagctaa agggcattgc tcatcctgaa gatcagctga    420
ccattgacaa tcagccatgt catccaggcc tcttgaaagt ccacctcctt acaggcctga    480
tgaattcaaa ccgaatcatt atgcaccaag caatgacata tatggtggag agatgcatgt    540
tcgaccaatg ctctctcagc cagcctactc ttttttaccca aagatgaaa ttcttcactt    600 ctacaaatgg acctctcctc caggagtgat tcggatcctg tctatgctca ttattgtgat    660
gtgcattgcc atctttgcct gtgtggcctc cacgcttgcc tgggacagag ctatggaac    720 ttccctttta ggaggtagtg taggctaccc ttatggagga agtggctttg gtagctacgg    780
aagtggctat ggctatggct atggttatgg ctatggctac ggaggctata cagacccaag    840
agcagcaaag ggcttcatgt tggccatggc tgccttttgt ttcattgccg cgttggtgat    900 cttttgttacc agtgttataa gatctgaaat gtccagaaca agaagatact acttaagtgt    960
gataatagtg agtgctatcc tgggcatcat ggtgtttatt gccacaattg tctatataat    1020
gggagtgaac ccaactgctc agtcttctgg atctctatat ggttcacaaa tatatgccct    1080
ctgcaaccaa ttttatacac ctgcagctac tggactctac gtggatcagt atttgtatca    1140
ctactgtgtt gtggatcccc aggaggccat tgccattgta ctggggttca tgattattgt    1200
ggcttttgct ttaataattt tctttgctgt gaaaactcga agaaagatgg acaggtatga    1260
caagtccaat atttttgtggg acaaggaaca catttatgat gagcagcccc ccaatgtcga    1320
ggagtgggtt aaaaatgtgt ctgcaggcac acaggacgtg ccttcacccc catctgacta    1380
tgtggaaaga gttgacagtc ccatggcata ctcttccaat ggcaaagtga atgacaagcg    1440
gttttatcca gagtcttcct ataaatccac gccggttcct gaagtggttc aggagcttcc    1500
attaacttcg cctgtggatg acttcaggca gcctcgttac agcagcggtg gtaactttga    1560
gacaccttca aaaagagcac ctgcaaaggg aagagcagga aggtcaaaga gaacagagca    1620
agatcactat gagacagact acacaactgg cggcgagtcc tgtgatgagc tggaggagga    1680
```

```
ctggatcagg gaatatccac ctatcacttc agatcaacaa agacaactgt acaagaggaa    1740
ttttgacact ggcctacagg aatacaagag cttacaatca gaacttgatg agatcaataa    1800
agaactctcc cgtttggata agaattggat tgactataga gaagaaagtg aagagtacat    1860
ggctgctgct gatgaataca atagactgaa gcaagtgaag ggatctgcag attacaaaag    1920
taagaagaat cattgcaagc agttaaagag caaattgtca cacatcaaga gatggttgg    1980 agactatgat agacagaaaa catagaaggc tgatgccaag ttgtttgaga aattaagtat    2040
ctgacatctc tgcaatcttc tcagaaggca aatgactttg gaccataacc ccggaagcca    2100
aacctctgtg agcatcacaa agttttggtt gctttaacat catcagtatt gaagcatttt    2160
ataaatcgct tttgataatc aactgggctg aacactccaa ttaaggattt tatgctttaa    2220
acattggttc ttgtattaag aatgaaatac tgtttgaggt ttttaagcct taaaggaagg    2280
ttctggtgtg aactaaactt tcacaccccca gacgatgtct tcatacctac atgtatttgt    2340
ttgcataggt gatctcattt aatcctctca accaccttc agataactgt tatttataat    2400 cactttttc cacataagga aactgggttc ctgcaatgaa gtctctgaag tgaaactgct    2460
tgtttcctag cacacacttt tggttaagtc tgttttatga cttcattaat aataaattcc    2520
ctggcctttc atatttagc tactatatat gtgatgatct accagcctcc ctattttttt    2580
tctgttatat aaatggttaa aagaggtttt tcttaaataa taaagatcat gtaaaagtaa    2640
caaatgtgtg aaatttaaag attgtaaata tatattact ttttaagat caaagtttaa    2700 accccgtggt tagaattttg tgtgttttta aatacttttt atcttttgc atgcctttt    2760 taaaaaacca actagaactt ttcattatat cagaatatct gattacattt ataattcaat    2820
tgtgacttga actgtatctt acaggaatgt tcaatttcta tacatatttt ataaggtatt    2880
aaacctggtg ttttctttcc ataataacct gtttgatgtt attagtgctg ttaacataca    2940
gcaatggaaa accacactca ggagttgtat ctgttgttgt ttatactcct ttggatgctg    3000
tgctggttag tcgtttccca ttcctttggc tgtaagaatg ctgatatgtc tgggaataga    3060
atgctatacc acgaaatacc aaataatttc aaatggtgcc cttaaattgt atcacttttt    3120
taaaaattca gattcttatt agtaaaatta gttgatagca ctgtgctgac caagttgatt    3180
gtgatcatcc cagcttagac ttttctaaaa acttttttt agaataatct ataaactgaa    3240
ctttagtatg catttcagat atttaggtat ataattttt ttttttttg agacagagtc    3300 tcactctcac ccaggctgga atgcagtggt gctatcttgg ctcactgcaa cctccacctc    3360
ccgggttcaa gcaattctcc tgcctcagcc tctcgagtag ttgagactac aggtgcccat    3420
caccatgcgt ggctaatttt tgtatttta atagagacgg ggttttacca tagtggccag    3480
gttggtcttg aactcctgac cttgtggtct gcctgcctcg gcctcccaaa gtgctgggat    3540
tacaggcgtg agccaccatg cctggcctaa gtgtgtgtgt gtgtgtgtgt gtgtatttt    3600 tttttttt ttttgagatg gagttttgct cttgttgaac aggctggagt gcaatgtcgc    3660
gatctcagct caccacaacc tccgcctccc aggttcaaac aattctcctg cctcggcctc    3720
ccgagtagct gggattacag gcatgcgcca ccacacctgg ctaattttt ttttgtattt    3780 ttagtagaga tgggtttct ccatgttggt caggctggtc tcgaactcct gacctcaggt    3840
gatccatcca cctcggcctc ccaaagtgct gggattagag gcgtgagcca ctgtgcccgg    3900
cctataattt tgatagatg attttgaatt attttccaga gataaatttt taaatgtttc    3960
cattatatca ctgattatt tctgcaaatt gaataaattc ttaattttct gcatgcacat    4020
aatacaaaag gtattttcat agttttggat ttataccaaa tgaaaggat tctcttgatg    4080
```

```
agcacctttta actgattttt ctgttaaagt tttaacaatt tgttcttgga agtcagttcg    4140
tgaaggcaag tttgtcagta ttttcacaaa actattcagc tgaatccaga aagtgaaaca    4200
gcaagaattt gcattgtaaa attgtgttat aaaattggac tttgaaattt caaaaataag    4260
aaaaattttc atgtgtattt atactaaata ccgttttagg aaactaggat cagggtgttt    4320
ctgttggcgt tggcattaac tagctggatg taaatttgaa aagccactca agcagcttcc    4380
tagtctagaa agtcagaggt ttagattaga tttccgacat cccttccatt tctgacctgt    4440
agttcttgtc tggaattctg ctttgttata aactattgtt ctaaggagtt tgttgtgata    4500
gcacatagtt cattttgtaa agattccctg cgtataaagt gatgccctac atatgtgatt    4560
ttgtattaaa agtatatagg atcattattt tattttgaaa aatttaaata cagaaaagta    4620
taaaatataa gtaccatccg cccagaaata acatgtgtta atgttttgtc atatgtgctt    4680
tatatttttt gaaataaagt gaagtcaact agtatttata gtaaataagt tacatacaca    4740
taagtacata tatgatattt aatcctcaca acgatctttt gacatgtgac catttcttat    4800
tcttctttta tagacaagga actaatgata tgatagatta actggctgtt gtcacactag    4860
caagtggcaa acaagggat taggatctta gtctcttcaa ctgttagatt ctatacttcc    4920
atcctgtgtt gactttgtta atggattgga taatgtgaga tcactctgat gtaaataaag    4980
tatcctatat taatttcgag tgcattttaa gtacttgtaa cataaatgct tcctgtgaaa    5040
tatctgtaaa gacctgaatg ggtacatgtg tgtaaagaag aatcagggca gaaaagtgct    5100
tttatcatgg ctccggggac cttagcttca gttggtgttg tgagaattcc tcacacaagg    5160
acattctcct tgcttcagca tcaggatgga agtgtttctc atctggactt tttcaaagac    5220
tcagctggag gaatcagaat tcataatttc ctggcagctc atgattctgc tacactacac    5280
catgccatct cttgtgtgaa aggacagatt tgatggagga ctatgtcatc cctcatgcgt    5340
ttcttattgt ctacatttat tctaatggga agaagtgagc aaaaacacct caataatttg    5400
ggtagttttt agaaaacctt gttagtaaat tagaatagtg ccactttggc attatgagaa    5460
agaagcatgg atacataact agggttttgt gtatgactac aacgaaatgc agaatggtgt    5520
ctccaaaagg tttccaattg ctgccacaag aactgcttgg tattgcctac atgtgttgtc    5580 ctattttgc tttgcccttc tgcagttact tgctgtggga ccttggagaa attaacttag    5640
cctctctgta cttcagtttt ttgtatttgt aaaatatatt tgtaataatc tcatagttaa    5700
gaaggtagtt aatgtgtgac tcagtccttg tctaaaagta aatatgccta gctaccccca    5760
tcttccaaag ccagaaggtg aaactttaac aagttttcta aaagcaaatt gtgttttta    5820 aaagtgcatg tgtcatccaa tcccatatga ttgatctgtg ctgggtgcag ccttagaatg    5880
taaattcttt tgaattctag gcagagaatg caggattggc attctaaata tttgtacatg    5940
ataaacaaat gcttctttag gttagagcaa atagtttact tatcaagatc acaattgtta    6000
gatactgttg tcaattacag aggttttaga tgaggctttc tggaatgatt tagtttccct    6060
gtaagggagc ctgtctattg aatagacag gttcacttct cccagtcttt caagttgcat    6120 gcttttata tctgattcca ctggctgagc tgattgtgaa tgtcctaacc ctgttgattg    6180
tgtctggcca ctcatgggca aagaacagat tatccattct ttatagttgt cttttagttt    6240
tacaagttga aaaacatctc gagtaggtta gataaattat tctaccactt tgtaaatgat    6300
tagaatatgt cagtcataat catgccaaga gattatggat ttatgcatat tttgttttgc    6360
tgtagtacca ttcctagttg aatcttaaca tccatgtcta aaatctatac agaacaaata    6420
```
ttacagttgg gaaaactgaa aaaaaaaaaa a                                     6451

<210> SEQ ID NO 23
<211> LENGTH: 3961
<212> TYPE: DNA
<213> ORGANISM: Homo sapiens

<400> SEQUENCE: 23

```
gaggtcttcc tgttttgga gggggcaggc accccagggc cgattgtcgc gaatcacctt       60
cacctctggg ggctcagaat ccctgagcca aaggccagg gcagggctgg gggatacccc      120
tgctgctcag acaggaaaat gggctcgag cttgcccaat acttcccaga aggacgaggc      180
tgctgaactt ctcattcggg gctccgggac ctggactgta ccccttcctg gcgtcacctc      240
ctcctgtcgc ctggccctcg ccatgcagac cccgcgagcg tccctcccc gcccggccct      300
gctgcttctg ctgctgctac tggggggcgc ccacggcctc tttcctgagg agccgccgcc      360
gcttagcgtg gcccccaggg actacctgaa ccactatccc gtgtttgtgg gcagcgggcc      420
cggacgcctg accccgcag aaggtgctga cgacctcaac atccagcgag tcctgcgggt      480
caacaggacg ctgttcattg gggacaggga caacctctac cgcgtagagc tggagccccc      540
cacgtccacg gagctgcggt accagaggaa gctgacctgg agatctaacc ccagcgacat      600
aaacgtgtgt cggatgaagg gcaaacagga gggcgagtgt cgaaacttcg taaaggtgct      660
gctccttcgg gacgagtcca cgctctttgt gtgcggttcc aacgccttca acccggtgtg      720
cgccaactac agcatagaca ccctgcagcc cgtcggagac aacatcagcg gtatggcccg      780
ctgcccgtac gaccccaagc acgccaatgt tgccctcttc tctgacggga tgctcttcac      840
agctactgtt accgacttcc tagccattga tgctgtcatc taccgcagcc tcggggacag      900
gcccaccctg cgcaccgtga acatgactc caagtggttc aaagagcctt actttgtcca      960
tgcggtggag tggggcagcc atgtctactt cttcttccgg gagattgcga tggagtttaa     1020
ctacctggag aaggtggtgg tgtcccgcgt ggcccgagtg tgcaagaacg acgtgggagg     1080
ctccccccgc gtgctggaga agcagtggac gtccttcctg aaggcgcggc tcaactgctc     1140
tgtacccgga gactcccatt tctacttcaa cgtgctgcag gctgtcacgg gcgtggtcag     1200
cctcggggc cggcccgtgg tcctggccgt ttttccacg cccagcaaca gcatccctgg     1260
ctcggctgtc tgcgcctttg acctgacaca gtggcagct gtgtttgaag gccgcttccg     1320
agagcagaag tcccccgagt ccatctggac gccggtgccg gaggatcagg tgcctcgacc     1380
ccggcccggg tgctgcgcag cccccgggat gcagtacaat gcctccagcg ccttgccgga     1440
tgacatcctc aactttgtca agaccacccc tctgatggac gaggcggtgc cctcgctggg     1500
ccatgcgccc tggatcctgc ggaccctgat gaggcaccag ctgactcgag tggctgtgga     1560
cgtgggagcc ggcccctggg gcaaccagac cgttgtcttc ctgggttctg aggcggggac     1620
ggtcctcaag ttcctcgtcc ggcccaatgc cagcacctca gggacgtctg gctcagtgt     1680
cttcctggag gagttgaga cctaccgcc ggacaggtgt ggacgcccg cggtggcga     1740
gacagggcag cggctgctga gcttggagct ggacgcagct tcgggggcc tgctggctgc     1800
cttccccgc tgcgtggtcc gagtgcctgt ggctcgctgc cagcagtact cggggtgtat     1860
gaagaactgt atcggcagtc aggaccccta ctgcgggtgg gccccgacg ctcctgcat     1920
cttcctcagc ccgggcacca gagccgcctt tgagcaggac gtgtccgggg ccagcacctc     1980
aggcttaggg gactgcacag gactcctgcg ggccagcctc tccgaggacc gcgcggggct     2040
ggtgtcggtg aacctgctgg taacgtcgtc ggtggcggcc ttcgtggtgg agccgtggt     2100
```

-continued

```
gtccggcttc agcgtgggct ggttcgtggg cctccgtgag cggcgggagc tggcccggcg    2160
caaggacaag gaggccatcc tggcgcacag ggcgggcgag gcggtgctga gcgtcagccg    2220
cctgggcgag cgcagggcgc agggtcccgg gggccggggc ggaggcggtg gcggtggcgc    2280
cggggttccc ccggaggccc tgctggcgcc cctgatgcag aacggctggg ccaaggccac    2340
gctgctgcag ggcgggcccc acgacctgga ctcggggctg ctgcccacgc ccgagcagac    2400
gccgctgccg cagaagcgcc tgcccactcc gcacccgcac ccccacgccc tgggcccccg    2460
cgcctgggac cacggccacc cctgctcccc ggcctccgct tcatcctccc tcctgctgct    2520
ggcgcccgcc cgggcccccg agcagccccc cgcgcctggg gagccgaccc ccgacggccg    2580
cctctatgct gcccggcccg gccgcgcctc ccacggcgac ttcccgctca ccccccacgc    2640
cagcccggac cgccggcggg tggtgtccgc gccacgggc cccttggacc cagcctcagc    2700
cgccgatggc ctcccgcggc cctggagccc gccccgacg ggcagcctga ggaggccact    2760
gggcccccac gcccctccgg ccgccaccct gcgccgcacc cacacgttca acagcggcga    2820
ggcccggcct ggggaccgcc accgcggctg ccacgcccgg ccgggcacag acttggccca    2880
cctcctcccc tatgggggg cggacaggac tgcgcccccc gtgccctagg ccgggggccc    2940
cccgatgcct tggcagtgcc agccacggga accaggagcg agagacggtg ccagaacgcc    3000
ggggcccggg gcaactccga gtgggtgctc aagtcccccc cgcgacccac ccgcggagtg    3060
gggggccccc tccgccacaa ggaagcacaa ccagctcgcc ctcccctac ccggggccgc    3120 aggacgctga gacggtttgg gggtgggtgg gcgggaggac tttgctatgg atttgaggtt    3180
gaccttatgc gcgtaggttt tggttttttt tgcagttttg gtttcttttg cggttttcta    3240
accaattgca caactccgtt ctcggggtgg cggcaggcag gggaggcttg gacgccggtg    3300
gggaatgggg ggccacagct gcagacctaa gccctccccc accctggaa aggtccctcc    3360 ccaacccagg cccctggcgt gtgtgggtgt gcgtgcgtgt gcgtgccgtg ttcgtgtgca    3420
aggggccggg gaggtgggcg tgtgtgtgcg tgccagcgaa ggctgctgtg ggcgtgtgtg    3480
tcaagtgggc cacgcgtgca gggtgtgtgt ccacgagcga cgatcgtggt ggccccagcg    3540
gcctgggcgt tggctgagcc gacgctgggg cttccagaag gcccggggt ctccgaggtg    3600 ccggttagga gtttgaaccc cccccactct gcagagggaa gcgggacaa tgccggggtt    3660 tcaggcagga gacacgagga gggcctgccc ggaagtcaca tcggcagcag ctgtctaaag    3720
ggcttggggg cctgggggc ggcgaaggtg ggtgggccc ctctgtaaat acggccccag    3780
ggtggtgaga gagtcccatg ccacccgtcc ccttgtgacc tcccccctct gacctccagc    3840
tgaccatgca tgccacgtgg ctggctgggt cctctgccct ctctggagtt tgcctccccc    3900 agcccctcc ccatcaataa aactctgttt acaaccaccg gcaaaaaaaa aaaaaaaaa    3960 a                                                                    3961
```

<210> SEQ ID NO 24
<211> LENGTH: 1866
<212> TYPE: DNA
<213> ORGANISM: Homo sapiens

<400> SEQUENCE: 24

```
gcattgctac ctgcccttct caaagcccac atgttgtatt ttatgcaaat ctacagatta     60
tctatcatta tctaaatgca ggcatctgaa aaccagcagt aatcctgcct ctgaagttta    120
tcaggaaagg agcttaaaag agaaccaaat tcagcctgtg ttggaactct cagtcccaga    180
```

-continued

| | |
|---|---|
| ggggtgtggt tgtagctct ccggcctgct gttggactta ggctgtgacc cacagaagga | 240 |
| cgccagaaag tactcaagac attcacggtg ccccggtcag cactcgccat gacgaagact | 300 |
| tctacatgca tataccactt ccttgttctg agctggtata ctttcctcaa ttattacatc | 360 |
| tcacaggaag gaaagacga ggtgaaaccc aaaatcttgg caaatggtgc aaggtggaaa | 420 |
| tatatgacgc tgcttaatct gctcaagaac aggactgctg ggtttgacat ctaccagcca | 480 |
| ggaagcttta ggcagctctt gcagaccatt ttctacgggg tcacctgcct ggatgatgtg | 540 |
| ctgaaaagaa ccaaaggggg aaaagacatt aagttcctaa ctgccttcag agacctgctt | 600 |
| ttcaccactc tggcttttcc tgtatccacg tttgtatttt tggcattctg gatcctcttt | 660 |
| ctctacaatc gagatctcat ttaccccaag gtcctagata ctgtcatccc cgtgtggctg | 720 |
| aatcatgcaa tgcacacttt catattcccc atcacattgg ctgaagtcgt cctcaggcct | 780 |
| cactcctatc catcaaagaa gacaggactc accttgctgg ctgctgccag cattgcttac | 840 |
| atcagccgca tcctatggct ctactttgag acgggtacct gggtgtatcc tgtgtttgcc | 900 |
| aaactcagcc tcttgggtct agcagctttc ttctctctca gctacgtctt catcgccagc | 960 |
| atctacctac ttggagagaa gctcaaccac tggaaatggg gtgacatgag gcagccacgg | 1020 |
| aagaagagga gtaattgca caccattttc caagaaccaa gaaagaagaa acacaagag | 1080 |
| attttctca tcttttttt ttttttctgg tggagggagg tggtggagga acatagcaaa | 1140 |
| gtaggaggga cagagagtga tacttaaatt taataagagg ttcgtgaagg tagcttaact | 1200 |
| tgagaactct tggttttttg aaaggttgac tgcacatgcc aaaaacaact cctgctatct | 1260 |
| cagaattaat tatctttgac cttcgtggag atggtctct ggttaaaatc tggccaaaga | 1320 |
| aactcacata aacttggtgt tagagaacat ctagagagag agagaggaac ttagagtcat | 1380 |
| ttaaactctt cagtttacag agaaggatgc tgaggaccta gatgagaagt tacctgcaaa | 1440 |
| aggcaaaagg gttacttagt gtcagaacca aggcaatgac ttctctctcc cagatctcct | 1500 |
| agctactggt cctgggccat tttttttttt ttaaataatc ccaactttct ttaaaagaca | 1560 |
| agcatttcag taagctagtt attttcatgg gttgctcatc cattttttc agtgatctaa | 1620 |
| aaatgtaggg agatggctac tactgaagtt gtctgtctac ttgggataat agcaaattaa | 1680 |
| ttgaagacaa tgggaaagta agttataaaa aatactggga aatctgtttc tcttctgagc | 1740 |
| aagcattcag gcaggtata aacatcaaac atagtgacat tgtcaaaacc tcttccattt | 1800 |
| gaacattgat taattcatca aataaatggt atagtaataa attttgcttg cagaagaaaa | 1860 |
| aaaaaa | 1866 |

<210> SEQ ID NO 25
<211> LENGTH: 7169
<212> TYPE: DNA
<213> ORGANISM: Homo sapiens

<400> SEQUENCE: 25

| | |
|---|---|
| cacggtgcct gcacgggacg ccgctcgatc cccgagcccc ctcgccgtcc ccgacagccc | 60 |
| ccccggcgcc atgcaatccc ggcttctact cctcggggca cccggaggcc acggcggccc | 120 |
| ggcctcgcgg cgcatgcggc tgctcctgcg gcaggtggtg cagcgcaggc cgggtggcga | 180 |
| caggcagcgg ccggaggtca gactgttgca cgccggctcg ggggccgaca caggtgatac | 240 |
| agttaatatt ggagatgtat cctacaagtt gaaaattcct aagaatccag aacttgtgcc | 300 |
| acagaactac atttcagact ctctggctca atctgtagtt cagcatctaa gatggataat | 360 |
| gcagaaggat cttttggggc aagatgtttt tctaatagga cctcctgggc tcttcgacg | 420 |

```
ctctattgct atgcagtact tggagctgac caaacgggag gtcgaataca ttgccctgtc    480
aagggacacc actgaaactg atctcaaaca gcgacgagag atccgtgcag gcacagcctt    540
ttacattgat cagtgtgcag ttcgtgcagc cacagaaggc agaactctca ttttggaagg    600
tttggaaaag gcagagagga atgttttgcc tgttttgaac aacttgctgg aaaacagaga    660
gatgcagctt gaagatggac gcttcctgat gtctgctgag cgttacgaca acttctccg     720 agatcatacc aaaaaagagt tggattcttg gaaaattgtc cgagttagtg aaaatttccg    780
agtgattgcc ttgggcttgc cagtgccaag gtattctggg aatccattag acccccctct    840
tcgttctcga tttcaagcca gggatattta ttatttaccc ttcaaggacc aacttaagtt    900
gttatattca attggagcca atgtttctgc tgagaaagtt tctcagctct tgtcctttgc    960
cacaactctg tgttcccaag aatcttctac tcttggactt ccagactttc ctttagatag   1020
tttagcagct gcggttcaaa tcttggattc ctttcctatg atgccaatca acatgcaat    1080 ccagtggctt tatccatata gtattttact aggtcatgaa gggaagatgg ctgtggaagg   1140
tgttttaaag cgctttgaac ttcaagattc aggaagctct ctacttccta aagagattgt   1200
aaaagtagag aagatgatgg aaaaccatgt gtcccaagct tctgtgacca tccggattgc   1260
agataaagag gtgaccatta aggtgccagc cgggaccagg ctattaagtc aaccttgtgc   1320
gtcagaccgt ttcatacaga cttttgagcca taagcagcta caggctgaaa tgatgcagtc   1380
tcacatggtt aaagatatat gtttaattgg aggaaagggt tgtggaaaaa cagtgatcgc   1440
taagaacttt gccgatacct taggatacaa catagaacct attatgctct atcaggatat   1500
gacagcgcgt gatctgctac agcagagata caccttcca aatggagaca ctgcctggcg    1560
gtcctcaccc cttgtgaatg ctgctctgga aggcaagctg gtcctgctgg atggcattca   1620
ccgggtgaat gcgggcacgc ttgctgtatt gcaaaggtta atccatgatc gagagctaag   1680
cctctatgat ggttctaggc tgctgagaga agacaggtat atgcgtttaa aggaggagct   1740
gcaactgtct gatgaacagc tacagaagag atccattttt cctatccatc cctccttcag   1800
aatcattgcc ttggcagaac cccctgttat tggaagcaca gcacaccagt ggctgggacc   1860
agaattctta accatgttct ttttccatta catgaaacca cttgtgaaaa gtgaagaaat   1920
ccaagtgatt aaggaaaagg tcccaaatgt acctcaggaa gctctggata agttattatc   1980
atttacacac aaaactcagag aaacacagga tccaacggca caatcattag cggcatcact   2040
ttctaccaga caactgttgc gaatttctcg tcggctgtca cagtatccta atgaaaatct   2100
tcacagtgct gttactaaag cctgcctttc caggtttta cccagtcttg ctaggtcagc    2160
attagaaaaa aatctggcag atgctacaat agaaataaat actgatgaca atttggagcc   2220
agaactgaag gattacaaat gtgaagtaac atctggaact ctgaggattg gtgctgttag   2280
tgcaccgatc tataatgcac atgagaaaat gaaagtgcct gatgttcttt tctatgacaa   2340
cattcagcat gtgatagtga tggaagatat gctgaaagac tttctccttg gagaacactt   2400
attattggtt ggcaaccagg gtgtaggaaa aaacaagatt gttgacagat ccttcacct    2460 gctcaacaga ccccgagaat atattcagct acacagggat accacagtac aaactcttac   2520
gcttcagcct tcggttaaag acggacttat tgtatatgaa gactcacctt tggttaaagc   2580
agtaaagttg ggtcatattc tggtagtaga tgaggctgac aaagctccaa caaatgtcac   2640 gtgtattttta aaaactctag tagaaaatgg agaaatgatt ctagcagatg gaagacgcat   2700
tgttgcaaat tctgctaatg tgaatggaag agaaaatgtt gtagtgattc atcctgattt   2760
```

```
taggatgatt gttctggcaa atagacctgg atttcctttc ctaggcaatg atttcttcgg   2820
taccttaggt gatattttta gctgccatgc agttgataac cccaaacccc actcggagct   2880
cgagatgctc agacagtatg gaccaaatgt gcctgagccc atccttcaga agcttgtggc   2940
tgcctttgga gagctgagga gtttggctga ccaagggatt attaactatc cttattctac   3000
cagagaagtt gtcaacatag tcaaacattt acagaaattt ccgactgaag gtctctccag   3060
tgtagttcga atgtgtttg actttgattc ctacaacaat gacatgaggg agatattgat   3120
taacacttta cacaaatacg ggatacctat cggagcaaag cctaccagtg tgcagctggc   3180
aaaggagttg actctgccag aacaaacgtt catgggctac tggacaattg gtcaggcaag   3240
aagtgggatg caaaaactct tgtgtccagt ggaaactcat catatagaca taaagggtcc   3300
agcacttata aatatacagg agtatccaat agaaagacat gaagaaagat ccctaaactt   3360
tactgaagaa tgtgcctcat ggagaatacc attggatgaa attaatataa tctgtgacat   3420
tgctacatca catgaaaatg agcaaaatac tctctatgta gttacatgca atcccgcttc   3480
cctgtacttt atgaatatga ctgggaaaag tggcttcttt gtggactttt ttgatatctt   3540
cccaagaaca gccaatggcg tttggcaccc ttttgtgaca gtggcaccgc tgggaagtcc   3600
tctcaaaggt caagtggttc tccatgagca gcagagtaat gttatcctgt tgttagatac   3660
tactggccgg gcccttcatc gtctcatcct cccttccgag aagtttacat ctaagaaacc   3720
tttctggtgg aacaaagaag aagctgaaac ttataaaatg tgtaaagaat tttcacacaa   3780
aaactggctg gtgttctaca agaaaaagg gaacagcctg actgtgctgg atgttctaga   3840
agggcgaact cacaccatct cacttcccat caacctcaag acagttttcc ttgtagcaga   3900
ggacaaatgg cttctggtgg agagcaaaac aaatcagaaa tatctttaa ctaagcctgc   3960
acacatcgaa tctgagggta gtggggtttg ccagttgtat gtgctgaaag aggagccgcc   4020
cagcacaggg tttggagtta cacaagaaac agagttcagc atacctcata aaatttccag   4080
tgatcaacta tcatctgaac atctaagttc agctgtggaa caaagattg cctctcccaa   4140
cagaattctc tcagatgaga aaaattatgc tacaatagtt gttggttttc cagatctcat   4200
gtcacccagt gaagtttatt cttggaagag accatcatct ttgcataaac gaagtggcac   4260
tgatacatca ttctatagag gaaagaagaa aagggggact ccaaaacaaa gcaattgtgt   4320
gactcttta gatacgaatc aggtagtgag gattttaccc ccaggagaag tccctctaaa   4380
agatatctac ccaaaagatg ttactcctcc acaaacatct ggttatatag aagtcactga   4440
tcttcaatca aagaaactcc gatatatccc tattcccaga tcagaatctc tctcgccgta   4500
taccacatgg ctgtcgacca tttcagacac agatgcactg ctggctgagt gggacaaaag   4560
cggtgttgtt actgttgata tgggaggtca catcaggctt tgggaaactg acttgaacg   4620
tctgcagcga tcactcatgg aatggagaaa catgattgga caagatgaca gaaatatgca   4680
gataacaatc aacagagaca gtggtgaaga tgtaagctcc cccaaacacg ggaaggagga   4740
cccagacaac atgcctcacg tgggcggcaa cacttgggct ggcggaacag ggggaagaga   4800
cacggcaggc ctgggtggca aaggaggccc ttaccggctg gatgcaggcc atacggtgta   4860
ccaggtctct caggctgaga agatgcagt tcccgaagag gtcaagagag ctgctagaga   4920
gatgggccag agagcattcc agcagaggct aaaggagatc caaatgagtg aatacgatgc   4980
tgcaacctat gaaaggtttt caggtgctgt tcggcgacag gtgcactccc tccgaatcat   5040
cctggataat ttacaggcta aaggtaaaga aagacaatgg ctaagacatc aagctactgg   5100
agaattagat gatgccaaga tcattgatgg gctgactgga gaaaaagcca tctacaaacg   5160
```

```
tcggggtgag ctggagccac aacttggcag cccacaacag aaacccaagc gtctgcgcct    5220
ggtggtagat gtgtctggta gcatgtaccg tttcaacagg atggatggcc ggcttgagcg    5280
cacaatggag gctgtgtgta tggtcatgga agccttcgag aactatgagg agaagttcca    5340
gtatgacatc gttggacact ctggagatgg ctacaacatt ggtctggttc caatgaacaa    5400
aatccccaag gacaataagc aaagactaga aattctgaag acaatgcatg cccactctca    5460
gttctgcatg agtggggacc acacgttaga agggacagaa catgccatca ggaaattgt     5520 caaagaagaa gctgatgagt actttgtcat agtcttgagt gatgcaaatc tgtcacgata    5580
tggaatacat cctgctaagt ttgctcaaat cctcacaaga gaccctcaag taaatgcttt    5640 tgccatttt attggctctt taggtgatca agcaaccagg cttcagagaa ctttaccagc     5700
tggtcggtct ttcgttgcca tggataccaa ggatatccct cagattttac aacagatctt    5760
cacctccacc atgttgtcga gtgtctaaga agtgcccttc atcccctga tgacaccagg     5820 atttgaaata agacaggaat aaagagtatt ctgaaaaaaa gaagatatgg atgaagtgaa    5880
cccatgcagt gactggatga ttccggcatt cctgggtctt cctacacttg ctccgtaatg    5940
agaattcaga gaagcagcca gaaggagact taaacatgga aagatactcc actgatgagt    6000
ttagaagtga ttagggcaag ctagttgacc tgcactttat caaaggttgg ggttaaagga    6060
aggtggtttt gagaactatg tgtttggtct atttccaaaa acctgagggg gagaaaatac    6120
tttgcttttg ccttaacaca tcatctggtc acgttagaaa agtgacccca tcaaactgag    6180
cctttgatgt cacattctga cacaagatgc aagtctgtgc aaaacccacc aaaatgctcc    6240
tatccaacaa ttatttttat tttctccctg ctctgtattg accagaaaac aatgatttta    6300
taatatttaa cccaccaaaa agtccctcca acagcaatat cttatgaaag gctggctgtt    6360
ctcaataatt tcattttctt ggccaaagcc aaaaggaatc aaaaaatcct tggagtgctt    6420
gcctttccac gtgactttta aaaggctctt aaagagcaaa tgtcctcttc tccttgctgc    6480
tagagtggga ggagaaagat gtcttgcctt aaaagtttac tgtttcttct gttcttctag    6540
catctctcaa aaaattcaca gtactccatt ttggggtcca aactgtaatg ctcaaaataa    6600
taaatgctta cacgaaaatt atttattgag aatattcata taaaaattac ctaaagcaaa    6660
gtaaaaaaag taaaatcaag gtggtatatt tgaagtgaat ggtgattgga aattttagc    6720 tgtaacaaaa agaaagaaaa caactttttt taaagcctca ttctcttttc tttcaaaatg    6780
taccttattc ccacacactc ttgggctgac ctttatttta tcaataagct caatattact    6840
ttgtttaaaa taagatgctt cagcaaaagt cattctctct ttaaccatat aatttaaaaa    6900
ctcctcttca cgattgatag caaaatcaga aacgttaggg caccagtgag ttgaaaaaac    6960
tggtcttaag ttgaaaaaac tattattaat aatattatcc tatccatcca tatctattga    7020
aattgtacag gtccataatt tcattttaat taattatagg aaagaagaaa agataatacc    7080
catttgttct atcaccccctc tccctatcat taactatcaa ataaataaat aaaagcaatc    7140
tgatttccaa cgtggtacta aaaaaaaaa                                      7169

<210> SEQ ID NO 26
<211> LENGTH: 1121
<212> TYPE: DNA
<213> ORGANISM: Homo sapiens

<400> SEQUENCE: 26
acagctcttt agaccctagg aaacaacctt cctacagaga gtaaaaaata tttccaccat       60
```

| | | |
|---|---|---|
| agttggccca aaagcaatca ccaattaaga aagcgtttaa gctcaacatc tatcttaaat | 120 | |
| tctagtcact ctactgaact cctaacatca cattggacta atctattact taatagaagc | 180 | |
| aataatgtta atataagtaa tatgaaaaca ttctccattg cataagctta catcagactg | 240 | |
| gaataaccca ctgacagtta gcctaatatt aataaacgat ataataagct ctttattatt | 300 | |
| tacactgtta acccaacaca ggtatgctct aaggaaagaa tacaaaaagt aaaggaact | 360 | |
| ccgcaaattt tacccgcct gtttaccaaa aacatcacct ctagcattac cagtattaga | 420 | |
| ggcactgcct gcccagtgac atacgttcaa tggccgcagt atcctgactg tgcaaaggta | 480 | |
| gcataatcac ttgttcctta ataggaact tgtatgaatg accacacgag ggttcagctg | 540 | |
| tctcctactt ttaatcaggg aaattgacct atccgcgaag aggcggatat aaacaaataa | 600 | |
| gacgagaaga ccctatgtat ggagctttaa tttattaatg caaataaaaa cttaagccta | 660 | |
| caggccctag cctactatcc ctgcattaaa attttttggtt ggggtgacct cagagcataa | 720 | |
| ttcaacctcc gagcaaccta aactaagact gcactagcct aagcaagtta atatatattg | 780 | |
| acccgataat ttgatcaacg gagtaagtta ccctagggat aacagcgcaa tcctattcta | 840 | |
| gagtccatat caacaatagg gtttacaatc tcgatgttgg atcaggacat cctaatggtg | 900 | |
| tcaccgctat taggggttcg tttgttcaac aattaaagtc ctacgtgatg tgagttcaga | 960 | |
| ccagagtaat ccaggtcggt ttctatctat ttaacatttc ccctagtatg aaaggacaag | 1020 | |
| agaaataggg cccacttcat aaagtgccct cgctccacag atgatgctat ctcaatctaa | 1080 | |
| caaatcatca catacccctac ccaagaacag ggtttgttaa g | 1121 | |

```
<210> SEQ ID NO 27
<211> LENGTH: 1614
<212> TYPE: DNA
<213> ORGANISM: Homo sapiens

<400> SEQUENCE: 27
```

| | | |
|---|---|---|
| aatctccccc tcccaaaatc gctccattac ataaatcggg gggggtgcag gaggggggtc | 60 | |
| ccttccgatc ctccctcctg acgccccccc cagcagcccc ctcccccacc attgaaagcc | 120 | |
| atgaattttg aatttgagag ggagattggg tttataaaca gccagccgtc gctcgccgag | 180 | |
| tgtctgactt ccttccccgc tgtcttggag acatttcaaa cttcatcaat caaggagtcg | 240 | |
| acattaattc ctcctcctcc tcctttcgag caaaccttcc ccagcctcca gcccggcgcc | 300 | |
| tccacccttc agagacccag gagccaaaag cgagccgaag atgggcctgc tctgccgccg | 360 | |
| ccaccgccgc cgccactccc cgctgccccc ccggcccccg agttcccttg gatgaaagag | 420 | |
| aagaaatccg ccaagaaacc cagccaatcc gccacgtctc cttctccggc cgcctccgcc | 480 | |
| gttccggcct ccggggtcgg atcgcctgca gatggcctgg gactgccgga ggctggtggc | 540 | |
| ggcggggcgc gcaggctgcg cacggcttac accaacacgc agctgctgga actggagaag | 600 | |
| gaattccact ttaataagta cctgtgccgg ccacgccgcg tcgagatcgc ggccttgctg | 660 | |
| gacctcaccg aaaggcaggt caaagtctgg tttcagaacc ggcgcatgaa gcacaagcgg | 720 | |
| cagacgcagc accgagagcc gccggatggg gagcctgcct gcccgggagc cctggaggac | 780 | |
| atctgcgacc ctgccgagga acccgcgcc agcccgggcg gccctccgc ctcgcgggcg | 840 | |
| gcgtgggaag cctgctgtca cccgccggag gtggtgccgg gggccttaag cgcggaccc | 900 | |
| cggcctttag ccgttcgctt agagggcgca ggcgcgtcga gtcccggctg cgcgctgcgc | 960 | |
| ggggccggcg ggctggagcc cgggccattg ccagaagacg tcttctcggg gcgccaggat | 1020 | |
| tcacctttcc ttcccgacct caacttcttc gcggccgact cctgtctcca gctatccgga | 1080 | |

| | |
|---|---|
| ggcctctccc ctagcctaca gggttctctc gacagcccgg tccctttttc cgaggaagag | 1140 |
| ctggattttt tcaccagtac gctctgtgcc atcgacctgc agtttcccta acctgtttcc | 1200 |
| tcctcccggt cctttcgacc ccgcgctcc ttggccgtct actggaaaaa tcgagcctct | 1260 |
| cccaccctca gtcgcataga cttatgtgtt ttgctaaaat tcaggtatta ctgaattagc | 1320 |
| gtttaatcca ctccctttct tcttcttcta aaatattggg cactcggtta tcttttaaaa | 1380 |
| ttcacacaga aaaattccgt ttggtagact ccttccaatg aaatctcagg aataattaaa | 1440 |
| ctctagggg actttcttaa aaataactag agggacctat tttcctcttt tttatgtttt | 1500 |
| agactgtaga ttatttatta aaattcttta ataataggaa aagggaaag tatttattgt | 1560 |
| acattatttt catagattaa ataaatgtct ttataatacc aaaaaaaaaa aaaa | 1614 |

<210> SEQ ID NO 28
<211> LENGTH: 1731
<212> TYPE: DNA
<213> ORGANISM: Homo sapiens

<400> SEQUENCE: 28

| | |
|---|---|
| aactgcagcg ccggggctgg gggaggggag cctactcact ccccaactc ccggcggtg | 60 |
| actcatcaac gagcaccagc ggccagaggt gagcagtccc gggaaggggc cgagaggcgg | 120 |
| ggccgccagg tcgggcaggt gtgcgctccg ccccgccgcg cgcacagagc gctagtcctt | 180 |
| cggcgagcga gcaccttcga cgcggtccgg ggaccccctc gtcgctgtcc tcccgacgcg | 240 |
| gacccgcgtg cccaggcct cgcgctgccc ggccggctcc tcgtgtccca ctcccggcgc | 300 |
| acgccctccc gcgagtcccg gcccctccc gcgccctct tctcggcgcg cgcgcagcat | 360 |
| ggcgcccccg caggtcctcg cgttcgggct tctgcttgcc gcggcgacgg cgacttttgc | 420 |
| cgcagctcag gaagaatgtg tctgtgaaaa ctacaagctg gccgtaaact gctttgtgaa | 480 |
| taataatcgt caatgccagt gtacttcagt tggtgcacaa aatactgtca tttgctcaaa | 540 |
| gctggctgcc aaatgtttgg tgatgaaggc agaaatgaat ggctcaaaac ttgggagaag | 600 |
| agcaaaacct gaaggggccc tccagaacaa tgatgggctt tatgatcctg actgcgatga | 660 |
| gagcgggctc tttaaggcca agcagtgcaa cggcacctcc atgtgctggt gtgtgaacac | 720 |
| tgctggggtc agaagaacag acaaggacac tgaaataacc tgctctgagc gagtgagaac | 780 |
| ctactggatc atcattgaac taaaacacaa agcaagagaa aaaccttatg atagtaaaag | 840 |
| tttgcggact gcacttcaga aggagatcac aacgcgttat caactggatc caaaatttat | 900 |
| cacgagtatt ttgtatgaga ataatgttat cactattgat ctggttcaaa attcttctca | 960 |
| aaaaactcag aatgatgtgg acatagctga tgtggcttat tattttgaaa agatgttaa | 1020 |
| aggtgaatcc ttgttttcatt ctaagaaaat ggacctgaca gtaaatgggg aacaactgga | 1080 |
| tctggatcct ggtcaaactt taatttatta tgttgatgaa aaagcacctg aattctcaat | 1140 |
| gcagggtcta aaagctggtg ttattgctgt tattgtggtt gtggtgatag cagttgttgc | 1200 |
| tggaattgtt gtgctggtta tttccagaaa gaagagaatg gcaaagtatg agaaggctga | 1260 |
| gataaaggag atgggtgaga tgcataggga actcaatgca taactatata atttgaagat | 1320 |
| tatagaagaa gggaaatagc aaatggacac aaattacaaa tgtgtgtgcg tgggacgaag | 1380 |
| acatctttga aggtcatgag tttgttagtt taacatcata tatttgtaat agtgaaacct | 1440 |
| gtactcaaaa tataagcagc ttgaaactgg ctttaccaat cttgaaattt gaccacaagt | 1500 |
| gtcttatata tgcagatcta atgtaaaatc cagaacttgg actccatcgt taaaattatt | 1560 |

-continued

| | |
|---|---|
| tatgtgtaac attcaaatgt gtgcattaaa tatgcttcca cagtaaaatc tgaaaaactg | 1620 |
| atttgtgatt gaaagctgcc tttctattta cttgagtctt gtacatacat acttttttat | 1680 |
| gagctatgaa ataaaacatt ttaaactgaa tttcttaaaa aaaaaaaaa a | 1731 |

<210> SEQ ID NO 29
<211> LENGTH: 3661
<212> TYPE: DNA
<213> ORGANISM: Homo sapiens

<400> SEQUENCE: 29

| | |
|---|---|
| tcaggaggcg agatcgctg cttctcacct actttctgaa cttggcctcc gcagtcgcga | 60 |
| cctggcgtga aggaggagct gccgcccccg ccccagcctc ggggacgcct ctctgaagag | 120 |
| aagccatttg aagcagaatc caaaccatga attgtagaga attacccttg accctttggg | 180 |
| tgcttatatc tgtaagcact gcagaatctt gtacttcacg tccccacatt actgtggttg | 240 |
| aaggggaacc tttctatctg aaacattgct cgtgttcact tgcacatgag attgaaacaa | 300 |
| ccaccaaaag ctggtacaaa agcagtggat cacaggaaca tgtggagctg aacccaagga | 360 |
| gttcctcgag aattgctttg catgattgtg ttttggagtt ttggccagtt gagttgaatg | 420 |
| acacaggatc ttacttttc caaatgaaaa attatactca gaaatggaaa ttaaatgtca | 480 |
| tcagaagaaa taaacacagc tgtttcactg aaagacaagt aactagtaaa attgtggaag | 540 |
| ttaaaaaatt ttttcagata acctgtgaaa acagttacta tcaaacactg gtcaacagca | 600 |
| catcattgta taagaactgt aaaaagctac tactggagaa caataaaaac ccaacgataa | 660 |
| agaagaacgc cgagtttgaa gatcaggggt attactcctg cgtgcatttc cttcatcata | 720 |
| atggaaaact atttaatatc accaaaacct tcaatataac aatagtggaa gatcgcagta | 780 |
| atatagttcc ggttcttctt ggaccaaagc ttaaccatgt tgcagtggaa ttaggaaaaa | 840 |
| acgtaaggct caactgctct gctttgctga atgaagagga tgtaatttat tggatgttcg | 900 |
| gggaagaaaa tggatcggat cctaatatac atgaagagaa agaaatgaga attatgactc | 960 |
| cagaaggcaa atggcatgct tcaaaagtat tgagaattga aaatattggt gaaagcaatc | 1020 |
| taaatgtttt atataattgc actgtggcca gcacgggagg cacagacacc aaaagcttca | 1080 |
| tcttggtgag aaaagcagac atggctgata tcccaggcca cgtcttcaca agaggaatga | 1140 |
| tcatagctgt tttgatcttg gtggcagtag tgtgcctagt gactgtgtgt gtcatttata | 1200 |
| gagttgactt ggttctattt tatagacatt aacgagaag agtgaaaca ttaacagatg | 1260 |
| gaaaaacata tgatgctttt gtgtcttacc taaaagaatg ccgacctgaa aatggagagg | 1320 |
| agcacacctt tgctgtggag attttgccca gggtgttgga gaaacatttt gggtataagt | 1380 |
| tatgcatatt tgaaagggat gtagtgcctg gaggagctgt tgttgatgaa atccactcac | 1440 |
| tgatagagaa aagccgaaga ctaatcattg tcctaagtaa aagttatatg tctaatgagg | 1500 |
| tcaggtatga acttgaaagt ggactccatg aagcattggt ggaagaaaaa attaaaataa | 1560 |
| tcttaattga atttacacct gttactgact tcacattctt gcccccaatca ctaaagcttt | 1620 |
| tgaaatctca cagagttctg aagtggaagg ccgataaatc tcttctcttat aactcaaggt | 1680 |
| tctggaagaa cctttcttac ttaatgcctg caaaaacagt caagccaggt agagacgaac | 1740 |
| cggaagtctt gcctgttctt tccgagtctt aatcttcaga acagtgaac gccaaaaga | 1800 |
| actcaagata ttctggggac tgagcatatg aacctgttca taacaaaggc tgtgactcga | 1860 |
| aataattaac tttgtcaaaa tcctgctcac aatttgaaga tgaaacttgt cattaggttg | 1920 |
| gcgggaatga gactaaagat tgcgctgtgg gctgtggtca cgtgctccca gaagacctgg | 1980 |

```
aattcaaaag aaatggagct attcttttc tccctctttc ataactggat gcagctgctc    2040
atactcaatc ccatattcag caagtgtgaa gctggacgtg atgcaaaata accgatgccc    2100
tacaaaaagg gcgcatcttt aagagtttta atgccagtgc ttaattcgaa tgagggatt     2160 ttaagtgtct gaagaggcat tttctaggga ccagtgggtg actgagtaac tgaaatgctg    2220
ctttcactcc ctaacaccat ggatctggtt gtgcatagga tgtgggagga gggctggca    2280 gggccgcctt cagaggctgc agggcctcag cctcaggatg catttaatgt atcctggcca    2340
cagttgcagc caacggttct tgaaagctcg gtaaggccct gcaacgcaga gcctgcttat    2400
gtggatctat ttatgggaac ttcttaaaag daccccagaa tagctcttta tctttcacaa    2460
gagacacaaa ttctaattga gttaattatc tgggcctttc actttggatg ctctgaaaca    2520
tttgttgatt ttgtgtgaat gtttatatca aaatgtttgc caggttgtat tagccattga    2580
atagcaaaaa actgatagtt acttgcttgt tttttaaaaa ttacatatta aaaatgccct    2640
tggcataagg cagcatggtg tgcagttaa gagatgggct gtgcagccca tcctgagctc     2700
cagtcctgag tttgctactt acttctgtgg cctctggaac cttatccaac ctcttggtgc    2760
ttcagtttcc tcatctgtga aattagaatt tataataatt gcacctacct cccaggggta    2820
actaaatgaa taaatataat aaagtactta cagtggttcc tgacacagac tcagcactcc    2880
gtcagtgttg ccatgactat ttttattatc attattaatg attacttaga tcaattattt    2940
agcagtggac taatggaagc tacagagcag ggaagggaag cagatctagg gaggaaggca    3000
gttttgattt gaggaggttt gcacatgtag agaagcatac tggagaagca tatccagagg    3060
gcgaaagata tctctccatt gtgcatctgc ctcttttgac gttggaagac acatgtctta    3120
ctccccaaag ggagcccagc actgggagcc ttcttgatga tctcaaaaat aatagctatt    3180
caagaaaatc accaagtgac tgtgaaaccg tcagttcgga aggctggtta gaacatgtgg    3240
gagcaacatg aatgttctac aaaagtttaa agcagagatt gtttcaaatg ggtgtagtag    3300
atattactga aaaccaaaaa agagtgagat tgtcagtgta agaatgtgat ttaatgtttg    3360
tagtgcttac aatttttgtgt accaactgga tgactaaaaa gagtaaaata atttaattaa    3420
tagctcatat tttatgtgtg aaaacatgtt agtgaacata tataatcaaa atagatttca    3480
ttgctattgc atagtctcta atacataaa tgattttgct tttctctttt attatacttg     3540
ctttaaaata cttgaaatat attttgcatt aaatgcattt caagttaaat gtcttaaatg    3600
tatacattag atgtgtgttt taaaatgcat aaaacacgtt gaaatacatt aatgaaccat    3660
t                                                                    3661

<210> SEQ ID NO 30
<211> LENGTH: 1001
<212> TYPE: DNA
<213> ORGANISM: Homo sapiens

<400> SEQUENCE: 30
attgtacggt gagagaatga gagcaaaacc tcagagcccc cttcccagga accctgtccc      60
agcctggtcc ccacccacca ccaccactga cccgatgcta gagaaggatg cggctggagg    120
tgacttccca gccaacttgg tcctccaact aatgccactg aagacattcc cagctgctat    180
ccggggagtc atccagagtg agctcaacta ttctgtgatc ctgcagtggg tggtgacaat    240
ggaccctgag cctgtgctga gctggacctt cagtggggtg ccctgtggga tgggagagaa    300
gctgttcatc cgacggttgt cctgtgagca gctgggcacc tacatgtgca tagccacaaa    360
```

| | |
|---|---|
| cagcaagaaa cagctggtct ctgagcctgt aaccatctcg ctgccaaaac ccatcatgca | 420 |
| gcccacagaa gcagagccca tggagccaga ccccactctg tccctgtcag gaggctctgc | 480 |
| catcgggctc cttgcggctg ggatcctggg agccggggca ctgattgcag gcatgtgttt | 540 |
| catcatcatc cagagcctaa ggactgacag gcagagaata ggaatatgca gctgaaatgt | 600 |
| gggcaactct cctgtcagct gaagagatgg gtgcttttgta cctctctatc cacgtggaaa | 660 |
| aaaaaaccca tcccatagct tccaagtcta caacatctct gttcaaggga caacccaac | 720 |
| gtaaccagac tccctttgcc ctgtttctga acacctgaa gaaaacatct gatgggttga | 780 |
| ctcggtgcca tccttggtcc catcgccgtg acacgttgtg caagcaaagc atcagaggct | 840 |
| catccctgtc tgtgggagct cagtgctcag aaaacagggg ggaggtttta ccttggaaat | 900 |
| tggccagacc ccaaaatatg tcttttacac atgctgcttt ttttttctct ttttcaaaaa | 960 |
| gaaccaaaaa ataaattaaa acaccaccaa aaaaaaaaa a | 1001 |

<210> SEQ ID NO 31
<211> LENGTH: 1787
<212> TYPE: DNA
<213> ORGANISM: Homo sapiens

<400> SEQUENCE: 31

| | |
|---|---|
| gctgctcctc tgtcgagctg atcacaccca cagttgagct gcgctggcca gagatgcctg | 60 |
| cccacagcct ggtgatgagc agcccggccc tcccggcctt cctgctctgc agcacgctgc | 120 |
| tggtcatcaa gatgtacgtg gtggccatca tcacgggcca agtgaggctg cggaagaagg | 180 |
| cctttgccaa ccccgaggat gccctgagac acggaggccc ccagtattgc aggagcgacc | 240 |
| ccgacgtgga acgctgcctc agggcccacc ggaacgacat ggagaccatc tacccttcc | 300 |
| ttttcctggg cttcgtctac tcctttctgg gtcctaaccc ttttgtcgcc tggatgcact | 360 |
| tcctggtctt cctcgtgggc cgtgtggcac acaccgtggc ctacctgggg aagctgcggg | 420 |
| cacccatccg ctccgtgacc tacacccctgg cccagctccc ctgcgcctcc atggctctgc | 480 |
| agatcctctg ggaagcggcc cgccacctgt gaccagcagc tgatgcctcc ttggccacca | 540 |
| gaccatgggc caagagccgc cgtggctata cctggggact tgatgttcct tccagattgt | 600 |
| ggtgggccct gagtcctggt ttcctggcag cctgctgcgc gtgtgggtct ctgggcacag | 660 |
| tgggcctgtg tgtgtgcccg tgtgtgtgta tgtgtgtgtg tatgtttctt agccccttgg | 720 |
| attcctgcac gaagtggctg atgggaacca tttcaagaca gattgtgaag attgatagaa | 780 |
| aatccttcag ctaaagtaac agagcatcaa aaacatcact ccctctccct ccctaacagt | 840 |
| gaaaagagag aagggagact ctatttaaga ttcccaaacc taatgatcat ctgaatcccg | 900 |
| ggctaagaat gcagactttt cagactgacc ccagaaattc tggcccagcc aatctagagg | 960 |
| caagcctggc catctgtatt tttttttttc caagacagag tcttgctctg ttgcccaagc | 1020 |
| tggagtgaag tggtacaatc tggctcactg cagcctccgc ctcccgggtt caagcgattc | 1080 |
| tcccgcctca gcctcctgag tagctgggat tacaggcgcg tatcaccata cccagctaat | 1140 |
| ttttgtattt ttagtagaga cgggttcacc atgttgccca ggagggtctc gaactcctgg | 1200 |
| cctcaagtga tccaccggcc tcggcctccc aaagtgctgg gatgacaggc atgaatcact | 1260 |
| gtgctcagcc accatctgga gttttaaaag gctcccatgt gagtccctgt gatggccagg | 1320 |
| ccaggggacc cctgccagtt ctctgtggaa gcaaggctgg ggtcttgggt tcctgtatgg | 1380 |
| tggaagctgg gtgagccaag gacagggctg gctcctctgc ccccgctgac gcttcccttg | 1440 |
| ccgttggctt tggatgtctt tgctgcagtc ttctctctgg ctcaggtgtg ggtgggaggg | 1500 |

```
gcccacagga agctcagcct tctcctccca aggtttgagt ccctccaaag ggcagtgggt      1560
ggaggaccgg gagctttggg tgaccagcca ctcaaaggaa ctttctggtc ccttcagtat      1620
cttcaaggtt tggaaactgc aaatgtcccc ttgatgggga atccgtgtgt gtgtgtgtgt      1680
gtgtgtgtgt gtgtgtgtgt gtgtgtgtgt gttttctcct agacccgtga cctgagatgt      1740
gtgattttta gtcattaaat ggaagtgtct gccagctggg cccagca                   1787
```

```
<210> SEQ ID NO 32
<211> LENGTH: 978
<212> TYPE: DNA
<213> ORGANISM: Homo sapiens

<400> SEQUENCE: 32
tggctctgac cgcgctggcc tgggccggag agcccaggag gcgtgtctca gagaaaagat        60
ataagcggcc cccggacgct aaagcggtgc cagcggcgga gtctccaact gggagagctg       120
cagctgccga gaggaggaga acgctgaggt cggtcggacc aacggacgcg ctgaccgctg       180
ccaactgcag ctcgcgctgc tcctgctcg cgccgtgcca ctaaggtcat tcccgcctcc       240
gagagcccag agccgagatg gaaacggtcc aggagctgat cccctggcc aaggagatga       300 tggcccagaa gcgcaagggg aagatggtga agctgtacgt gctgggcagc gtgctggccc       360
tcttcggcgt ggtgctcggc ctgatggaga ctgtgtgcag cccccttcacg gccgccagac       420 gtctgcggga ccaggaggca gccgtggcgg agctgcaggc cgccctggag cgacaggctc       480
tccagaagca agccctgcag gagaaaggca agcagcagga cacggtcctc ggcggccggg       540
ccctgtccaa ccggcagcac gcctcctagg aactgtggga gaccagcgga gtgggaggga       600
gacgcagtag acagagacag accgagagag gaatggagag acagaggggg cgcgcgcaca       660
ggagcctgac tccgctggga gagtgcagga gcacgtgctg ttttttattt ggacttaact       720
tcagagaaac cgctgacatc tagaactgac ctaccacaag catccaccaa aggagtttgg       780
gattgagttt tgctgctgtg cagcactgca ttgtcatgac atttccaaca ctgtgtgaat       840
tatctaaatg cgtctaccat tttgcactag ggaggaagga taaatgcttt ttatgttatt       900
attattaatt attacaatga ccaccatttt gcattttgaa ataaaaaaac tttttatacc       960
ataaaaaaaa aaaaaaaa                                                    978
```

```
<210> SEQ ID NO 33
<211> LENGTH: 5395
<212> TYPE: DNA
<213> ORGANISM: Homo sapiens

<400> SEQUENCE: 33
aattcactaa tgcattctgc tcttttttgag agcacagctt tcagatgtg ctccttggag        60 ctggtgtgca gtgtcctgac tgtaagatca agtccaaacc tgttttggaa ttgaggaaac       120
ttctcttttg atctcagccc ttggtggtcc aggtcttcat gctgctgtgg gtgatattac       180
tggtcctggc tcctgtcagt ggacagtttg caaggacacc caggcccatt attttcctcc       240
agcctccatg gaccacagtc ttccaaggag agagagtgac cctcacttgc aagggatttc       300
gcttctactc accacagaaa acaaaatggt accatcggta ccttgggaaa gaaatactaa       360
gagaaacccc agacaatatc cttgaggttc aggaatctgg agagtacaga tgccaggccc       420
agggctcccc tctcagtagc cctgtgcact tggattttc ttcagcttcg ctgatcctgc       480
aagctccact ttctgtgttt gaaggagact ctgtggttct gaggtgccgg gcaaaggcgg       540
```

-continued

```
aagtaacact gaataatact atttacaaga atgataatgt cctggcattc cttaataaaa    600
gaactgactt ccatattcct catgcatgtc tcaaggacaa tggtgcatat cgctgtactg    660
gatataagga aagttgttgc cctgtttctt ccaatacagt caaaatccaa gtccaagagc    720
catttacacg tccagtgctg agagccagct ccttccagcc catcagcggg aacccagtga    780
ccctgacctg tgagacccag ctctctctag agaggtcaga tgtcccgctc cggttccgct    840
tcttcagaga tgaccagacc ctgggattag gctggagtct ctccccgaat ttccagatta    900
ctgccatgtg gagtaaagat tcagggttct actggtgtaa ggcagcaaca atgccttaca    960
gcgtcatatc tgcacagccg agatcctgga tacaggtgca gatccctgca tctcatcctg   1020
tcctcactct cagccctgaa aaggctctga attttgaggg aaccaaggtg acacttcact   1080
gtgaaaccca ggaagattct ctgcgcactt tgtacaggtt ttatcatgag ggtgtcccec   1140
tgaggcacaa gtcagtccgc tgtgaaaggg gagcatccat cagcttctca ctgactacag   1200
agaattcagg gaactactac tgcacagctg acaatggcct tggcgccaag cccagtaagg   1260
ctgtgagcct ctcagtcact gttcccgtgt ctcatcctgt cctcaacctc agctctcctg   1320
aggacctgat ttttgaggga gccaaggtga cacttcactg tgaagcccag agaggttcac   1380
tccccatcct gtaccagttt catcatgagg gtgctgccct ggagcgtagg tcggccaact   1440
ctgcaggagg agtggccatc agcttctctc tgactgcaga gcattcaggg aactactact   1500
gcacagctga caatggcttt ggcccccagc gcagtaaggc ggtgagcctc tccgtcactg   1560
tccctgtgtc tcatcctgtc ctcaccctca gctctgctga ggccctgact tttgaaggag   1620
ccactgtgac acttcactgt gaagtccaga gaggttcccc acaaatccta taccagtttt   1680
atcatgagga catgcccctg tggagcagct caacaccctc tgtgggaaga gtgtccttca   1740
gcttctctct gactgaagga cattcaggga attactactg cacagctgac aatggctttg   1800
gtccccagcg cagtgaagtg gtgagccttt ttgtcactgt tccagtgtct cgccccatcc   1860
tcaccctcag ggttcccagg gcccaggctg tggtggggga cctgctggag cttcactgtg   1920
aggccccgag aggctctccc ccaatcctgt actggtttta tcatgaggat gtcaccctgg   1980
ggagcagctc agccccctct ggaggagaag cttctttcaa cctctctctg actgcagaac   2040
attctggaaa ctactcatgt gaggccaaca atggcctagt ggcccagcac agtgacacaa   2100
tatcactcag tgtttatagtt ccagtatctc gtcccatcct caccttcagg gctcccaggg   2160
cccaggctgt ggtgggggac ctgctggagc ttcactgtga ggccctgaga ggctcctccc   2220
caatcctgta ctggttttat catgaagatg tcaccctggg taagatctca gcccctctg    2280
gaggagggc ctccttcaac ctctctctga ctacagaaca ttctggaatc tactcctgtg    2340
aggcagacaa tggtctggag gcccagcgca gtgagatggt gacactgaaa gttgcagttc   2400
cggtgtctcg cccggtcctc accctcaggg ctcccgggac ccatgctgcg gtggggacc    2460
tgctggagct tcactgtgag gccctgagag gctctcccct gatcctgtac cggtttttc    2520
atgaggatgt caccctagga aataggtcgt ccccctctgg aggagcgtcc ttaaacctct   2580
ctctgactgc agagcactct ggaaactact cctgtgaggc cgacaatggc ctcggggccc   2640
agcgcagtga gacagtgaca ctttatatca cagggctgac cgcgaacaga agtgccctt    2700
ttgccacagg agtcgccggg ggcctgctca gcatagcagg ccttgctgcg ggggcactgc   2760
tgctctactg ctggctctcg agaaaagcag ggagaaagcc tgcctctgac cccgccagga   2820
gcccttcaga ctcggactcc caagagccca cctatcacaa tgtaccagcc tgggaagagc   2880
tgcaaccagt gtacactaat gcaaatccta gaggagaaaa tgtggtttac tcagaagtac   2940
```

```
ggatcatcca agagaaaaag aaacatgcag tggcctctga ccccaggcat ctcaggaaca   3000
agggttcccc tatcatctac tctgaagtta aggtggcgtc aacccoggtt tccggatccc   3060
tgttcttggc ttcctcagct cctcacagat gagtccacac gtctctccaa ctgctgtttc   3120
agcctctgca ccccaaagtt ccccttgggg gagaagcagc attgaagtgg aagatttag    3180
gctgccccag accatatcta ctggcctttg tttcacatgt cctcattctc agtctgacca   3240
gaatgcaggg ccctgctgga ctgtcacctg tttcccagtt aaagccctga ctggcaggtt   3300
ttttaatcca gtggcaaggt gctcccactc cagggcccag cacatctcct ggattcctta   3360
gtgggcttca gctgtggttg ctgttctgag tactgctctc atcacacccc cacagagggg   3420
gtcttaccac acaaagggag agtgggcctt caggagatgc cgggctggcc taacagctca   3480
ggtgctccta aactccgaca cagagttcct gctttgggtg gatgcatttc tcaattgtca   3540
tcagcctggt ggggctactg cagtgtgctg ccaaatggga cagcacacag cctgtgcaca   3600
tgggacatgt gatgggtctc cccacggggg ctgcatttca cactcctcca cctgtctcaa   3660
actctaaggt cggcacttga caccaaggta acttctctcc tgctcatgtg tcagtgtcta   3720
cctgcccaag taagtggctt tcatacacca agtcccaagt tcttcccatc ctaacagaag   3780
taacccagca agtcaaggcc aggaggacca ggggtgcaga cagaacacat actggaacac   3840
aggaggtgct caattactat ttgactgact gactgaatga atgaatgaat gaggaagaaa   3900
actgtgggta atcaaactgg cataaaatcc agtgcactcc ctaggaaatc cgggaggtat   3960
tctggcttcc ctaagaaaca atggaagaga aggagcttgg atgaggaaac tgttcagcaa   4020
gaggaagggc ttctcacact ttcatgtgct tgtggatcac ctgaggatcc tgtgaaaata   4080
cagatactga ttcagtgggt ctgcgtagag cctgagactg ccattctaac atgttcccag   4140
gggatgctga tgctgctggc cctgggactg cactgcatgc atgtgaagcc ctataggtct   4200
cagcagaggc ccatggagag ggaatgtgtg gctctggctg cccagggccc aactcggttc   4260
acacggatcg tgctgctccc tggccagcct ttggccacag caccaccagc tgctgttgct   4320
gagagagctt cttctctgtg acatgttggc tttcatcagc cacoctggga agcggaaagt   4380
agctgccact atctttgttt ccccacctca ggcctcacac tttcccatga aaagggtgaa   4440
tgtatataac ctgagccctc tccattcaga gttgttctcc catctctgag caatgggatg   4500
ttctgttccg cttttatgat atccatcaca tcttatcttg atctttgctc ccagtggatt   4560
gtacagtgat gactttttaag ccccacggcc ctgaaataaa atccttccaa gggcattgga   4620
agctcactcc acctgaacca tggcttttca tgcttccaag tgtcagggcc ttgcccagat   4680
agacagggct ggctctgctg ccccaacctt tcaaggagga aaccagacac ctgagacagg   4740
agcctgtatg cagcccagtg cagccttgca gaggacaagg ctggaggcat tgtcatcac    4800
tacagatatg caactaaaat agacgtggag caagagaaat gcattcccac cgaggccgct   4860
tttttaggcc tagttgaaag tcaagaagga cagcagcaag cataggctca ggattaaaga   4920
aaaaaatctg ctcacagtct gttctggagg tcacatcacc aacaaagctc acgccctatg   4980
cagttctgag aaggtggagg caccaggctc aaaagaggaa atttagaatt tctcattggg   5040
agagtaaggt accccccatcc cagaatgata actgcacagt ggcagaacaa actccaccct  5100
aatgtgggtg gacccccgtcc agtctgttga aggcctgaat gtaacaaaag ggcttattct   5160
tcctcaagta aggggggaact cctgctttgg gctgggacat aagttttttct gctttcagac  5220
gcaaactgaa aaatggctct tcttgggtct tgagcttgct ggcatatgga ctgaaagaaa   5280
```

```
ctatgctatt ggatctcctg gatctccagc ttgctgactg cagatcttga gatatgtcag    5340
cctctacagt cacaagagct aattcattct aataaaccaa tctttctgta aaaaa         5395
```

<210> SEQ ID NO 34
<211> LENGTH: 984
<212> TYPE: DNA
<213> ORGANISM: Homo sapiens

<400> SEQUENCE: 34

```
cccgaggtat gctggtgctg gtggcccagg caggaggtga cactctcaaa gtgactggtc     60
actacgtaaa atgtgtcttt cttttgtttg tttcccacct gctttccgag ccccttctc    120 ggacagttga ccacggcatg tttgagaatt tgaacacagc cctcactcca aagctccagg    180
ccagccgctc cttcccccac ttgtccaagc ccgtggcccc cggctctgcc cctctgggct    240
ctggtgagcc tggggggcca ggactctggg tgggcagcag ccagcacctc aagaacctgg    300
gcaaagccat gggggccaaa gtgaatgact tcctgaggag aaaggagccc tccagcctgg    360
gcagtgtggg tgtgacagag atcaacaaga ctgcaggagc acagctggcc agtgggactg    420
acgcggctcc agaggcttgg ctagaggatg aaaggtcagt cctgcaagaa acatttcctc    480
ggctggatcc tccacctccc ataaccagaa agcgaacccc tcgggccctg aagaccaccc    540
aggacatgct gatttcatca cagcctgtcc tcagcagtct ggagtatggg acagagccat    600
cacctgggca ggcccaggac tccgctccca ctgcccagcc tgacgtccca gcagacgctt    660
cacagccaga ggccaccatg gaaagagaag agagaggcaa agttctgccc aatggagagg    720
tttccctgtc agtacctgac ctaatccaca aggatagcca ggacgaatcc aagctaagaa    780
tgactgagtg cagaagggcc tcctccccca gccttatcga gaggaatggc ttcaaactca    840
gcttgagccc catcagcctg gctgagtcct gggaggatgg cagccccccct cctcaggcac    900 ggacctccag cctcgacaat gagggccctc acccagacct gctgtccttt aatagagcc    960 tctgctcttt cctgctgagc tctg                                          984
```

<210> SEQ ID NO 35
<211> LENGTH: 648
<212> TYPE: DNA
<213> ORGANISM: Homo sapiens

<400> SEQUENCE: 35

```
gggatggcag ccctaaacac agcatggcaa ctcatctact cactcatgaa agattaaaaa     60
atggaaacca acgtatttca tcttatgctc tgcgtcactt ctgctcggac tcataaatcc    120
acgtctcttt gctttggcca cttcaactca tatccaagcc ttcctttaat tcatgattta    180
ttgctggaaa tatcctttca actctcagca cctcatgaag acgcgcgctt aactccggag    240
gagctagaaa gagcttccct tctacagata ctgccagaga tgctgggtgc agaaagaggg    300
gatattctca ggaaagcaga ctcaagtacc aacattttta acccaagagg aaatttgaga    360
aagtttcagg atttctctgg acaagatcct aacattttac tgagtcatct tttggccaga    420
atctggaaac catacaagaa acgtgagact cctgattgct tctggaaata ctgtgtctga    480
agtgaaataa gcatctgtta gtcagctcag aaacacccat cttagaatat gaaaaataac    540
acaatgcttg atttgaaaac agtgtggaga aaaactaggc aaactacacc ctgttcattg    600
ttacctggaa aataaatcct ctatgttttg cacaaaaaaa aaaaaaaa                 648
```

<210> SEQ ID NO 36
<211> LENGTH: 583

<212> TYPE: DNA
<213> ORGANISM: Homo sapiens

<400> SEQUENCE: 36

```
acactcgctt ctggaacgtc tgaggttatc aataagctcc tagtccagac gccatgggtc    60
atttcacaga ggaggacaag gctactatca caagcctgtg gggcaaggtg aatgtggaag   120
atgctggagg agaaaccctg gaaggctcc tggttgtcta cccatggacc cagaggttct    180
ttgacagctt tggcaacctg tcctctgcct ctgccatcat gggcaacccc aaagtcaagg   240
cacatggcaa gaaggtgctg acttccttgg gagatgccat aaagcacctg gatgatctca   300
agggcacctt tgcccagctg agtgaactgc actgtgacaa gctgcatgtg gatcctgaga   360
acttcaagct cctgggaaat gtgctggtga ccgttttggc aatccatttc ggcaaagaat   420
tcacccctga ggtgcaggct tcctggcaga agatggtgac tggagtggcc agtgccctgt   480
cctccagata ccactgagct cactgcccat gatgcagagc tttcaaggat aggctttatt   540
ctgcaagcaa tcaaataata aatctattct gctaagagat cac                     583
```

<210> SEQ ID NO 37
<211> LENGTH: 4567
<212> TYPE: DNA
<213> ORGANISM: Homo sapiens

<400> SEQUENCE: 37

```
acagccaatc ccccgagcgg ccgccaacat gctctttgag ggcttggatc tggtgtcggc    60
gctggccacc ctcgccgcgt gcctggtgtc cgtgacgctg ctgctggccg tgtcgcagca   120
gctgtggcag ctgcgctggg ccgccactcg cgacaagagc tgcaagctgc ccatccccaa   180
gggatccatg ggcttcccgc tcatcggaga gaccggccac tggctgctgc agggttctgg   240
cttccagtcg tcgcggaggg agaagtatgg caacgtgttc aagacgcatt tgttggggcg   300
gccgctgata cgcgtgaccg cgcgcggaga acgtgcgcaag atcctcatgg gcgagcacca   360
cctcgtgagc accgagtggc ctcgcagcac ccgcatgttg ctgggcccca acacggtgtc   420
caattccatt ggcgacatcc accgcaacaa gcgcaaggtc ttctccaaga tcttcagcca   480
cgaggccctg gagagttacc tgcccaagat ccagctggta tccaggaca cactgcgcgc    540
ctggagcagc cacccgagg ccatcaacgt gtaccaggag gcgcagaagc tgaccttccg   600
catggccatc cgggtgctgc tgggcttcag catccctgag gaggaccttg gcacctctt    660
tgaggtctac cagcagtttg tggacaatgt cttctccctg cctgtcgacc tgcccttcag   720
tggctaccgg cggggcattc aggctcggca gatcctgcag aaggggctgg agaaggccat   780
ccgggagaag ctgcagtgca cacagggcaa ggactacttg gacgccctgg acctcctcat   840
tgagagcagc aaggagcacg ggaaggagat gaccatgcag gagctgaagg acgggaccct   900
ggagctgatc tttgcggcct atgccaccac ggccagcgcc agcacctcac tcatcatgca   960
gctgctgaag cacccactg tgctggaaa gctgcgggat gagctgcggg ctcatggcat   1020
cctgcacagt ggcggctgcc cctgcgaggg cacactgcgc ctggacacgc tcagtgggct   1080
gcgctacctg gactgcgtca tcaaggagg catgcgcctg ttcacgcccca tttccggcgg   1140
ctaccgcact gtgctgcaga ccttcgagct tgatggtttc cagatcccca aaggctggag   1200
tgtcatgtat agcatccggg acacccatga cacagcgccc gtgttcaaag acgtgaacgt   1260
gttcgacccc gatcgcttca gccaggcgcg gagcgaggac aaggatggcc gcttccatta   1320
cctcccgttc ggtggcggtg tccggacctg cctgggcaag cacctggcca agctgttcct   1380
```

```
gaaggtgctg gcggtggagc tggctagcac cagccgcttt gagctggcca cacggacctt    1440
cccccgcatc accttggtcc ccgtcctgca ccccgtggat ggcctcagcg tcaagttctt    1500
tggcctggac tccaaccaga acgagatcct gccggagacg gaggccatgc tgagcgccac    1560
agtctaaccc aagacccacc cgcctcagcc cagcccaggc agcggggtgg tggttgtggg    1620
aggtagaaac ctgtgtgtgg gagggggccg gaacggggag ggcgagtggc ccccatactt    1680
gccctccctt gctcccccte cctggcaaac cctacccaaa gccagtgggc ccattccta    1740
gggctgggct ccccttctgg ctccagcttc cctccagcca ctccccattt accatcagct    1800
cagcccctgg gaagggcgtg gcaggggctc tgcatgcccg tgacagtgtt aggtgtcagc    1860
gcgtgctaca gtgtttttgt gatgttctga actgctccct tccctccgtt cctttcggac    1920
ccttttagct ggggttgggg gacgggaaga gccgtgcccc cttgggcgca ctcttcagcg    1980
tctcctcctc ctgcgccccc actgcgtctg cccaggaaca gcatcctggg tagcagaaca    2040
ggagtcaacc ttggcggggc gggggctgcg tccaacctgg agattgccct tccctatgcc    2100
acggttccca ccctccctca ccagtttgga caatttgaaa ttacctattg ctgctacttg    2160
ttctgtcctc tgaccttggg gcaaaggagc cccaggccct gtctccccag catcctccct    2220
ggtggccctg gcaggtgca ctgacacccc caccttccca tccctgctg aaccaggccc    2280
tgttacacac agccgcctaa ggcccgcggc tcatgtgctg cccgccccca tatttattca    2340
ctgatagaga atcttgggga tgctggggtc tggagtgaac atctcctccc cttcatgccc    2400
tagcctgtgt tctagctgtc ctggcgagac ttctgtgagt gaagaggaag gggtctctgg    2460
tcaaacccag cccccagggc ctagggttga aagccttccc cggctccggg cattatttgg    2520
gtttaatctc ggagcctcac tcctggactg aagtccggtg cctctgcctt atccctggtg    2580
gagatggaat gtgccccatt gcctcctccc tctcctgtca aaaaccctga tcaggtagat    2640
ttggaggcgg ccacgatttc ctgtttggcc cctgttcacc ccagtgcact ggccctgact    2700
ccaggcgtga gtatgggaa ggatacgggt tcttctgacg gggagcaagg gcctccgtct    2760
tcccttcctt aactctcccc ctttgccctc cgccctgaaa aaggtgtcct tgaagtccct    2820
tccacctcta tgccactgtc tgcttagccc agctcagggg tggggaagag gcgaaagcgt    2880
ggggggaggtg agcgcagcgg cagttctgcc tcggagctga ttgcagggcc ctgtgtggtc    2940
tccggacagc tgcgggaagg ctgccgcagc tgaagctgaa gaggcggcta cgtgcggttt    3000
gtcagggga ttgggttgaa aactggccag tcgggatgac tgggtgaaag aggagtagct    3060
cctgccactg gcgttttgag tgttggcaat ttgggatgcc tcctggggaa ggtttccggg    3120
cgtttggtga gtctctagat ttttccttgc tttctgtgtt tattggtttt tgatgttgta    3180
aaagcaatga atcccctta caagaaaatc gaaaacacag aagaatgaag gacatgccag    3240
tccccgatcg ctgctgtgag cacctcagtg gctccctcag accagatccc gtaggcagcc    3300
ccacagaccg accctgaccc cactcacagc caccctgaag atagactata ggaacgggcc    3360
cataccacac agactgctct ccaatccctg agtctcagat gtttcattta tttcctactt    3420
ttccactact aaaaaacagt gtggaataga cattattggc aaaattgctc atccctaatc    3480
ctgaaaaaca ggccagaatg ggtaaagact tgtcaaagct gcaacatag ctacatggtg    3540
cacccggacc tgtaccccct ccccccaaca caaaaccagt gtctgggagg ttcatttcc    3600
tttaaactga tccagctggc cctgaaccaa ttgttttga ctgagtatct aggagagcag    3660
taagtggaac ttcagacaag cccactgggt ctggtccagg tgaggggcag ggggcatggg    3720
gctgggaggt ctcagggggcc ttccctgggg gtggccagcc tggtagggg cagagaagga    3780
```

```
aaagctgagg ggggtccctg tgagggagga agaaggatc atttgccccg ctgggtctca    3840
aaggcagtga gaagagagct gaagaaagct ctggctggct gacaggatcc ctgtgttgta    3900
attggtccct cctttcagct ctctagtgag atgcccgtgt ctgtgcgtgt gcgtgtgtgt    3960
ttcatacagc tagcattaga tgggtgatgt ttcttactta tcatccctaa ctattgcaac    4020
ttgaccttaa aaagacaaaa ccccacaaaa ctcttcctgc cacgggcttg cagattgaag    4080
cactttcgat gttgggcgct ggcgtttgtg ttctgggcac caccgtgacc ctgcccagat    4140
ggctataata ttattttata cacaaacctt ttttttcata aatgttataa ttttgtgtct    4200
gtctttataa actattataa gtactatttt tgttataatt caaaatagat atttagtata    4260
aagttttgc tgttaaatat ttgttattta gtaaaatatg aattttgctc tattgtaaac    4320
atggttcaaa atattaatat gtttttatca cagtcgtttt aatattgaaa aagcacttgt    4380
gtgttttgtt ttgatatgaa actggtaccg tgtgagtgtt tttgctgtcg tggttttaat    4440
ctgtatataa tattccatgt tgcatattaa aaacatgaat gttgtgcatt ttgtgatttt    4500
ggaaatactc aatgtggctc ttctataggc ttctagaata aaccgtgggg acccgcaaaa    4560
aaaaaaa                                                               4567

<210> SEQ ID NO 38
<211> LENGTH: 1517
<212> TYPE: DNA
<213> ORGANISM: Homo sapiens

<400> SEQUENCE: 38
gcgaggcagg agccggcggc tgggctccgc agcgcagcca gcgcagcgcg gcgccccggg      60
cccggcccca tgcccgcagc cccgccggac cgtccttgag cgcgggcgcc tagcccgcgc     120
cccctgcccg ccggcaccat tgcccgacg gcgcggccgg gcgccccggc gctccccagg     180
ctccgcgcgg gccgaaagac gctgctagcg gccgccgcgg gtgtggtgat gctgctggtg     240
ctggtggtgc tcatccccgt gctggtgagc tcggcggcc cggaaggcca ctatgagatg     300
ctgggcacct gccgcatggt gtgcgacccc taccccgcgc ggggcccgg cgccggcgcg     360
cggaccgacg gcggcgacgc cctgagcgag cagagcggcg cgccccgcc ttccacgctg     420
gtgcagggcc cccaggggaa gccgggccgc accggcaagc ccggccctcc ggggcctccc     480
ggggacccag gtcctcccgg ccctgtgggg ccgccggggg agaagggtga gccaggcaag     540
ccgggccctc cggggctgcc gggcgcgggg gcagcggcg ccatcagcac tgccacctac     600
accacggtgc cgcgcgtggc cttctacgcc ggcctcaaga ccccacga gggttacgag     660
gtactcaagt ttgacgacgt ggtcaccaac ctaggcaaca actacgacgc ggccagcggc     720
aagtttacgt gcaacattcc cggcacctac tttttcacct accatgtcct catgcgcggc     780
ggcgacggca ccagtatgtg ggcagaccctc tgcaagaatg ccaggtgcg ggccagtgct     840
attgcccagg acgcggacca gaactacgac tacgccagca cagcgtgat cctgcacctg     900
gacgccggcg acgaggtctt catcaagctg gatggaggca agcacacgg cggcaacagc     960
aacaaataca gcacgttctc tggccttcatc atctactccg actgagctcc ccacgtctcc    1020
ctccacccac gtccctcacc cgccggggtc ccctccgggg ggcagacg atgactcgcc    1080
cctcgcccac ccgctcgctg ccgggccctc cccggctatg acgcccccgg cccgtgctca    1140
acaccgcctg ggccacagct aggccctccc accggctcgc tgcagagccg ggcccagcgc    1200
gccctgtccc cgtgccaggg aaccgggggtt gaccgccccc gcccagcccg cgctatatat    1260
```

```
ttgtacaata ggactgttta ctgcccacct ccgcctgcca gcccacccca gcctggggag   1320
aggtcgcggc ggcgggtttg cttcctgcgc tctgagatga gctgccctcc gctccctccg   1380
gggtggcgcg cccggggggag gggggagttg ggggctggat agcttcccag caccctcaga   1440
gcccccgccc ggctgtgccc cgtctgacca aagttataat aaaaacattt tcaccccgca   1500
aaaaaaaaaa aaaaaa                                                   1517

<210> SEQ ID NO 39
<211> LENGTH: 20
<212> TYPE: DNA
<213> ORGANISM: artificial sequence
<220> FEATURE:
<223> OTHER INFORMATION: Primer

<400> SEQUENCE: 39
cagtgaattt gggctgctgt                                                 20

<210> SEQ ID NO 40
<211> LENGTH: 20
<212> TYPE: DNA
<213> ORGANISM: artificial sequence
<220> FEATURE:
<223> OTHER INFORMATION: Primer

<400> SEQUENCE: 40
tgacgactgg gcctacatac                                                 20

<210> SEQ ID NO 41
<211> LENGTH: 21
<212> TYPE: DNA
<213> ORGANISM: artificial sequence
<220> FEATURE:
<223> OTHER INFORMATION: Primer

<400> SEQUENCE: 41
cctcaacaac cttccactgc c                                               21

<210> SEQ ID NO 42
<211> LENGTH: 20
<212> TYPE: DNA
<213> ORGANISM: artificial sequence
<220> FEATURE:
<223> OTHER INFORMATION: Primer

<400> SEQUENCE: 42
caggtagctc agcagtcgta                                                 20

<210> SEQ ID NO 43
<211> LENGTH: 20
<212> TYPE: DNA
<213> ORGANISM: artificial sequence
<220> FEATURE:
<223> OTHER INFORMATION: Primer

<400> SEQUENCE: 43
gcagccagtc atccaggata                                                 20

<210> SEQ ID NO 44
<211> LENGTH: 20
<212> TYPE: DNA
<213> ORGANISM: artificial sequence
<220> FEATURE:
<223> OTHER INFORMATION: Primer

<400> SEQUENCE: 44
```
atctttggga atgcgatgcc                                        20

<210> SEQ ID NO 45
<211> LENGTH: 20
<212> TYPE: DNA
<213> ORGANISM: artificial sequence
<220> FEATURE:
<223> OTHER INFORMATION: Primer

<400> SEQUENCE: 45
tgtcgtggga atgagtcagc                                        20

<210> SEQ ID NO 46
<211> LENGTH: 20
<212> TYPE: DNA
<213> ORGANISM: artificial sequence
<220> FEATURE:
<223> OTHER INFORMATION: Primer

<400> SEQUENCE: 46
tggatccatc tgagcaggtc                                        20

<210> SEQ ID NO 47
<211> LENGTH: 20
<212> TYPE: DNA
<213> ORGANISM: artificial sequence
<220> FEATURE:
<223> OTHER INFORMATION: Primer

<400> SEQUENCE: 47
cactaaggtc attcccgcct                                        20

<210> SEQ ID NO 48
<211> LENGTH: 20
<212> TYPE: DNA
<213> ORGANISM: artificial sequence
<220> FEATURE:
<223> OTHER INFORMATION: Primer

<400> SEQUENCE: 48
agcacgtaca gcttcaccat                                        20

<210> SEQ ID NO 49
<211> LENGTH: 20
<212> TYPE: DNA
<213> ORGANISM: artificial sequence
<220> FEATURE:
<223> OTHER INFORMATION: Primer

<400> SEQUENCE: 49
tcagtgtcta cctgcccaag                                        20

<210> SEQ ID NO 50
<211> LENGTH: 20
<212> TYPE: DNA
<213> ORGANISM: artificial sequence
<220> FEATURE:
<223> OTHER INFORMATION: Primer

<400> SEQUENCE: 50
gccttgactt gctgggttac                                        20

<210> SEQ ID NO 51
<211> LENGTH: 21
<212> TYPE: DNA

```
<213> ORGANISM: artificial sequence
<220> FEATURE:
<223> OTHER INFORMATION: Primer

<400> SEQUENCE: 51
ggccctctaa ttggaagagt c                                              21

<210> SEQ ID NO 52
<211> LENGTH: 21
<212> TYPE: DNA
<213> ORGANISM: artificial sequence
<220> FEATURE:
<223> OTHER INFORMATION: Primer

<400> SEQUENCE: 52
ccaagatcca actacgagct t                                              21

<210> SEQ ID NO 53
<211> LENGTH: 20
<212> TYPE: DNA
<213> ORGANISM: artificial sequence
<220> FEATURE:
<223> OTHER INFORMATION: Primer

<400> SEQUENCE: 53
aggctgctgc cacataaggt                                                20

<210> SEQ ID NO 54
<211> LENGTH: 21
<212> TYPE: DNA
<213> ORGANISM: artificial sequence
<220> FEATURE:
<223> OTHER INFORMATION: Primer

<400> SEQUENCE: 54
agcgtcgtga gaggtcactt g                                              21
```